(12) United States Patent
Rader et al.

(10) Patent No.: US 12,010,998 B2
(45) Date of Patent: *Jun. 18, 2024

(54) SYSTEMS, METHODS, AND APPARATUSES FOR DISINFECTION AND DECONTAMINATION

(71) Applicant: Chorus, LLC, Marlboro, MA (US)

(72) Inventors: Richard S. Rader, Wayland, MA (US); Kenneth J. Heater, Delaware, OH (US); Raymond Desabato, Southborough, MA (US); Daniel P. Lorch, London, OH (US); Adriane L. Lewis, Columbus, OH (US); Timothy N. Wells, Manchester, CT (US)

(73) Assignee: Chorus, LLC, Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/146,628

(22) Filed: Dec. 27, 2022

(65) Prior Publication Data

US 2023/0200396 A1 Jun. 29, 2023

Related U.S. Application Data

(63) Continuation of application No. 17/567,117, filed on Jan. 1, 2022, now Pat. No. 11,533,914, which is a
(Continued)

(51) Int. Cl.
*A01N 59/00* (2006.01)
*A61L 2/20* (2006.01)
(Continued)

(52) U.S. Cl.
CPC .............. *A01N 59/00* (2013.01); *A61L 2/20* (2013.01); *A61L 2/24* (2013.01); *A61L 9/015* (2013.01);
(Continued)

(58) Field of Classification Search
CPC . A01N 59/00; A61L 9/14; A61L 9/015; A61L 2209/16
See application file for complete search history.

(56) References Cited

U.S. PATENT DOCUMENTS

| 4,852,613 A | 8/1989 | Tippetts et al. |
| 6,042,802 A | 3/2000 | Drake |

(Continued)

FOREIGN PATENT DOCUMENTS

| JP | 1993037245 U | 5/1993 |
| JP | 1995227418 A | 9/1995 |

(Continued)

OTHER PUBLICATIONS

Office Action issued in U.S. Appl. No. 18/063,197 on Sep. 19, 2023.
(Continued)

*Primary Examiner* — Sean E Conley
(74) *Attorney, Agent, or Firm* — Thomas Y. Kendrick; Benjamen E. Kern; Kern Kendrick, LLC

(57) ABSTRACT

In one aspect, a system for generating and monitoring an antimicrobial is provided, the system including: a microprocessor and/or a microcontroller; an external communications device; a computational system; an antimicrobial sensor and/or an environmental sensor; and an antimicrobial generator, wherein the external communications device, the computational system, the antimicrobial generator, and the antimicrobial sensor and/or the environmental sensor are operatively connected to the microprocessor and/or the microcontroller. The system may further include a separate sensor sub-system comprising: a sensor sub-system microprocessor and/or a sensor sub-system microcontroller; a sensor sub-system external communications device; a sensor sub-system antimicrobial sensor and/or a sensor sub-system environmental sensor; and a sensor sub-system computational system. The system may further include a separate
(Continued)

generation sub-system comprising: a generation sub-system microprocessor and/or a generation sub-system microcontroller; a generation sub-system external communications device; and a generation sub-system antimicrobial generator.

19 Claims, 91 Drawing Sheets

Related U.S. Application Data continuation-in-part of application No. PCT/US2021/036501, filed on Jun. 8, 2021.

(60) Provisional application No. 63/036,412, filed on Jun. 8, 2020, provisional application No. 63/049,524, filed on Jul. 8, 2020, provisional application No. 63/049,541, filed on Jul. 8, 2020, provisional application No. 63/049,919, filed on Jul. 9, 2020, provisional application No. 63/081,459, filed on Sep. 22, 2020, provisional application No. 63/126,734, filed on Dec. 17, 2020, provisional application No. 63/157,368, filed on Mar. 5, 2021.

(51) Int. Cl.
*A61L 2/24* (2006.01)
*A61L 9/015* (2006.01)
*A61L 9/14* (2006.01)
*A61P 31/04* (2006.01)
*A61P 31/12* (2006.01)
*G16H 50/20* (2018.01)
*G16H 50/80* (2018.01)
*G16H 70/60* (2018.01)
*A61L 101/06* (2006.01)

(52) U.S. Cl.
CPC ............... *A61L 9/14* (2013.01); *A61P 31/04* (2018.01); *A61P 31/12* (2018.01); *G16H 50/20* (2018.01); *G16H 50/80* (2018.01); *G16H 70/60* (2018.01); *A61L 2101/06* (2020.08); *A61L 2202/11* (2013.01); *A61L 2202/14* (2013.01); *A61L 2202/15* (2013.01); *A61L 2202/25* (2013.01); *A61L 2209/16* (2013.01)

(56) References Cited

U.S. PATENT DOCUMENTS

| | | | |
|---|---|---|---|
| 7,354,551 B2 | 4/2008 | Mielnik | |
| 7,700,056 B2 | 4/2010 | Hill | |
| 9,517,284 B1 | 12/2016 | Stibich et al. | |
| 10,071,177 B1 | 9/2018 | Kellogg, Jr. | |
| 11,533,914 B2* | 12/2022 | Rader | F24F 8/15 |
| 2005/0233198 A1 | 10/2005 | Nuzzo et al. | |
| 2006/0051285 A1 | 3/2006 | Hawker et al. | |
| 2008/0167650 A1 | 7/2008 | Joshi et al. | |
| 2012/0121731 A1 | 5/2012 | Peters et al. | |
| 2016/0110657 A1 | 4/2016 | Gibiansky et al. | |
| 2016/0251219 A1 | 9/2016 | Richardson et al. | |
| 2018/0271450 A1 | 9/2018 | Kamath et al. | |
| 2021/0023250 A1 | 1/2021 | Golkowski et al. | |

FOREIGN PATENT DOCUMENTS

| | | |
|---|---|---|
| JP | 2002504005 A | 2/2002 |
| JP | 2003020207 A | 1/2003 |
| JP | 2008178479 A | 8/2008 |
| JP | 2013506495 A | 2/2013 |

OTHER PUBLICATIONS

Notification to make a divisional application issued in Chinese application No. 202180040939.9 on Aug. 28, 2023.
Office Action issued in Japanese Application No. 2022-575340 on May 16, 2023.
International Preliminary Report on Patentability in PCT/US2021/036501, dated Dec. 13, 2022.
International Search Report and Written Opinion issued in PCT/US2021/036501, dated Nov. 18, 2021.
International Search Report and Written Opinion issued in PCT/US2021/062496, dated Mar. 1, 2022.

* cited by examiner

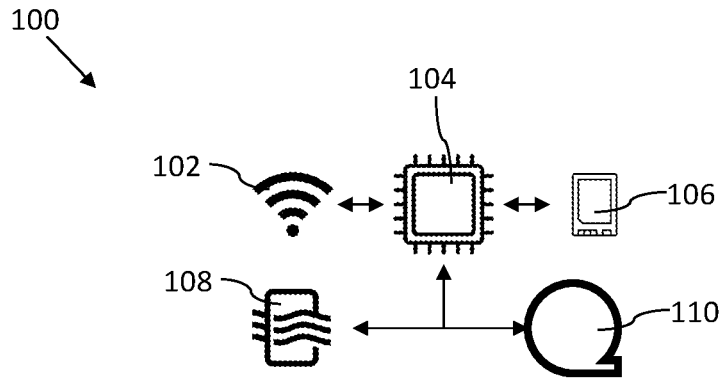
FIG. 1A
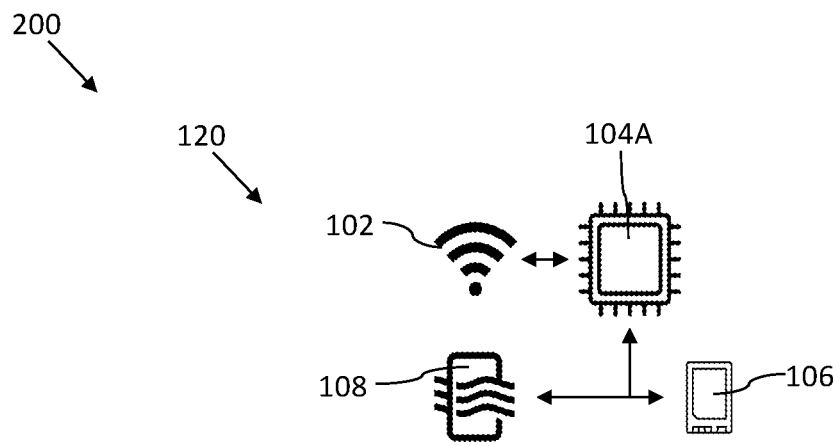
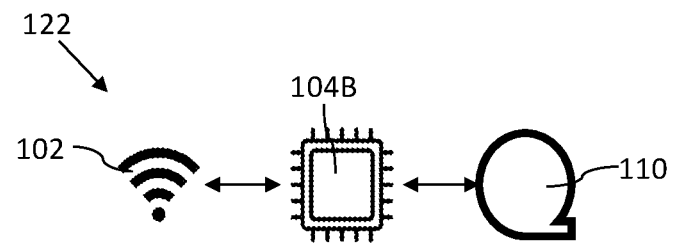
FIG. 2A

2700

2700

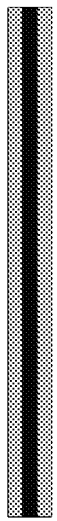
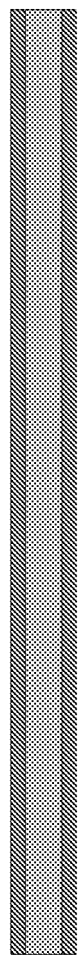
FIG. 32A
FIG. 32B
FIG. 32C
FIG. 32D
3200

3200

3900

Chlorine Dioxide: Prediction of Gas in Water and Air

| Volume of water | 4 | Liters |
| --- | --- | --- |
| Volume of air | 18.001 | Liters |
| Start ClO2 conc. in H2O | 500 | ppm |
| Mass of ClO2 produced | 2000 | mg |

| mol wt ClO2 | 67.451 |
| --- | --- |
| Total moles ClO2 | 0.029651 |

| Volume converter | | |
| --- | --- | --- |
| L (ft) | W (ft) | H (ft) |
| 11.2 | 7.7 | 7.4 |
| Volume = | 18.001 | Liters |

| Gallons | 1 |
| --- | --- |
| Liters | 3.78541 |

| Temp (C) | KH (T) | V in (T) | x mol frac in H2O | y mol frac in gas | mg ClO2 in H2O | ppm ClO2 air | mg/m3 in air | mg ClO2 in air |
| --- | --- | --- | --- | --- | --- | --- | --- | --- |
| 0 | 21.96 | 22.3983 | 1.66993E-06 | 0.0000364 | 6.22 | 36.44 | 109.7 | 1975.1342 |
| 5 | 27.46 | 22.8083 | 1.35429E-06 | 0.0000372 | 5.07 | 37.19 | 110.0 | 1979.7008 |
| 10 | 34.06 | 23.2183 | 1.11341E-06 | 0.0000379 | 4.17 | 37.93 | 110.2 | 1983.3110 |
| 15 | 41.94 | 23.6283 | 9.21428E-07 | 0.0000387 | 3.45 | 38.65 | 110.3 | 1986.1856 |
| 20 | 51.27 | 24.0383 | 7.67864E-07 | 0.0000394 | 2.88 | 39.37 | 110.5 | 1988.4905 |
| 25 | 62.26 | 24.4483 | 6.43740E-07 | 0.0000401 | 2.41 | 40.08 | 110.6 | 1990.3509 |
| 30 | 75.11 | 24.8583 | 5.42403E-07 | 0.0000408 | 2.03 | 40.78 | 110.7 | 1991.8624 |
| 35 | 90.08 | 25.2683 | 4.60470E-07 | 0.0000415 | 1.73 | 41.48 | 110.7 | 1993.0960 |
| 40 | 107.40 | 25.6783 | 3.92879E-07 | 0.0000422 | 1.47 | 42.17 | 110.8 | 1994.1141 |
| 50 | 150.19 | 26.4983 | 2.86977E-07 | 0.0000436 | 1.09 | 43.55 | 110.9 | 1995.6535 |
| 60 | 205.86 | 27.3183 | 2.18220E-07 | 0.0000449 | 0.82 | 44.92 | 110.9 | 1996.7269 |

Henry's law states that the solubility of a gas in a liquid is directly proportional to the partial pressure of the gas above the liquid. In a mixture of gases, each gas has a partial pressure which is the hypothetical pressure of that gas if it alone occupied the volume of the mixture at the same temperature. The total pressure of an ideal gas mixture is the sum of the partial pressures of each individual gas in the mixture.

$p = kH \times c$; $p$ = partial pressure of the solute in the gas above the solution (atm); $kH$ = a constant with the dimensions of pressure divided by concentration. The constant, known as the Henry's law constant, depends on the solute, the solvent and the temperature. (L*atm/mol); c = concentration of the solute (mol/L)

FIG. 45

TEST T13 - Gas Uniformity Test
Date: 2/11/20
Furnished room w/fan and elevated RH (80% set point (max))
Yellow Jacket with one 12G
Portasens datalogger inadvertently not activated for logging

| Port ID | Gas Uniformity | | | | |
|---|---|---|---|---|---|
| | Concentration Measurements (ppm) | | | | |
| | Round 1 | Round 2 | Round 3 | Mean | Std. Dev. |
| 1 | 216 | 186 | 156 | 186 | 21 |
| 2 | 218 | 186 | 152 | 185 | 23 |
| 3 | 211 | 176 | 152 | 180 | 21 |
| 4 | 210 | 178 | 151 | 180 | 21 |
| 5 | 224 | 171 | 161 | 185 | 24 |
| 6 | 227 | 191 | 162 | 193 | 23 |
| 7 | 194 | 164 | 145 | 168 | 17 |
| 8 | 201 | 170 | 148 | 173 | 19 |
| 9 | 223 | 183 | 152 | 186 | 25 |
| 10 | 206 | 172 | 151 | 176 | 20 |
| 11 | 230 | 184 | 163 | 192 | 24 |
| 12 | 194 | 180 | 157 | 177 | 13 |
| Mean | 213 | 178 | 154 | 182 | n/a |
| Std. Dev | 12 | 8 | 6 | 8 | n/a |

When making rounds, I tried to follow the same pattern. I started with the door (port11), moved clockwise and started at the top (port6), then bottom (port5), continued clockwise (port9), and continued this way around the container. However, I did not follow this pattern perfectly (ex. in the first round, forgetting port 12 until I had done the rest).

*Port 5, round 2 was observed to fluctuate between 160 and 180ppm, never settling at a specific value for very long. This could have been caused by the position of the fan in the room, however it did not fluctuate like this in round 1 or 3.

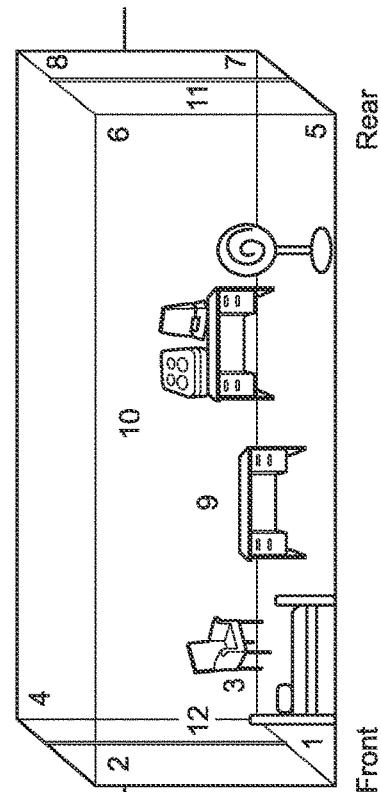

FIG. 46

| Acid Generation | NaClO2 Solution (80%) g/mL | Volume NaClO2 Solution ul | Activator | Activator Conc. | Volume Activator ul | Molar Ratio [NaClO2 : Activator] | ClO2 Conc. In Tote ppm | Complete Conversion (mg ClO2) | Measured (mg ClO2) | Measured Efficiency |
|---|---|---|---|---|---|---|---|---|---|---|
| 1 | 0.75 | 22 | Na2S2O8 | 0.5 g/mL | 139 | 2 | 48.6 | 9.84 | 10.15 | 103% |
| 2 | 0.75 | 22 | HCl | 12 M | 36 | 3 | 44.3 | 7.88 | 9.25 | 117% |
| 3 | 0.75 | 22 | CH2O2 | 100% | 33 | 6 | 54 | 9.84 | 11.28 | 115% |

FIG. 54A

| Electrolysis Generation | Cell Type | Anolyte: NaClO2 Solution (80%) g/mL | Catholyte: NaNO3 Soln. g/mL | Potential (V) | Current (A) | Time On (min) | Power (W) | Energy (J) | ClO2 Conc. In Tote ppm | ClO2 (mg) Generated | ClO2 Measured (mg) | Measured Efficiency |
|---|---|---|---|---|---|---|---|---|---|---|---|---|
| 5 | Membrane | 0.25 | 0.19 | 12 | 0.468 | 3 | 5.6 | 1011 | 114 | 24.99 | 23.81 | 95% |
| | Membrane | 0.50 | 0.38 | 12 | 0.600 | 1.5 | 7.2 | 648 | 73 | 16.50 | 15.00 | 91% |
| 4 | No Membrane | 0.50 | None | 5 | 1.6 | 1.35 | 8.0 | 648 | 44 | 16.50 | 9.00 | 55% |

FIG. 54B

Chemical Use - 1000 ft3 room

| Generation Method | Activator | Molar Ratio | Volume Ratio | Efficiency | NaClO2 Volume [µl] | Activator Volume [µl] | Total Volume [µl] | Total Volume [ml] | Single Dose - 0.10 ppm in 1000 ft3 — Total Volume [ml] — 1000 ft3, 30 days continuous operation, 5 air exchanges per hr, 250% makeup air | 1000 ft3, 30 days continuous operation, 5 air exchanges per hr, 100% makeup air — Total Volume [ml] |
|---|---|---|---|---|---|---|---|---|---|---|
| 1 | Na2S2O8 | 2 | 6.32 | 100% | 17.46 | 110.27 | 127.73 | | 114.96 | 459.82 |
| 2 | HCl | 3 | 1.64 | 100% | 17.46 | 28.95 | 46.41 | 0.05 | 41.77 | 167.08 |
| 3 | CH2O2 | 6 | 1.50 | 100% | 17.46 | 26.22 | 43.68 | 0.04 | 39.31 | 157.23 |
| 4 | Electrolysis | N/A | N/A | 55% | 31.74 | None | 31.74 | 0.03 | 28.57 | 114.27 |
| 5 | Membrane | N/A | N/A | 100% | 17.46 | None | 17.46 | 0.02 | 15.71 | 62.85 |

FIG. 54C

SYSTEMS, METHODS, AND APPARATUSES FOR DISINFECTION AND DECONTAMINATION

CROSS-REFERENCE TO RELATED APPLICATIONS

This application is a continuation-in-part of PCT Patent Application No. PCT/US2021/036501, filed on Jun. 8, 2021, which claims priority from U.S. Provisional Patent Application No. 63/036,412, filed on Jun. 8, 2020, U.S. Provisional Patent Application No. 63/049,524, filed on Jul. 8, 2020, U.S. Provisional Patent Application No. 63/049,541, filed on Jul. 8, 2020, U.S. Provisional Patent Application No. 63/049,919, filed on Jul. 9, 2020, U.S. Provisional Patent Application No. 63/081,459, filed on Sep. 22, 2020, U.S. Provisional Patent Application No. 63/126,734, filed on Dec. 17, 2020, and U.S. Provisional Patent Application No. 63/157,368, filed on Mar. 5, 2021, each of which is incorporated by reference herein in its entirety.

BACKGROUND

Infectious diseases such as human immunodeficiency virus and acquired immune deficiency syndrome (HIV/AIDS), tuberculosis (TB), severe acute respiratory syndrome (SARS-CoV-1), Ebola virus disease (EVD), and coronavirus disease 2019 (COVID-19) are contagious diseases transmissible through direct contact from person to person, through indirect contact by breathing airborne droplets spread from an infected person, and through contact with surfaces of contaminated objects.

With the COVID-19 pandemic outbreak, facemask or respirator wearing and practicing social distancing may mitigate airborne droplets spread by potential neighboring human carriers. Nevertheless, both of these practices are defensive actions that do not destroy or disinfect the germs or viruses in the airborne droplets. Currently, methods that are used to generate antimicrobial gases or vapor are large and impractical for general household or office use or for personal use in a limited localized space, and methods of generating $ClO_2$ from liquid and solid precursor chemicals are slow and/or generate low quality $ClO_2$ solutions.

Antimicrobial gas, such as chlorine dioxide ($ClO_2$), has demonstrated capability as an antimicrobial or inactivator for pathogens on hard surfaces. In gas form, $ClO_2$ has demonstrated capability to disinfect hard surfaces and porous materials within three-dimensional spaces. $ClO_2$ gas has also been shown to kill or otherwise inactivate airborne pathogens, and even protect against airborne contagion.

$ClO_2$ gas is also currently used as a deodorizer in vehicles, rooms, and other enclosed spaces. Typical products used for enclosed space odor removal include placing a cup or container housing one or more dry solid chemical constituents (typically consisting of a chlorite salt and an activator), adding water to activate the $ClO_2$ generation process, enclosing the $ClO_2$ generation materials in the space for an extended period of time before opening up the space, removing the spent $ClO_2$ solution, and allowing the space to air out to reduce $ClO_2$ concentration to safe levels.

The present disclosure relates to a safe and effective system and method for quickly and safely generating antimicrobial gas (e.g., $ClO_2$ gas). Antimicrobial gas may be generated from small amounts of concentrated liquid and solid precursor chemicals and actively dispersing the antimicrobial gas into an enclosed three-dimensional space. Additionally, the present disclosure relates to a safe and effective system and method for monitoring antimicrobial gas concentration in the enclosed three-dimensional space and generating additional antimicrobial gas as necessary to maintain the desired concentration in the space. When used at higher concentrations, the resultant antimicrobial gas will sanitize or disinfect the air and contact surfaces within the enclosed space. At low concentrations (e.g., <0.1 ppm), the antimicrobial gas can be used to decrease or otherwise inactivate airborne pathogens and actively protect persons in the treated space against airborne contagions.

The present disclosure also relates to a safe and effective system and method of generating, monitoring, and controlling the concentration of antimicrobial gas that is generated on demand.

SUMMARY

In one aspect, a closed-loop system for generating and monitoring an antimicrobial is provided, the system comprising: a control sub-system comprising: a controller unit; a communications sub-system comprising: one or more of a wired communication mechanism and a wireless communication mechanism for connecting to an external network; a sensing sub-system comprising: one or more sensor oriented on a portion of the system open to air or contained in one or more plenum, wherein the one or more sensor is operatively connected to the control sub-system; a generation sub-system comprising: a reactor including a mixing chamber, wherein two or more reagents are combined in the mixing chamber to create an antimicrobial, and wherein the antimicrobial is applied to a volume under treatment; wherein the sensing sub-system samples air from the volume under treatment continuously or at intervals and measures the concentration of the antimicrobial present in the air from the volume under treatment; and wherein the generation sub-system generates the antimicrobial when the measured concentration of the antimicrobial in the air from the volume under treatment is below a predetermined threshold value. Additionally, or alternatively, the generation sub-system generates the antimicrobial in response to a difference between a target value and the sensing sub-system measurement.

In another aspect, a system for generating and monitoring an antimicrobial gas is provided, the system including: a microprocessor and/or a microcontroller; an external communications device; a computational system; an antimicrobial sensor and/or an environmental sensor; and an antimicrobial generator, wherein the external communications device, the computational system, the antimicrobial generator, and the antimicrobial sensor and/or the environmental sensor are operatively connected to the microprocessor and/or the microcontroller. The system may further include a separate sensor sub-system comprising: a sensor sub-system microprocessor and/or a sensor sub-system microcontroller; a sensor sub-system external communications device; a sensor sub-system antimicrobial sensor and/or a sensor sub-system environmental sensor; and a sensor sub-system computational system. The system may further include a separate generation sub-system comprising: a generation sub-system microprocessor and/or a generation sub-system microcontroller; a generation sub-system external communications device; and a generation sub-system antimicrobial generator. In another aspect, a network of these systems for generating and monitoring an antimicrobial gas is provided.

In another aspect, a system for generating and monitoring $ClO_2$ gas is provided, the system comprising: a device housing including an inlet; a microcontroller; one or more reagent containers containing a reagent; a microfluidic liquid dispensing and metering system; a microfluidic device for generating a $ClO_2$ gas from the reagent(s); a device for separation of $ClO_2$ gas and post-generator waste in communication with the air pump air duct and an air duct to one or more outlets; on-device or in-device waste storage prior to disposal; and one or more sensing system for either $ClO_2$ gas or the environment in which the device is installed.

In another aspect, a $ClO_2$ gas generator is provided, comprising: a base including a pressure generator; one or more reagent containers holding liquid reagent(s), the containers being pressurized by the pressure generator; a chamber passage in communication with the pressure chamber and the reagent container; one or more control valves in communication with the pressure generator and reagent container; one or more control valves in communication with the chamber passage and a microfluidic chip; a sensor system for determining the quantity, mass, or volume of the reagents transiting the chamber passage; a microfluidic chip having a generation chamber in communication with a second chamber passage; a second chamber passage in communication with a $CLO_2$ gas-liquid separation chamber; and, a waste container for storage and/or inactivation of post-$CLO_2$ generator waste products. Alternatively, the one or more reagent container may include a liquid dispensing and metering system, which may include positive displacement pumps (e.g., peristaltic pumps), wherein for a set rotation of the pump shaft a known amount of liquid reagent is pumped, thus not requiring additional measurement of liquid reagent introduced to the chamber.

In another aspect, a network of systems for generating and monitoring $ClO_2$ gas, is provided, the network comprising: a plurality of systems for generating and monitoring $ClO_2$ gas, including: a device housing including an inlet; a microcontroller; one or more reagent containers containing a reagent; a microfluidic device for generating a $ClO_2$ gas from the reagent; and a sensing system; wherein the microcontroller includes a communication device capable of communication between the plurality of systems, and wherein the communication device establishes distributed control of each system's microcontroller, wherein the microcontroller is controlled by machine learning algorithms to alter system performance.

In another aspect, a network of systems for generating and monitoring an antimicrobial gas is provided, the system including: a microprocessor and/or a microcontroller; an external communications device; a computational system; an antimicrobial sensor and/or an environmental sensor; and an antimicrobial generator, wherein the external communications device, the computational system, the antimicrobial generator, and the antimicrobial sensor and/or the environmental sensor are operatively connected to the microprocessor and/or the microcontroller. The system may further include a separate sensor sub-system comprising: a sensor sub-system microprocessor and/or a sensor sub-system microcontroller; a sensor sub-system external communications device; a sensor sub-system antimicrobial sensor and/or a sensor sub-system environmental sensor; and a sensor sub-system computational system. The system may further include a separate generation sub-system comprising: a generation sub-system microprocessor and/or a generation sub-system microcontroller; a generation sub-system external communications device; and a generation sub-system antimicrobial generator.

In another aspect, the microcontroller of the system will have the computational and local data storage ability to enable closed-loop control of the $ClO_2$ generation system, including but not limited to: local storage and microcontroller operations on data from sensor systems for $ClO_2$ levels to space environment variables like barometric pressure, humidity, temperature, occupancy, or sounds that may be used to alter generator system performance automatically or via user intervention; measurement, local storage, and microcontroller operations on data from microfluidic sub-systems such as mass/volume sensors of reagents, rotational or linear movement of positive displacement pumps, pressure generator performance, microfluidic chip-borne sensors, valve status to any other electronic sub-system to provide control as well as storage of system performance data for maintenance, alert, troubleshooting, inactive modes of operation, active modes of operation, and local setup.

In another aspect, the system has a communication device connected to the microcontroller and/or electronic components such that data from any electronic component within, on, or connected to the housing can be gathered, locally stored, operated on by the microcontroller, and transmitted to external data gathering systems on mobile to fixed devices.

In another aspect, linear, non-linear, proportional-integral-derivative control, machine learning, and/or artificial intelligence algorithms can be incorporated into the system microcontroller to alter system performance automatically or by user interactions. An example of local control includes alteration of system performance for detection of a virus or bacteria in the ambient air, altitude, temperature, air changes in the local space measured by changes in concentration in the air of spaces containing $ClO_2$, changes in occupancy by living beings, alterations for user preference, prediction of cycles of occupancy/vacancy, alerts as to normal or abnormal performance of the system, and the like.

In another aspect, a plurality of systems within a plurality of spaces which are arranged into a group connected via communication devices described above to each other for distributed control via coordination of each system's microcontroller, centralized unit control, and/or a combination of both local and distributed control.

In another aspect, linear, non-linear, proportional-integral-derivative control, machine learning, and/or artificial intelligence algorithms can be incorporated into the distributed network of systems by the aspects described above; example of distributed control include adjusting individual systems to achieve uniform and/or deliberately non-uniform distribution of $ClO_2$ in each individual generator's location across an entire building floor, multiple floors, or the entire building due to changes in $ClO_2$ concentration from HVAC, consumption or self-dissipation of $ClO_2$ gas, control of day/night generation cycles, sensing patterns across time, three-dimensional volumes, seasonal variations, to previously unknown factors which can be sensed either directly by the sensor systems in/on the system, inferred or traced to the signal measured, or directly traceable to the variations observed in $ClO_2$ concentrations across a collection of systems installed across distinctly separate to varying interconnection of real world spaces in which control of infectious species is desired.

In another aspect, the system for distribution and monitoring of $ClO_2$ gas in a three-dimensional space can be designed for a plurality of operating modes; the first operating mode is designed for occupied spaces, the second mode is designed for un-occupied spaces and may include one or more sub-modes to achieve desired outcomes; future user or engineered modes may be added. These modes may be changed by authorized users on the unit, via connected mobile devices, and/or by a centralized distributed control system connected to a plurality of units.

BRIEF DESCRIPTION OF THE DRAWINGS

FIG. 1A illustrates a schematic of an example system 100 for generating and monitoring an antimicrobial gas.

FIG. 2A illustrates a schematic of an example complimentary sensing sub-system 120 and generation sub-system 122 for generating and monitoring an antimicrobial gas.

FIG. 32A illustrates an example of an antimicrobial generator 3200 in the form of a solution treated single or multi-ply porous material.

FIG. 32B illustrates an example of antimicrobial generator 3200 with liquid reagents absorbed or adsorbed on substrates and blended with a porous matrix material with optional addition of an exterior film to control release.

FIG. 32C illustrates an example of antimicrobial generator 3200 with solid reagents blended in a porous material and optional addition of an exterior film to control release.

FIG. 32D illustrates an example of antimicrobial generator 3200 in the form of a perforated pouch.

FIG. 45 illustrates a table showing temperature effects to solubility of $ClO_2$ gas in water and in air and required amount of $ClO_2$ gas for a defined room size.

FIG. 46 illustrates a uniformity of $ClO_2$ gas concentration distributed within a room.

FIG. 54A illustrates results of $ClO_2$ generation using system 5300 or similar systems.

FIG. 54B illustrates results of $ClO_2$ generation using system 5300 or similar systems.

FIG. 54C illustrates requirements for $ClO_2$ generation using system 5300 or similar systems.

FIG. 61A illustrates a perspective view of an example antimicrobial gas generator 6100.

FIG. 61B illustrates a sectional view of an example antimicrobial gas generator 6100.

DETAILED DESCRIPTION

Closed-Loop Antimicrobial Concept

Figure 1B:
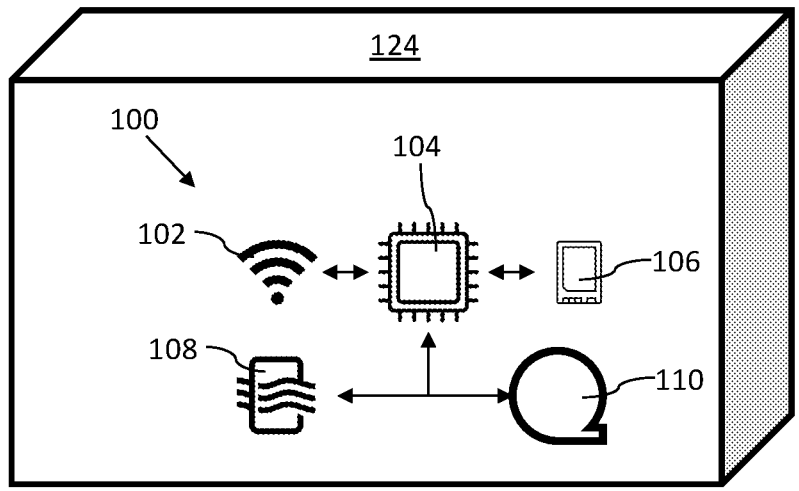
FIG. 1B illustrates a schematic of system 100 oriented within a volume under treatment 124.
Figure 2B:
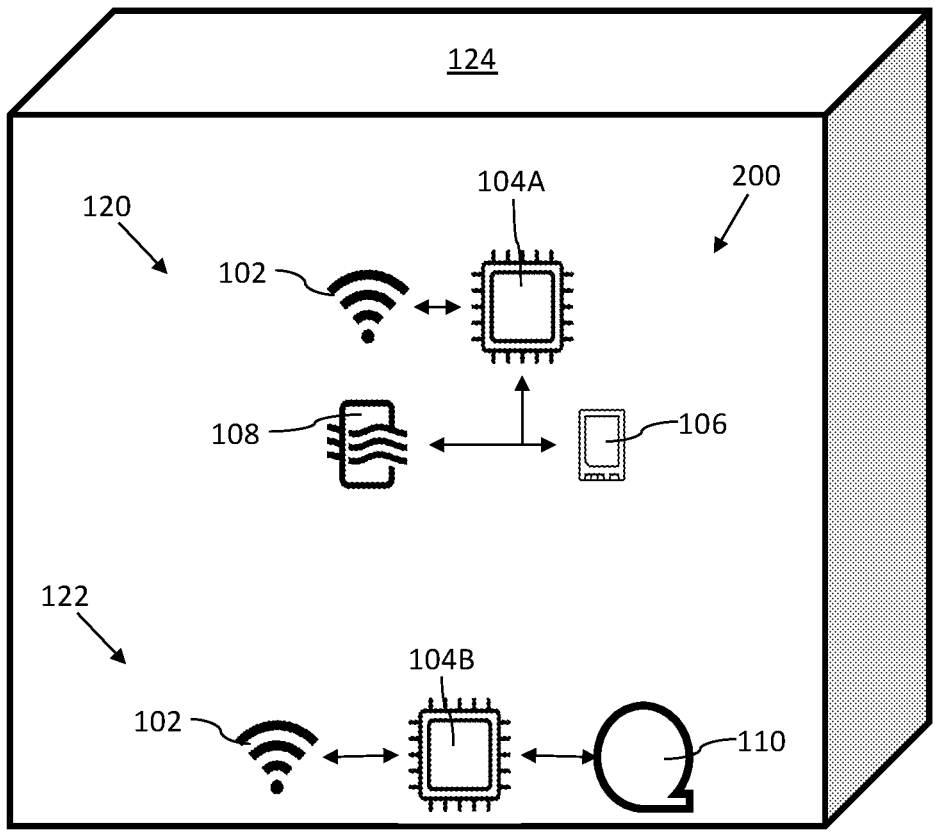
FIG. 2B illustrates a schematic of sensing sub-system 120 and generation sub-system 122 within a volume under treatment 124.
Figure 1C:
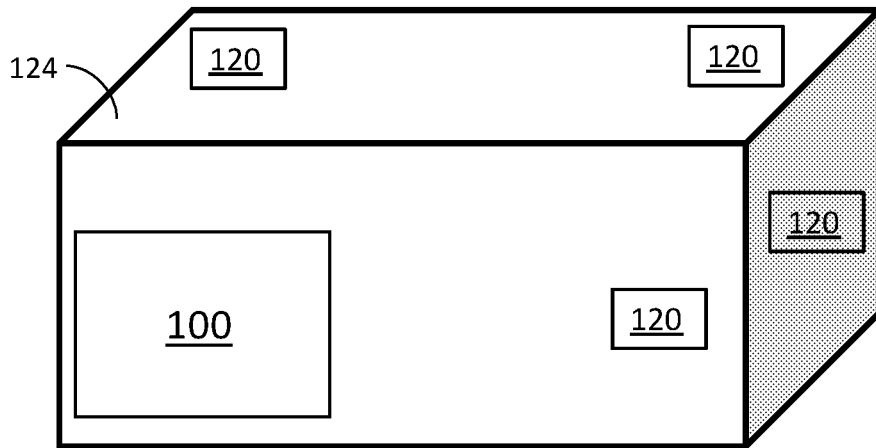
FIG. 1C illustrates a schematic of system 100 oriented within a volume under treatment 124.

A system is provided including an interconnection of platform component elements described below. FIGS. 1A-1C illustrate a system 100 for generating and monitoring an antimicrobial gas. FIGS. 2A-2E illustrate a system 200 for generating and monitoring an antimicrobial gas. Platform component elements may be used individually or in combination to implement a system and device to create, maintain, optimize and/or document the presence of a concentration of an antimicrobial agent in a volume under treatment 124.

The system (such as systems 100, 200) is capable of maintaining an antimicrobial agent in the atmosphere of volume under treatment 124, and may include: (1) controlled release of antimicrobials to maintain a target antimicrobial concentration in volume under treatment 124; (2) at least one type of sensor 108, within volume under treatment 124, and possibly several sensors 108 or several types of sensors 108, are used to sense the concentration of the antimicrobial; (3) a computational system 106 that can compare the measured difference between the antimicrobial concentration sensing and a target antimicrobial concentration in volume under treatment 124; (4) an antimicrobial generator 110 (which may be connected to computational system 106) capable of initial establishment and maintenance of a target antimicrobial concentration in volume under treatment 124; (5) where a computed difference between a target antimicrobial concentration and a sensed antimicrobial concentration is determined, a target control may adjust antimicrobial generation to maintain the target antimicrobial concentration; (6) at least one base safety assurance implementation at the physical components of system 100, 200, electronic hardware, and firmware to software levels of the product.

System 100, 200 may be designed for modes of operation to prevent transmission or infection between humans in occupied spaces, as well as modes of operation wherein unoccupied rooms can be treated. To maintain target antimicrobial concentrations, system 100, 200 may separate the durable reusable components from disposable components to maintain refill and physical-digital control across deployed system elements.

Regarding the antimicrobials, the self-degradation kinetics and kinetics of inactivation to log-kill microbes may depend upon more than just the concentration of the antimicrobials in the volume under treatment 124. Thus, system 100, 200 may include a broad spectrum of environment sensing to enable system 100, 200 to use machine learning and artificial intelligence, including for example, enhanced target control, automated volume estimation, humidity measurement, and programmatic antimicrobial cycles.

Antimicrobial generator 110 designs may use matter displacement (including positive displacement pumps) to activate systems, many of which may have an electronic signal that can be harvested to enable enhanced safety assurance utilizing signals collected by a microprocessor/microcontroller 104 that may be part of computational system 106.

System 100, 200 may use external communication 102 to form a connectivity network designed to utilize distributed system data of the aforementioned variables of interest to enable the network coordination of distributed product nodes, and the correspondingly required strategy of spatial and temporal identification constants durably and/or variably assigned to system 100, 200 products.

System 100, 200 may use a combination of platform components, to create an antimicrobial dashboard system. System 100, 200 may provide real-time as well as historical data on infection control, either for safety and health in a user's own spaces, or in high requirements markets such as healthcare facilities. The antimicrobial dashboard system may be used to map a data lake of environment sensing, target antimicrobial concentrations, and use of the connectivity network to deliver distributed system data on the distributed product nodes, which may be identified by unique spatial and temporal identifications, and combine all of this data into human-meaningful information.

Distributing the intelligence (e.g., computational system 106), sensing (e.g., sensor 108), and generation (e.g., antimicrobial generator 110) may enable the development of a digital twin of space for antimicrobial control. This concept may enable additional network safety assurance implementations and may contain all of the information required to develop and deploy proactive strategies in system 100, 200 products such as a predictive antimicrobial control.

System 100, 200 includes the ability to combine platform components in multiple ways to achieve product implementation options that are designed specifically for rooms in buildings and provide digital control to low-concentration of an airborne antimicrobial. This antimicrobial may be used to fight transmission and infection caused by microbe-emitting beings and microbes that are circulated through the air currents in rooms, adjacent rooms via open infiltration/exfiltration passages, and shared HVAC systems.

As illustrated in FIGS. 1A-1C, system 100 may include platform components including external communications 102 devices, microprocessors/microcontrollers 104, computational system 106, antimicrobial and/or environmental sensors 108, and antimicrobial generator 110. System 100 may be entirely contained inside of volume under treatment 124. Optionally, system 100 may be contained within volume under treatment 124 and supplemented with one or more additional sensor sub-systems 120 configured to provide additional data, including antimicrobial concentration and/or environmental data.

As illustrated in FIGS. 2A-2E, system 200 may include both a sensor sub-system 120 and a generation sub-system 122. Sensor sub-system 120 may include external communication 102 devices, a microprocessor/microcontroller 104A, computational system 106, and antimicrobial and/or environmental sensors 108. Generation sub-system 122 may include external communication 102 devices, a microprocessor/microcontroller 104B, and antimicrobial generator 110. System 200 may be entirely contained inside of volume under treatment 124.

Figure 2C:
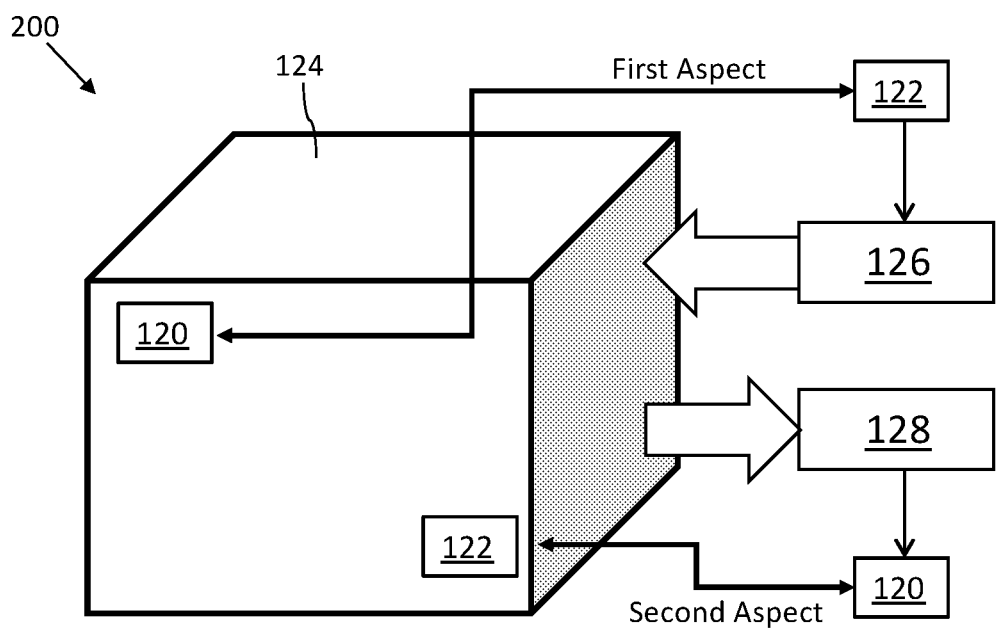
FIG. 2C illustrates a schematic of sensing sub-system 120 and generation sub-system 122 used in conjunction with an HVAC system.

As illustrated in FIG. 2C, system 200 may, in a first aspect, include sensor sub-system 120 within volume under treatment 124, and generation sub-system 122 outside of volume under treatment 124. In the first aspect, generation sub-system 122 generates an antimicrobial and via a fluid connection to an HVAC air supply 126, directs antimicrobial into the interior of volume under treatment 124. The concentration of antimicrobial within volume under treatment 124 is sensed by sensor sub-system 120.

As illustrated in FIG. 2C, system 200 may, in a second aspect, include generation sub-system 122 within volume under treatment 124, and sensor sub-system 120 outside of volume under treatment 124. In the second aspect, generation sub-system 122 generates an antimicrobial within volume under treatment, and via a fluid connection to an HVAC air return 128, sensor sub-system 120 senses the concentration of antimicrobial within volume under treatment 124.

Figure 2D:
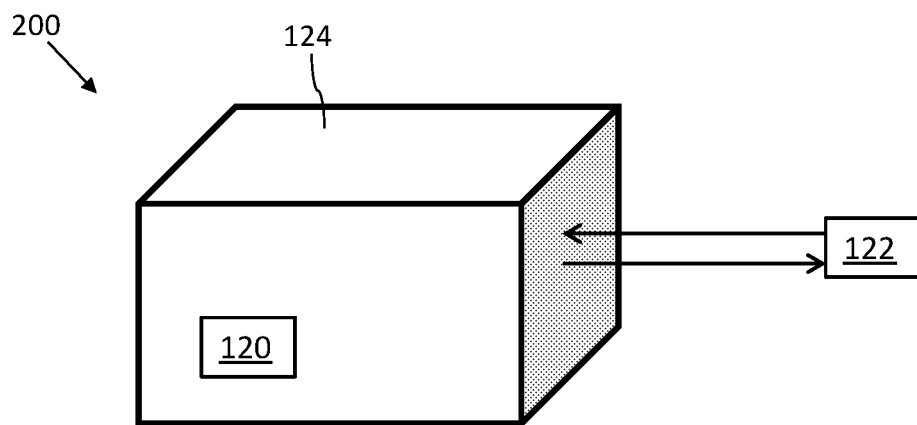
FIG. 2D illustrates a schematic of sensing sub-system 120 within a volume under treatment 124 engaging with generation sub-system 122 outside of the volume under treatment 124.

As illustrated in FIG. 2D, system 200 may include a sensor sub-system 120 within volume under treatment 124, and generation sub-system 122 outside of volume under treatment 124, wherein generation sub-system 122 is in fluid communication within volume under treatment 124 to place generated antimicrobial within volume under treatment 124.

Figure 2E:
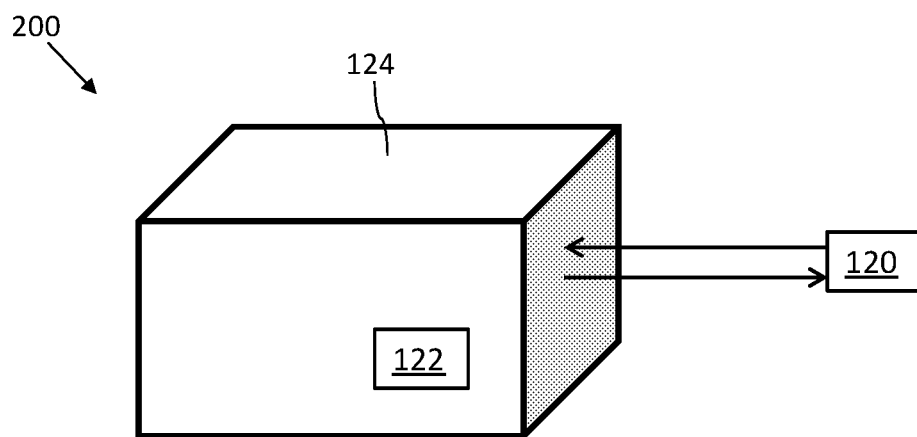
FIG. 2E illustrates a schematic of generation sub-system 122 within a volume under treatment 124 engaging with sensing sub-system 120 outside of the volume under treatment 124.

As illustrated in FIG. 2E, system 200 may include a sensor sub-system 120 outside of volume under treatment 124, and generation sub-system 122 within volume under treatment 124, wherein sensor sub-system 120 is in fluid communication within volume under treatment 124 to sense generated antimicrobial concentrations within volume under treatment 124.

Volume under treatment 124 is conceptually a volume in which a user seeks to distribute an antimicrobial. The volume may be sealed permanently or temporarily to isolate the volume for a period of time. The volume may have openings through which atmosphere can be allowed to infiltrate and/or exfiltrate before, during, or after distributing an antimicrobial. The infiltration/exfiltration can be a characteristic of the volume that is either an uncontrolled variable due to consequence of the volume configuration, or active control strategies of infiltration/exfiltration of atmosphere.

The target volumes may be the living spaces where human beings gather for work, activities, entertainment, and/or their domiciles. Therefore, product targets may be volumes that can be termed rooms, with groups of rooms forming floorplans, collections of floorplans that form a building, and collections of buildings that comprise a facility.

Modular platform components may be extended into other volumes under treatment 124, including for example: (1) mobile vehicles such as the interiors of cars, trains, subways, airplanes, recreational vehicles, ride share vehicles, autonomous vehicles, cabins in ships, and the like; (2) leisure spaces such as restaurants, nightclubs, bars, churches, community centers, libraries, and the like; (3) hospital spaces such as hospital rooms, operating rooms, procedure rooms, patient examination rooms, vivariums, morgues, and the like; and (4) business spaces such as offices, conference rooms, hallways, cafeterias, coffee and lounge areas, and the like.

Target antimicrobial concentrations may be a setpoint desired for antimicrobial release into a volume under treatment 124. The concentration of an antimicrobial in the air can be expressed in relative ratios such as percentages, parts-per-million ("ppm"), or parts-per-billion ("ppb"), and similar terms. As the term is used herein, ppm and ppb are based upon volume.

International standard terms are often used to describe antimicrobial concentrations similar to how industrial chemicals are regulated. Important to system 100, 200 product designs is to treat the air in rooms where people live, work, and play. Regulatory terminology for antimicrobial concentrations in the air in volume under treatment 124 include: (1) recommended/permitted exposure limit, abbreviated "REL/PEL," are concentration and time exposure limits safe for human occupation based upon historical studies and evidence; (2) immediately dangerous to life or health, abbreviated "IDLH," is a concentration at which human exposure can begin to quickly cause an adverse reaction; (3) lethal concentration with 50% mortality, abbreviated "LC-50," is a concentration at which a time-based exposure to an airborne concentration shown to have a mortality rate of 50% in animals exposed in a trial of time at concentration; and (4) lethal dose with 50% mortality, abbreviated "LD-50," is an immediate dose extrapolated from animal trials where a mortality rate of 50% is observed from a single large dose, including air measured as near-immediate mortality at an airborne concentration.

The first target antimicrobial concentrations include:
(1) prevention mode in occupied volumes: simple target number typically predicated upon, but not necessarily constrained to, known and published REL/PEL from regulatory bodies. The objective of the prevention mode is to maintain a known-safe concentration of an antimicrobial in the air in which humans can occupy for a meaningful length of time, typically defined by safety regulators in the context of a "work shift" between 8 to 10 hours. The objective of the concentration is to limit and/or eliminate the transmission potential and/or infection potential of microbes that are already present in a room, or are being emitted into the room by other living beings or room systems like HVAC;
(2) decontamination mode in unoccupied volumes: simple target number typically predicated on, but not necessarily constrained to, known and published IDLH from regulatory bodies. One objective of decontamination mode is to enable the use of higher concentration levels of an airborne antimicrobial that can shorten the time required to inactivate/kill microbes that need elimination faster, are more difficult to kill organisms (such as spores) or are typically easier to kill but that are partially protected in nutrient rich soils, fluids in obvious to hidden locations, and are suspected or confirmed in a specific volume under treatment 124. Targeting the range near to or below the IDLH includes a likelihood that a person who accidently or purposefully walks into volume under treatment 124 will notice effects associated with the IDLH such as watery eyes, nasal irritation, and other immediately dangerous but not lethal concentrations;
(3) emergency decontamination volumes: target number potentially selected where a highly dangerous concentration of and/or highly resistant species of microbe require an emergency decontamination of volume under treatment 124. Once volume under treatment 124 is isolated and evacuated, system 100, 200 products could be set by authorized users to perform higher concentration "civil defense mode" concentrations that are at or exceed the LC-50 and LD-50, therefore requiring a degree of user interaction and implementing physical safety safeguards that such a mode will not be an automated mode.

Sensors 108 and sensor sub-system 120 can include a broad range of sensing technologies to determine the concentration of the antimicrobial in volume under treatment 124.

Any one or a combination of these sensing technologies may be utilized for many different species of antimicrobials, including for example $ClO_2$, which is part of the class of oxidizing antimicrobials, which may additionally include: hydrogen peroxide, dry hydrogen peroxide, ozone, nitric oxide.

System 100, 200 may incorporate any combination of the following sensors 108 to achieve digital control: (1) electrochemical sensors that utilize a depletable chemical which reacts with the antimicrobial, and an electrical circuit that measures the effect of this chemical reaction using measures of charge, voltage, current, conductivity, resistivity, and the like to provide a signal that is in proportion to the known capable range of the sensors. An example of electrochemical sensors for $ClO_2$ include sensors from Analytical Technologies, Inc.; (2) MOx sensors (metal oxide semiconductor sensors) are widely used in air quality measurement, typically for airborne pollutants such as H2S, volatile organic compounds, and are known to work to sense gaseous oxidizing species. Two examples of these MOx sensors include the Sensirion SGP40 and the Renesas ZMOD4410 family of sensors.

Advantages of MOx sensors over electrochemical sensors may include: (a) 10-year lifetimes with no chemicals to deplete; (b) calibration and training values last the lifetime of the sensor; (c) sensors can be "trained" to gas species of interest. The number of gases the sensor can be trained to is not limited by choices of chemical species in the sensor, therefore, as opposed to electrochemical sensors, one MOx sensor can be used to sense multiple antimicrobial species of interest, as well and complementary and potentially interfering gases, without requiring use of different chemicals, membranes, or other interaction/barrier methods to provide species specificity.

Alternative sensing solutions may be able to sense an antimicrobial species to the parts-per-billion to parts-per-trillion levels of concentration expected in the prevention mode in occupied volumes. These alternatives may include: (1) Colorimetry: using a chemical "dye" that interacts with the antimicrobial species of interest and causes a reaction that can be observed be electronic color sensors. The "color" can be in the spectrum of visible, infrared, UV, and other wavelengths of light. The fundamental output of such a system would be an electronic signal that is proportional to the "color change" expected for known chemical interactions that underpin such sensing technologies; (2) Fluorescence: if the antimicrobial species fluoresces, or can be bound to a chemical species that is selective and can be sensed via fluorescence, the magnitude of the fluorescence can be sensed and calibrated to known sources to translate fluorescence levels sensed into and electronic signal that is proportional to said fluorescence.

Electronic and/or computational controls (computational system 106) act as the "heart" and "brains" of a system 100, 200 product. While there are electronic analog, field-programmable gate array ("FPGA"), and discrete circuitry methods that may work for control, the digital solutions designed for low power battery-powered connected products are particularly beneficial for wireless system 100, 200 products.

Microprocessors or microcontrollers 104 may form the control intelligence backbone of system 100, 200 products. Microprocessors may be used as these may be required for the embodiments of certain simple safety assurance systems.

Microprocessor unit 104 may be the central processing core electrically connected to all of the elements of the system 100, 200 platform components.

Antimicrobial generator 110 is any of a variety of sub-components responsible for the generation and/or dispersion of an antimicrobial into volume under treatment 124. A large variety of antimicrobial generators 110 is discussed herein, including:

(1) compressed matter release: an antimicrobial stored in a compressed state is released by a pressure reducing regulator. For example, a canister of antimicrobial gas connected to a pressure reducing regulator, which when opened, allows compressed antimicrobial gas to flow out of the canister to an uncompressed state. A mass flow controller in the path of the matter being transformed from a compressed to an uncompressed state can provide quantitative measurement of the quantity of antimicrobial released;

(2) two or more chemical activation: two or more precursors are combined to cause a chemical reaction that generates the desired antimicrobial. The two or more precursors can be mixed in passive or active structures, including microfluidic structures to accelerate reaction kinetics. Examples of systems contained herein utilizing this concept include, without limitation: reactors 1800, 1900, 2000, 2100, and 2200; gas generators 2300, 2400, and 3000; gas reactor 2800; antimicrobial generators 3100 and 3200; and aerosol containers 3486 and 3586;

(3) electrochemical activation: voltage potential and/or current can be varied to control species release and kinetics of antimicrobial generation. In one aspect, termed a flow-through electrochemical cell, $NaClO_2$ can be flowed over electrodes and recycled until depleted by the electrochemical cleaving of Na from $NaClO_2$. In another aspect, the precursor material can be contained in a static volume into which electrodes are co-located to generate the electrochemical cleaving of Na from $NaClO_2$ until the bulk fluid is depleted. In another aspect, $ClO_2$ is electrochemically generated from a solution of $NaClO_2$ as the anolyte that is separated from a catholyte by a membrane. Each anolyte and catholyte is in communication with at least one electrode, and a membrane plays an active role in increasing the yield or desired species of antimicrobial (e.g., $ClO_2$) while sequestering undesired species in the catholyte like Na (in this example for $ClO_2$). In another aspect, a thin layer of sodium chlorite is flowed in a closed, open, or one-sided membrane channel where material could be introduced to an electrochemical cell designed to generate $ClO_2$ only from the small quantity of $NaClO_2$, after which the depleted precursor is transferred to a waste container and the processed is repeated.

Systems 100, 200 may be a platform that includes durable reusable components and disposable components. The disposable components may include refill cartridges. The refill cartridges may include precursors or direct antimicrobial in a concentrated form. Refill cartridges may include a reservoir. Refill cartridges may include platform components that are prone to failure from wear, including for example, pumps, sensors, and the like.

Systems 100, 200 may include digital and physical signals to achieve the changing of modes as described above. System 100, 200 may be used either in occupied or unoccupied volumes under treatment 124.

As such, one class of refill cartridges can incorporate a mechanism (physical, electrical/digital, or both) to limit the base unit into which it is installed to operate in an occupied volume under treatment 124 mode (e.g., prevention mode in occupied volumes) and REL/PEL concentration levels.

Another class of refill cartridges can incorporate a mechanism (physical, electrical/digital, or both) to allow the base unit into which it is installed to operate in a decontamination mode (e.g., decontamination mode in unoccupied volumes). Additional features may include a mechanism limiting installation to a subset of users who are authorized to install the decontamination mode cartridge. These features may include a requirement to enter an appropriate electronic or digital authorization (e.g., a code, swipe a keycard, enter a biometric pass, or the like) to unlock a decontamination mode that would be inappropriate for occupied spaces. Such a decontamination mode may utilize IDLH or higher concentration levels and may be suitable for regular or exceptional "deep-clean" scenarios.

System 100, 200 may use a combination of platform components, to create an antimicrobial dashboard system. The dashboard system may combine distributed intelligence, distributed data across the system, and other platform components to enable beneficial system features, including for example: (1) a room, floor, building control dashboard for antimicrobial treatment; (2) provide notifications to phones that are nearby a base unit; (3) system 100, 200 coordination in physically adjacent volumes under treatment 124; (4) antimicrobial output coordination of multiple units in a single contiguous volume (e.g., a large open space such as a concert hall); (5) data portability for integration into building management systems, such as hospital command centers; and (6) civil defense alert network for biological threats or attacks.

Each system 100, 200 unit may securely connect (IoT connections), for purposes of data collection and storage, software and firmware updates, and/or user interactions, to assign: (1) unique identifiers for each hardware unit; (2) unique identifiers for each refill unit; (3) and/or two different types of refill units (one for when in low-concentration occupied mode, and another for authorized user to change to unoccupied decontamination mode).

Additionally, each system 100, 200 unit may securely connect to each other (via external communication 102) and may pass identification validation data as well as recorded operational performance data along to a data gathering point. Each unit may record its own data, and if necessary for redundancy and safety, neighboring unit data. In one aspect, each unit may connect to a WiFi hub to achieve interconnectivity. In another aspect, all units may be required to connect to a central identification validation and data gathering point.

Computational system 106 may include local storage mediums for each system 100, 200 unit. Alternatively, one unit can have storage capability and may act as an accumulator for multiple units in a logical grouping. All units or all accumulators may be required to report up into a central data gathering point, which may also be a point of connection into cloud data.

In one aspect, system 100, 200 units may have safety features including: (1) input received from each unit, including location, environmental sensor suite, antimicrobial sensor data, quantity of antimicrobial generated, and/or corresponding time stamps; (2) output to user and/or system controls including possible safety signal generation based upon: (i) operational parameters that do not make sense and thus that particular unit may be malfunctioning, (ii) recognition that a neighboring unit has experienced an error can initiate "alert status" among a local group of units, and a group or region of units could be powered off if airflow-dictated interactions between two local units cause interference, (iii) client and/or host operations control: the control system will watch for signals of parameters that do not make sense, across the entire installation of units.

System 100, 200 may include machine learning algorithms. For example, machine learning algorithms may use a multi-sensor suite to both measure and classify at least two fundamental characteristics of airborne microbial concentration in volume under treatment 124.

System 100, 200 may include the capability to automatically measure the volume of any given volume under treatment 124. Sensor array 108 may be utilized to automatically measure room volume so that generator 110 closed-loop performance can be translated from a concentration in the air to a value of required make up antimicrobial that will move the concentration from a measured value to the target concentration within volume under treatment 124. System 100, 200 units may generate and emit a known test quantity of the antimicrobial upon initialization. The unit may initiate continuous antimicrobial sensor 108 readings while generator 110 is kept idle for a period of time between 1 min to 4 hours. On-unit computation capability measures peak concentration and uses machine learning aspect 1 ("ML1") to measure room kinetics. Understanding that concentration=mass (derived from sensed dispensed antimicrobial volume, directly or indirectly sensed precursor utilization, mass flow measurement of antimicrobial gas, or any other value that can be traced back to quantity) of antimicrobial divided by volume of volume under treatment 124. The volume of volume under treatment 124 is determined by using the measured quantity of antimicrobial generated and antimicrobial concentration reading at a time appropriate to the room kinetics measured with ML1. System 100, 200 may iterate with each antimicrobial gas emission to update ML1 room kinetics estimates, while cataloging changes by time stamp. As machine learning aspect 2 ("ML2") "learns" from the data lake or direct verification experiments, future algorithms may be designed to provide input data to the generator to predict the specific quantity of antimicrobial needed to achieve the desired concentration based upon environment conditions within volume under treatment 124. Alternatively, or as a backup method, system 100, 200 may use a three-dimensional laser measuring system, or a tone emitter and microphone on units to ping the volume of volume under treatment 124 with a CHIRP acoustic signal. Measuring time of flight and collision of sound waves, system 100, 200 may build a characteristic volume estimate of volume under treatment 124.

Figure 3:
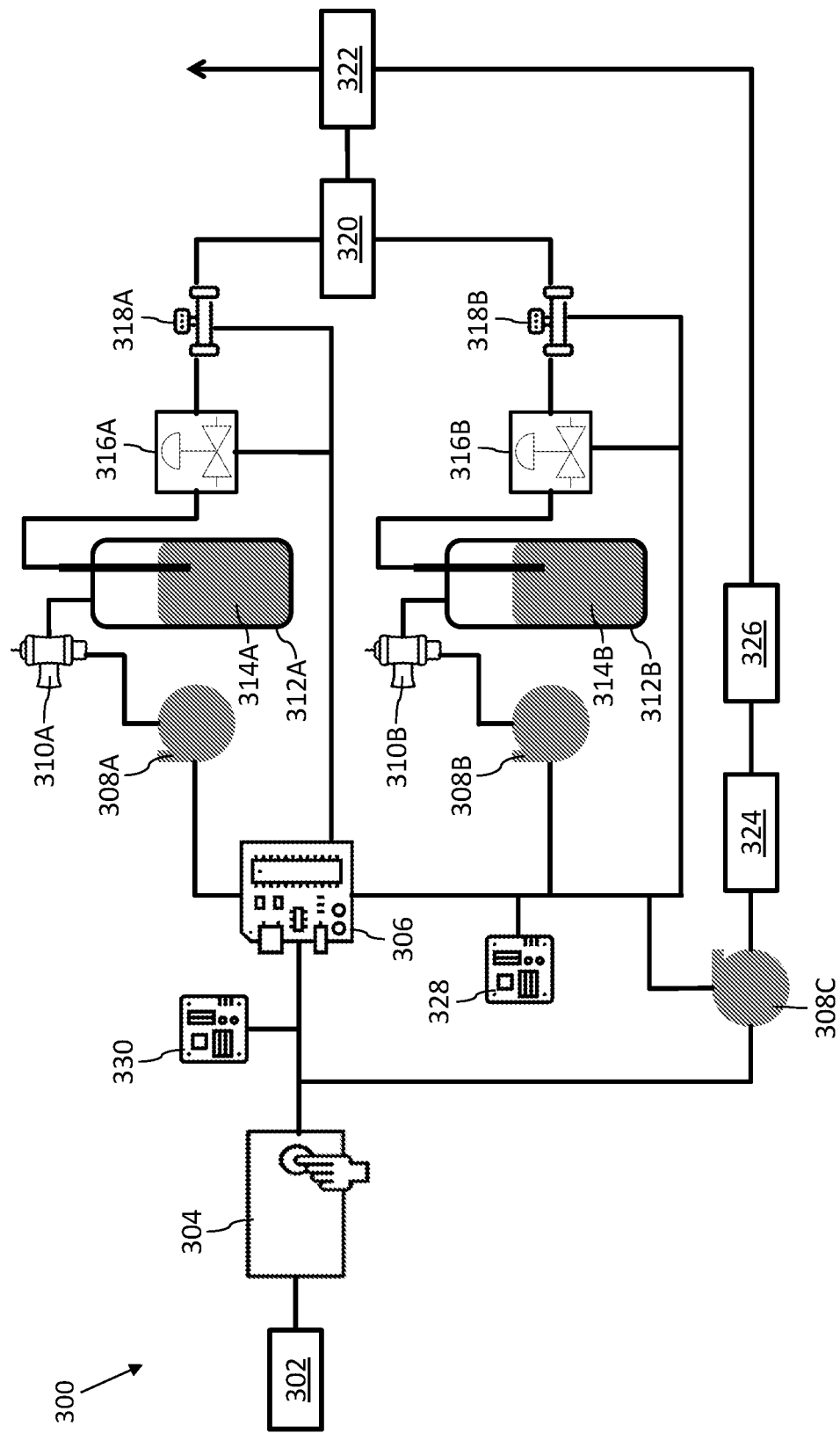
FIG. 3 illustrates a schematic of an example system 300 for generating and monitoring an antimicrobial gas.
Figure 4:
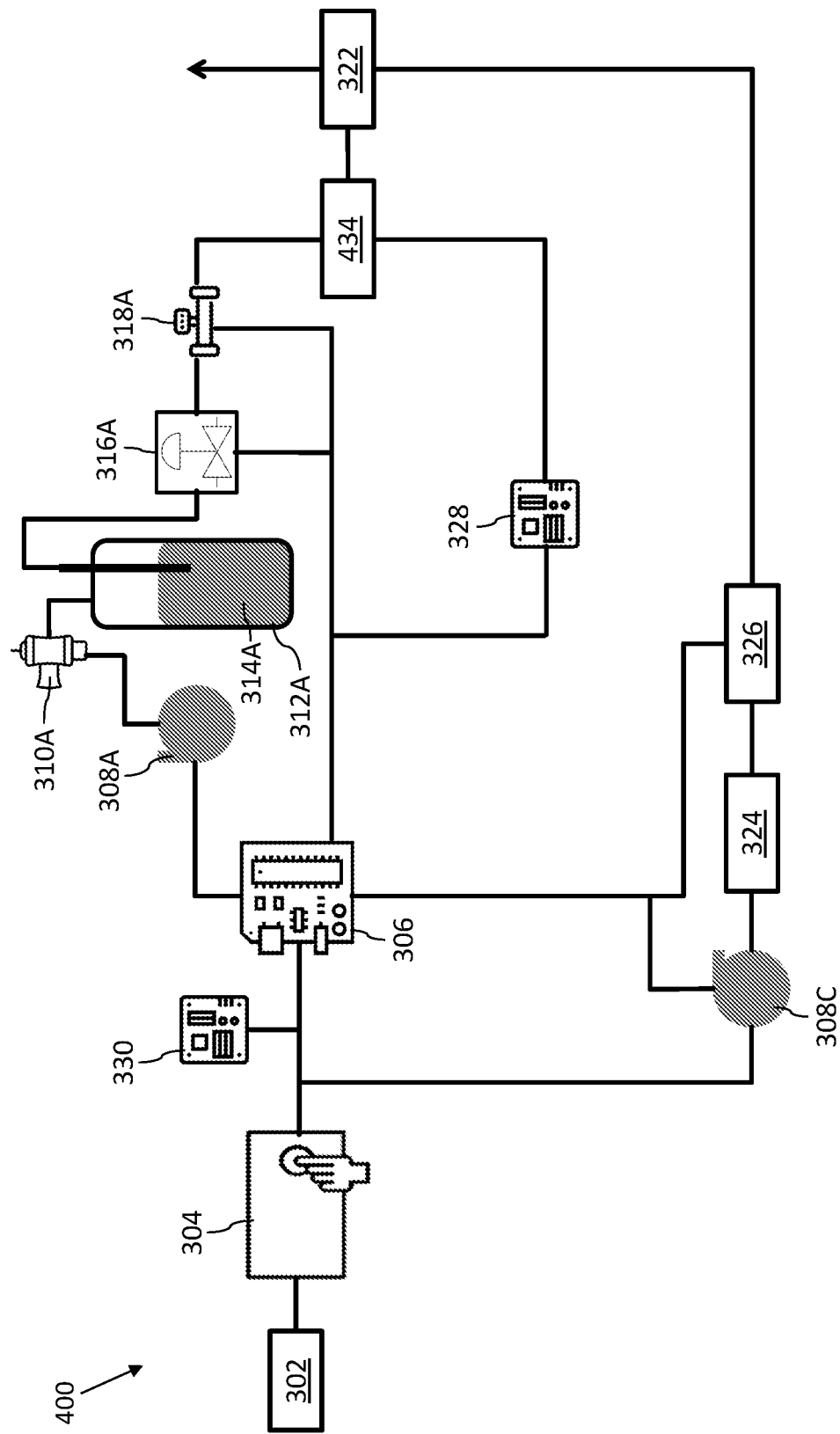
FIG. 4 illustrates a schematic of an example system 400 for generating and monitoring an antimicrobial gas.

FIGS. 3 and 4 illustrate schematics of example systems 300 and 400 for generating and monitoring an antimicrobial gas (including a disinfection gas and/or decontamination gas). The antimicrobial gas may be a $ClO_2$ gas. Systems 300 and 400 may include a microfluidic liquid dispensing and metering system. Systems 300 and 400 may be used to both generate antimicrobial gas (e.g., $ClO_2$ gas) and dispense the antimicrobial gas (e.g., $ClO_2$ gas) to the ambient environment, and to sample the ambient air to identify antimicrobial gas concentration therein and generate more or less antimicrobial gas as necessary to maintain a desired antimicrobial gas concentration. Systems 300 and 400 may be used to test air in a particular environment (e.g., a three-dimensional enclosed space) to determine the concentration of antimicrobial gas (e.g., $ClO_2$ gas) in parts per billion ("ppb") of air. Systems 300 and 400 may be used to maintain a desired antimicrobial gas concentration in ambient air surrounding devices housing systems 300 and 400 by regularly sampling the ambient air, determining the concentration of antimicrobial gas in the ambient air, and via closed-loop control of the device, generating more or less antimicrobial gas to maintain the desired antimicrobial gas concentration in the ambient air.

Systems 300 and 400 may include wired connections to a computer network, cloud storage, or the like. Systems 300 and 400 may include wireless connections to a computer network, cloud storage, or the like. Systems 300 and 400 may document time-based tracking of system use, product maintenance, target concentration performance, and environmental parameters of interest. This documentation may be in the form of files, logs, or other records stored locally within a device housing system 300 and/or 400 or transmitted via wired connection or wirelessly to a computer network, cloud storage, or the like. Systems 300 and 400 may have cloud and/or IoT connectivity to enable user personas to effectively set up, train, manage, and maintain devices housing systems 300 and/or 400 in the three-dimensional enclosed spaces under treatment, view real-time and stored performance and environment data, and/or export data to compare validation tests such as animal and human exposure trials.

Systems 300 and 400 may be used to decontaminate (that is, to inactivate or destroy pathogens) a three-dimensional enclosed space (e.g., a hospital room) through high concentrations of antimicrobial gas (e.g., $ClO_2$ gas) (when unoccupied by humans), or through low concentrations of antimicrobial gas (e.g., $ClO_2$ gas) (when occupied by humans). In one aspect, systems 300 and 400 generate antimicrobial gas in a concentration of 1,000 ppb to 5,000 ppb or 50,000 to 300,000 ppb to decontaminate an unoccupied three-dimensional enclosed space. Systems 300 and 400 may destroy the COVID-19 within a three-dimensional enclosed space.

Systems 300 and 400 may be used to prevent the spread and/or survival of a virus in a three-dimensional enclosed space (e.g., a hospital room) through low concentrations of antimicrobial gas (e.g., $ClO_2$ gas) (whether occupied by humans or not). In one aspect, systems 300 and 400 generate antimicrobial gas in a concentration of less than 100 ppb, for example 50 ppb, to prevent the spread and/or survival of a virus in an occupied three-dimensional enclosed space. Systems 300 and 400 may reduce aerosolized virus transmission and infection of viruses including COVID-19. Systems 300 and 400 may inactivate and/or kill airborne pathogens, and even protect against airborne contagions.

System 300 and/or 400 may be contained within a device housing 304. Ambient air 302 may enter one or more inlet in device housing 304. Ambient air 302 may pass through a particulate filter within device housing 304. The particulate filter may not exclude any atmospheric molecules.

Ambient air 302 passes from device housing 304 into one or all of air pumps 308A, 308B, and 308C via one or more air ducts. System 300 includes air pumps 308A, 308B, and 308C, while system 400 only includes air pumps 308A and 308C, as will be further explained below.

A microcontroller 306 may control all on-board functions of system 300 and 400. Microcontroller 306 includes software that can be written to change system 300 and 400's functions where necessary. Microcontroller 306 is operatively connected to various elements (described further below) of systems 300 and 400 via wired or wireless connection.

Microcontroller 306 is connected to air pumps 308A, 308B, and 308C as illustrated, and controls the function of 308A, 308B, and 308C, including one or more of start, stop, velocity, flow rate, pressure, and the like. Air pumps 308A, 308B, and 308C may be disc pumps. In one aspect, air pumps 308A, 308B, and 308C may be capable of producing pressure in excess of 270 mbar, flow rates in excess of 0.55 L/min, and vacuum in excess of 220 mbar. Air pumps 308A, 308B, and 308C may include separate motor control units. Air pumps 308A, 308B, and 308C may include integrated motor control units. It is understood that system 400 does not include air pump 308B.

Figure 6:
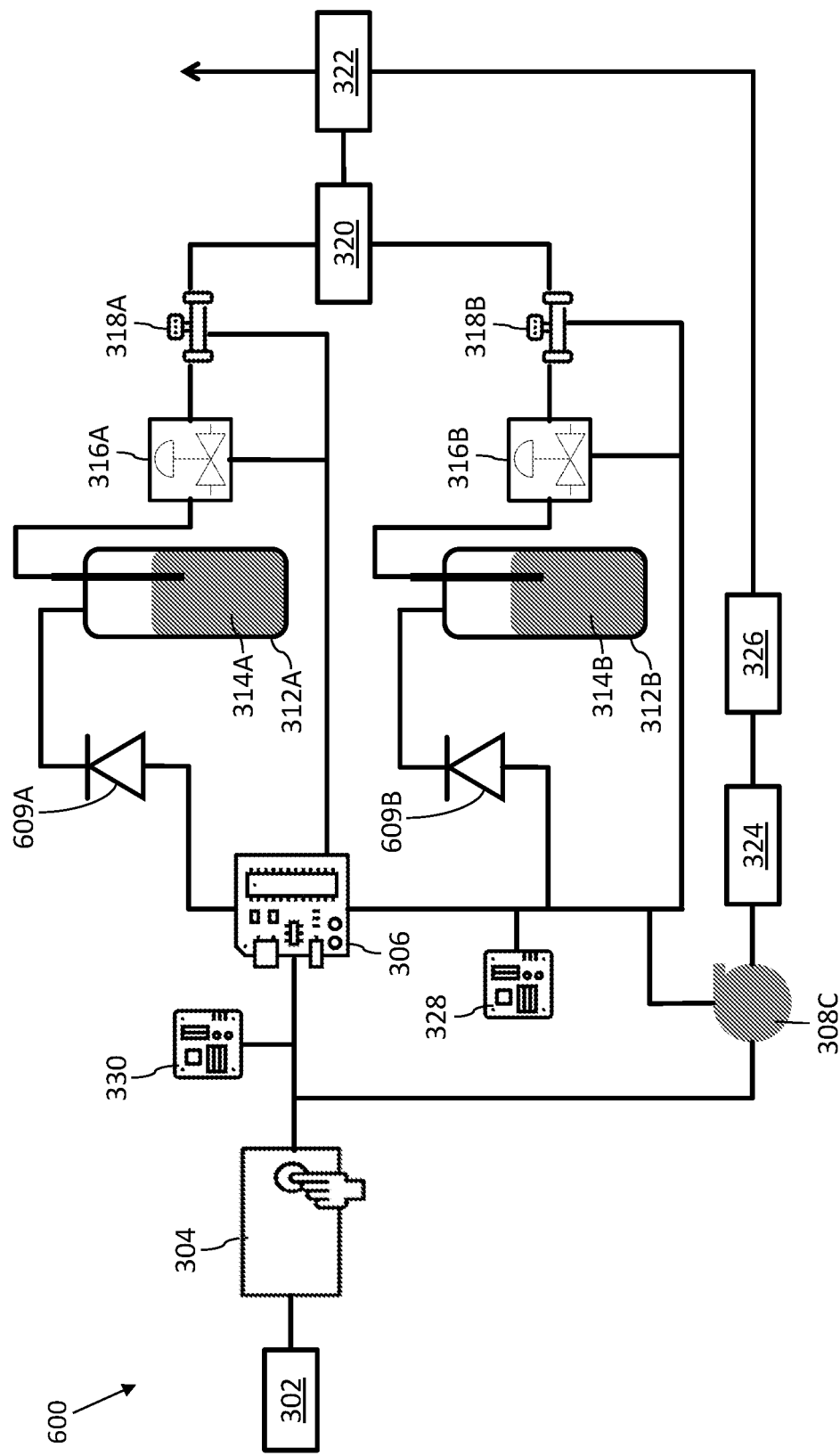
FIG. 6 illustrates a schematic of an example system 600 for generating and monitoring an antimicrobial gas.
Figure 7:
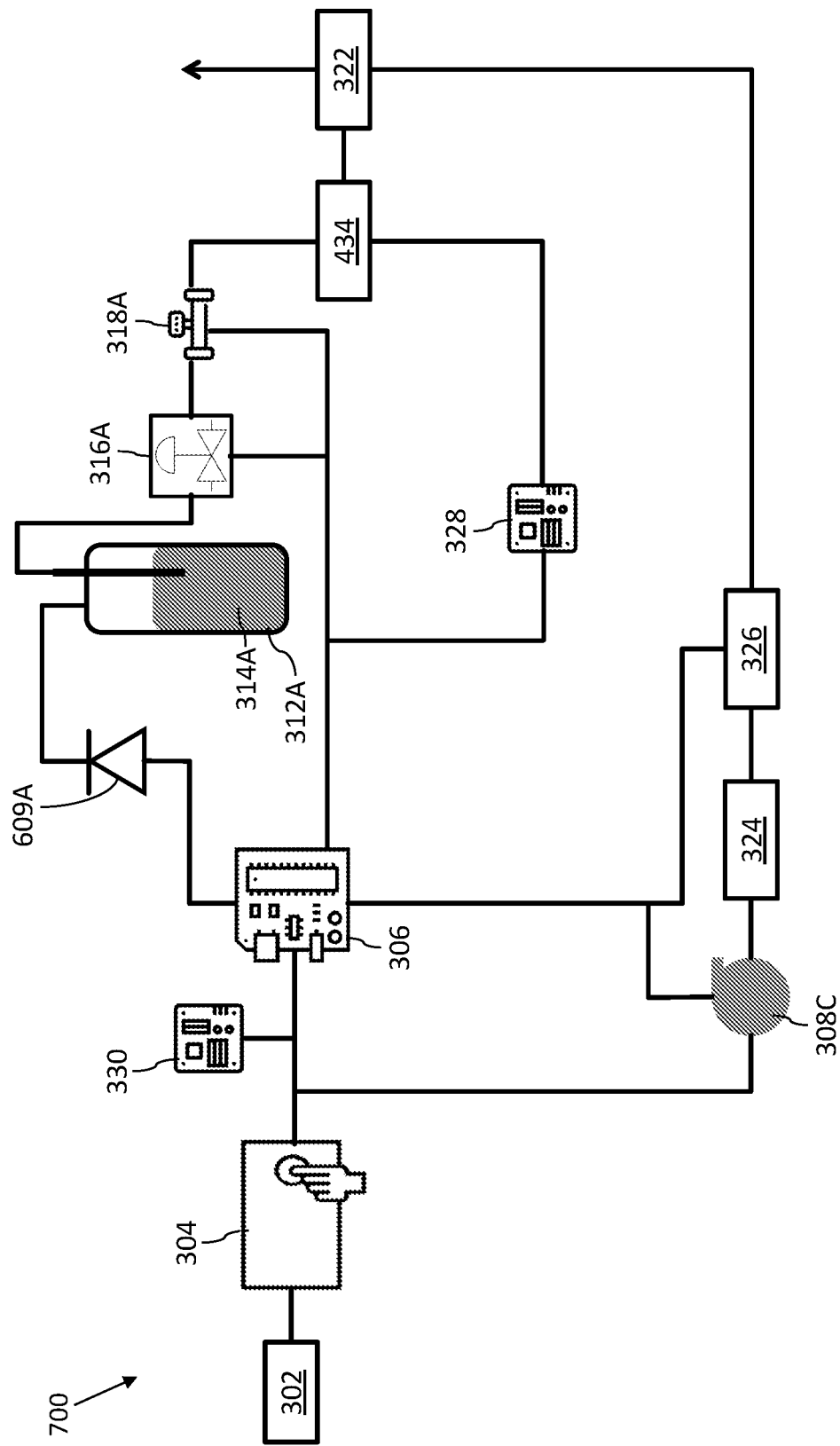
FIG. 7 illustrates a schematic of an example system 700 for generating and monitoring an antimicrobial gas.

Air pumps 308A and 308B in system 300 are connected to pressure relief valves 310A and 310B, such that excess or unnecessary pressure produced by air pumps 308A and 308B may be routed out of system 300. System 400 likewise includes a pressure relief valve 310A having the same function but does not include a pressure relief valve 310B. Alternatively, as illustrated in FIGS. 6 and 7, systems 600 and 700 eliminate at least air pumps 308A and 308B as reagent containers 312A and 312B may be pressurized prior to assembly of systems 600 and 700, and thus air pumps 308A and 308B are unnecessary.

System 300 includes reagent containers 312A and 312B, each containing a different liquid reagent 314A and 314B. Reagents 314A and 314B may be combined within a microfluidic mixer 320 to generate $ClO_2$ gas. One of reagents 314A and 314B may be a liquid precursor such as $NaClO_2$ (sodium chlorite). The other of reagents 314A and 314B may be a liquid activator such as an acid/H+ activator.

With respect to system 300, air pump 308A pressurizes reagent container 312A, thus causing reagent 314A to travel from reagent container 312A, through a passage into an electronically operated normally closed valve 316A (which is connected to a controlled by microcontroller 306). From valve 316A reagent 314A travels through a microfluidic flow sensor 318A (which is used for closed-loop control signals and is connected to and provides data to microcontroller 306), and into microfluidic mixer 320. It is contemplated that any pressure generator may be used in lieu of air pump 308A to pressurize reagent container 312A. In one aspect, reagent container 312A may be pressurized by an external source during assembly of system 300, and a valve connected to reagent container 312A (e.g., valve 316A) may open to permit the passage of a quantity of pressurized reagent to exist reagent container 312A and proceed into microfluidic mixer 320 as described above. Such a system is illustrated in FIG. 6.

With respect to system 300, air pump 308B pressurizes reagent container 312B, thus causing reagent 314B to travel from reagent container 312B, through a passage into an electronically operated normally closed valve 316B (which is connected to and controlled by microcontroller 306). From valve 316B reagent 314B travels through a microfluidic flow sensor 318B (which is used for closed-loop control signals and is connected to and provides data to microcontroller 306), and into microfluidic mixer 320. It is contemplated that any pressure generator may be used in lieu of air pump 308B to pressurize reagent container 312B. In one aspect, reagent container 312B may be pressurized by an external source during assembly of system 300, and a valve connected to reagent container 312B (e.g., valve 316B) may open to permit the passage of a quantity of pressurized reagent to exist reagent container 312B and proceed into microfluidic mixer 320 as described above. Such a system is illustrated in FIG. 6.

Microfluidic mixer 320 may be a planar shape designed for low dead space volume and effective mixing to increase reaction kinetics of precursors.

The mixture of reagents 314A and 314B in microfluidic mixer 320 creates an antimicrobial gas, including for example, $ClO_2$ gas. Antimicrobial gas may pass via a passage into an off-gas and waste chamber 322. Chamber 322 may include an absorber material, an evaporator, or the like. Within chamber 322, any waste from the creation of antimicrobial gas may be absorbed in an absorber material. Chamber 322 may include a membrane. Antimicrobial gas may exit chamber 322 into the ambient atmosphere. In one aspect, antimicrobial gas exits chamber 322 through the membrane. System 300 and 400 may include a device for separation of antimicrobial gas (e.g., $ClO_2$ gas) and post-generator waste in communication with one or more air pumps and air ducts to one or more outlets, and on-device or in-device waste storage prior to disposal. Chamber 322 may act as the device for separation of antimicrobial gas and post-generator waste. Chamber 322 may act as the device for on-device or in-device waste storage prior to disposal. Chamber 322 may act as both the device for separation of antimicrobial gas and post-generator waste and the device for on-device or in-device waste storage prior to disposal.

With respect to system 400, system 400 does not include an air pump 308B, pressure relief valve 310B, reagent container 312B, reagent 314B, valve 316B, or a microfluidic flow sensor 318B. Further, system 400 substitutes microfluidic mixer 320 with a microfluidic electrochemical generator 434. In system 400, air pump 308A pressurizes reagent container 312A, thus causing reagent 314A to travel from reagent container 312A, through a passage into an electronically operated normally closed valve 316A (which is connected to and controlled by microcontroller 306). From valve 316A reagent 314A travels through a microfluidic flow sensor 318A (which is used for closed-loop control signals and is connected to and provides data to microcontroller 306), and into microfluidic electrochemical generator 434. An electrical current, provided by and controlled by microcontroller 306 within microfluidic electrochemical generator 434 causes a reaction with reagent 314A within microfluidic electrochemical generator 434 that produces an antimicrobial gas, such as $ClO_2$ gas. Antimicrobial gas passes from microfluidic electrochemical generator 434 into chamber 322 and ultimately into the ambient environment as described with respect to system 300.

It is contemplated that any pressure generator may be used in lieu of air pump 308A to pressurize reagent container 312A. In one aspect, reagent container 312A may be pressurized by an external source during assembly of system 300, and a valve connected to reagent container 312A (e.g., valve 316A) may open to permit the passage of a quantity of pressurized reagent to exist reagent container 312A and proceed into microfluidic mixer 320 as described above. Such a system is illustrated in FIG. 7.

Electronically operated normally closed valve 316A, 316B may be controlled by microcontroller 306, and may be oriented such that when no power is provided, valve 316A, 316B is closed. Likewise, when power is provided, valve 316A, 316B is open.

Microfluidic flow sensor 318A, 318B may sense the flow of reagent 314A, 314B, respectively, and may provide data regarding that flow to microcontroller 306. Such data may include flow rate, flow volume, flow time, mass, and the like.

Systems 300 and 400 may include a barometric sensor 328. Barometric sensor 328 may sense the pressure within the three-dimensional enclosed space that systems 300 and 400 operate. Upon sensing a negative pressure (indicating that a HVAC return system is pulling air out of the room, a door or window is open, or the like), barometric sensor 328 may communicate the negative pressure via its connection with microcontroller 306, upon which microcontroller 306 may pause antimicrobial gas (e.g., $ClO_2$ gas) generation until a neutral and/or positive pressure is sensed by barometric sensor 328. Upon sensing a neutral or positive pressure, barometric sensor 328 may communicate the neutral or positive pressure to microcontroller 306, at which point microcontroller 306 may once again initiate gas generation (e.g., $ClO_2$ gas).

Systems 300 and 400 may include an air quality sensor 330. Air quality sensor 330 may sense any of a variety of ambient air 302's characteristics, including for example, humidity, temperature, and the like. Data regarding air quality may be recorded for evaluating the effectiveness of systems 300 and 400. Alternatively, as antimicrobial gas (e.g., $ClO_2$ gas) may be more effective at destroying pathogens in more humid environments, humidity data, for example, may be communicated via air quality sensor 330's connection with microcontroller 306, upon which microcontroller 306 may adjust the target concentration of antimicrobial gas in ambient air 302 based upon humidity readings.

The above-described aspects, methods, and processes of systems 300 and 400 demonstrate the generation of antimicrobial gas by each of systems 300 and 400. Below is described the aspects of systems 300 and 400 that sample ambient air 302 to determine the concentration of antimicrobial gas (e.g., $ClO_2$ gas) within ambient air 302.

Figure 8:
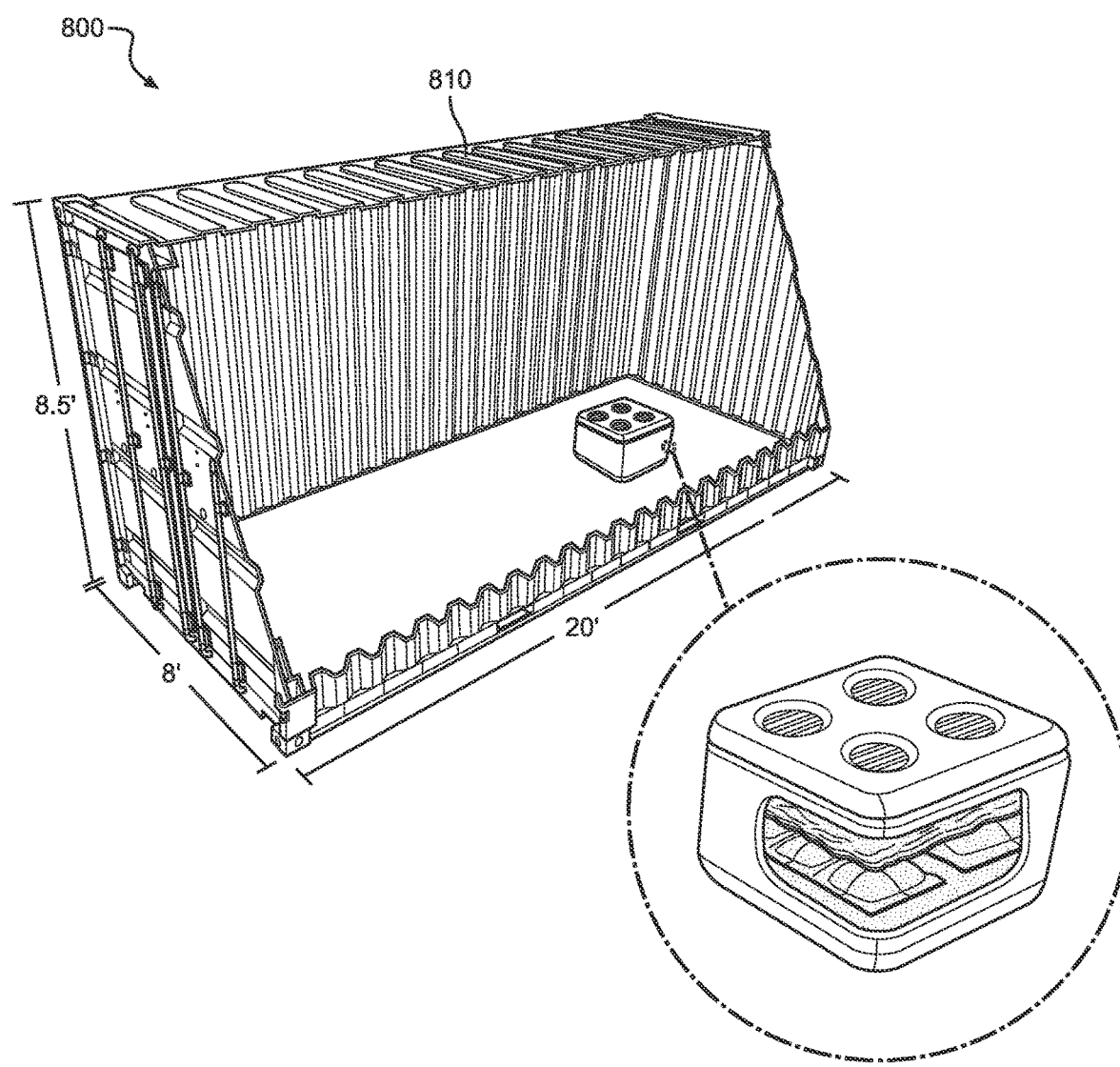
FIG. 8 illustrates a cutaway perspective view of a system 800 generating antimicrobial vapor within a sealed environment 810 for disinfecting items therein.
Figure 9:
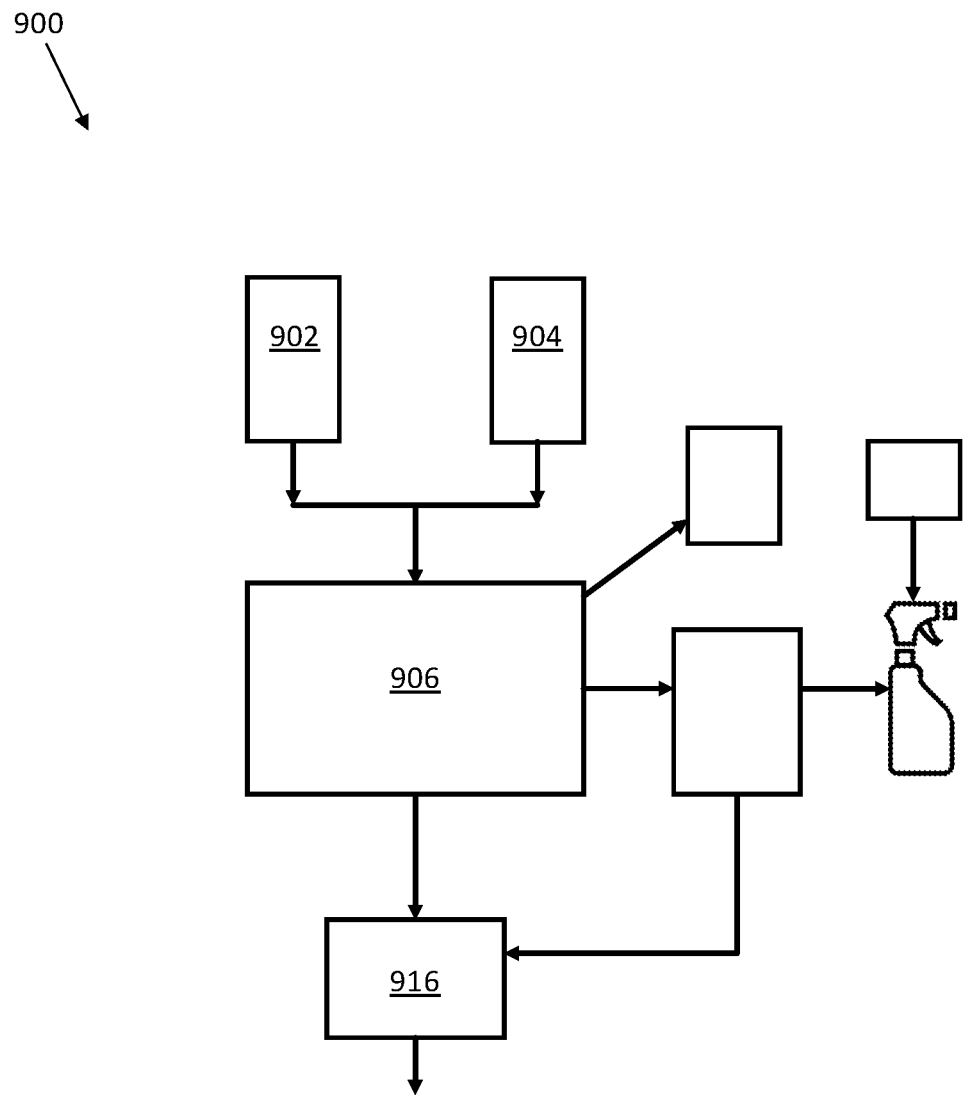
FIG. 9 illustrates a system 900 for generation of an antimicrobial gas and/or solution.
Figure 10:
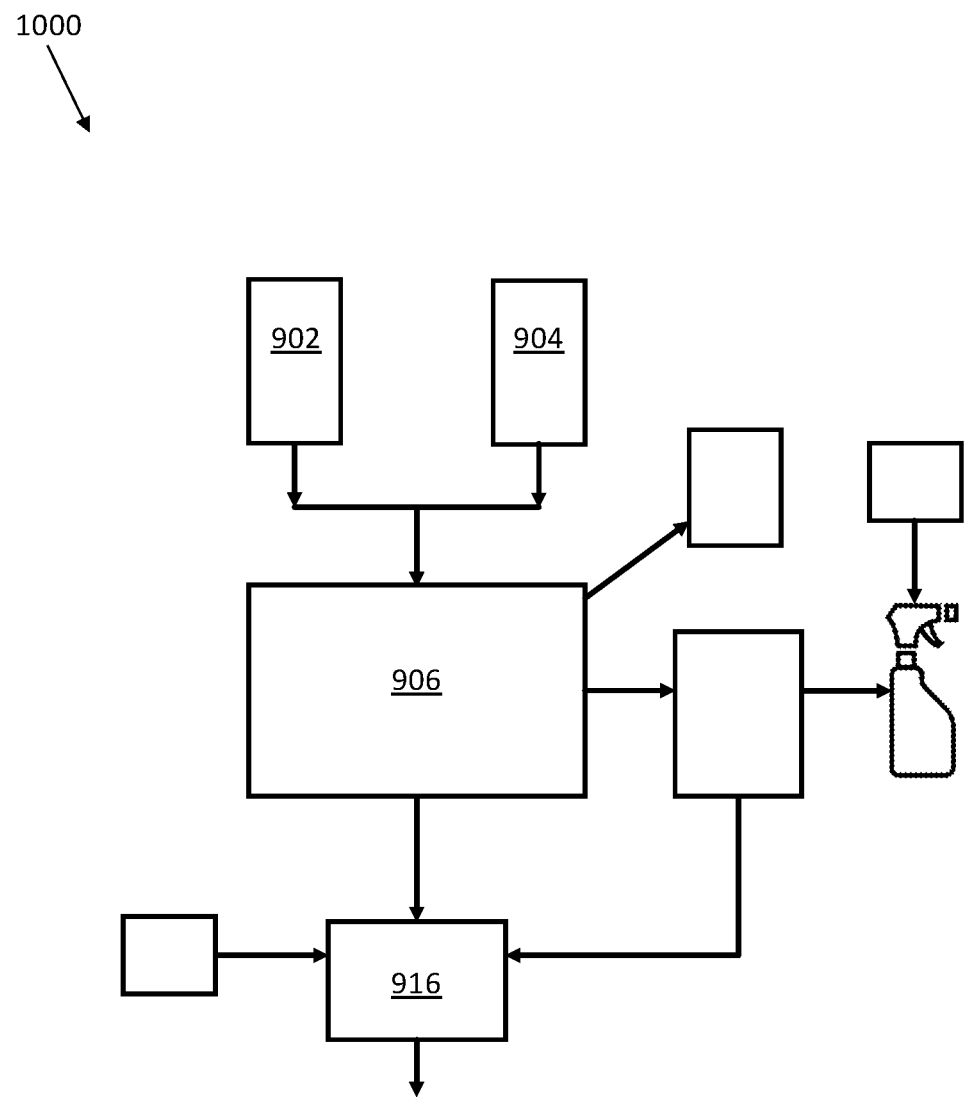
FIG. 10 illustrates a system 1000 for generation of an antimicrobial gas and/or solution.
Figure 11:
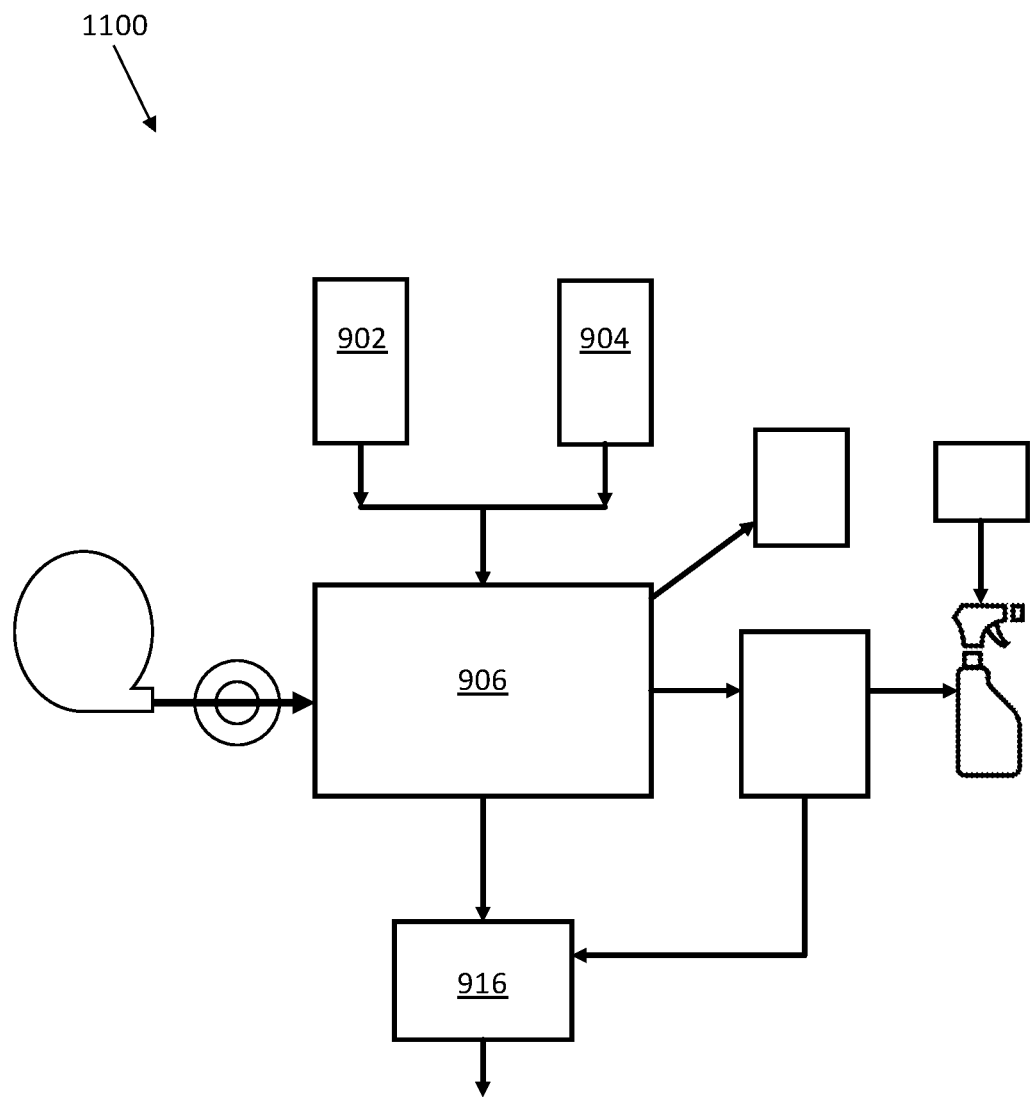
FIG. 11 illustrates a system 1100 for generation of an antimicrobial gas and/or solution.
Figure 12:
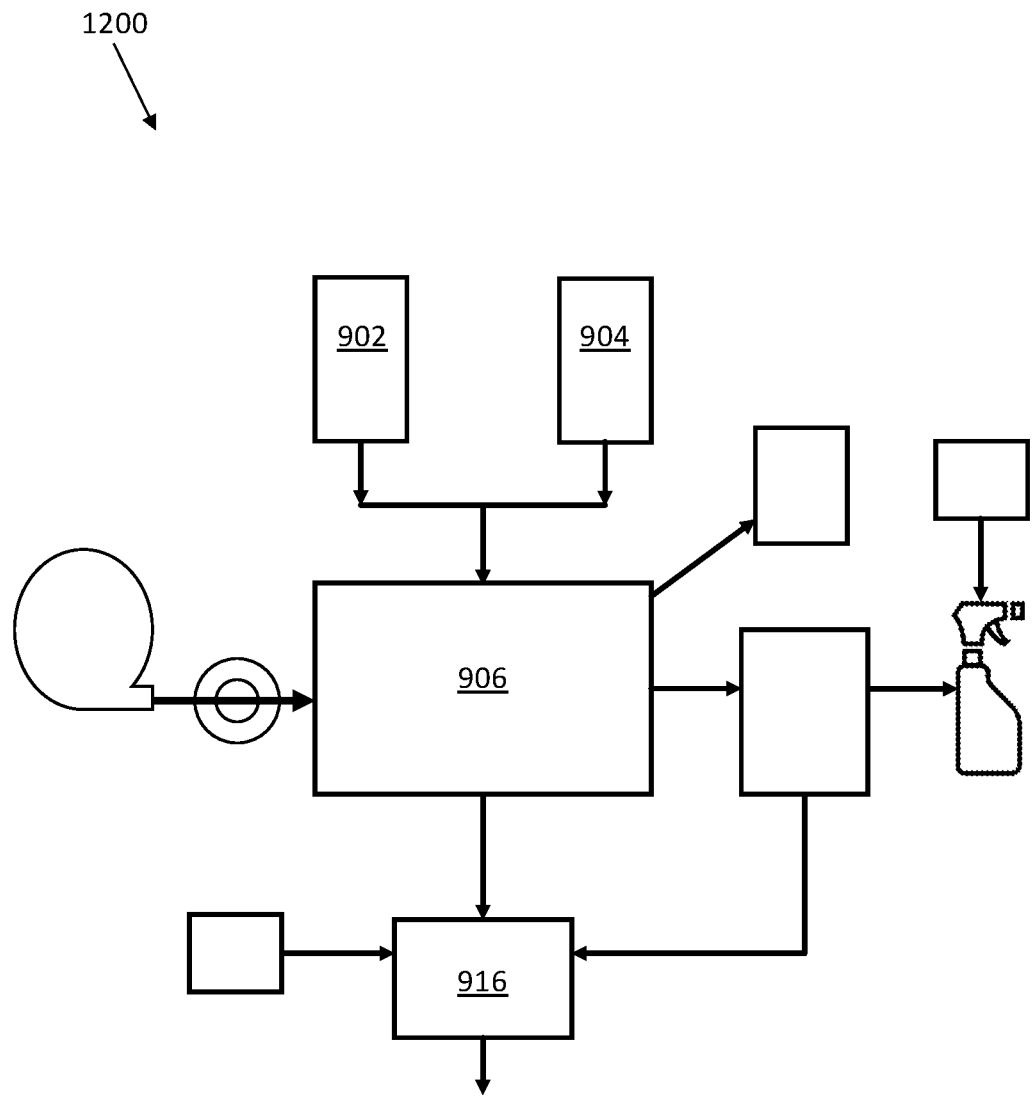
FIG. 12 illustrates a system 1200 for generation of an antimicrobial gas and/or solution.
Figure 13:
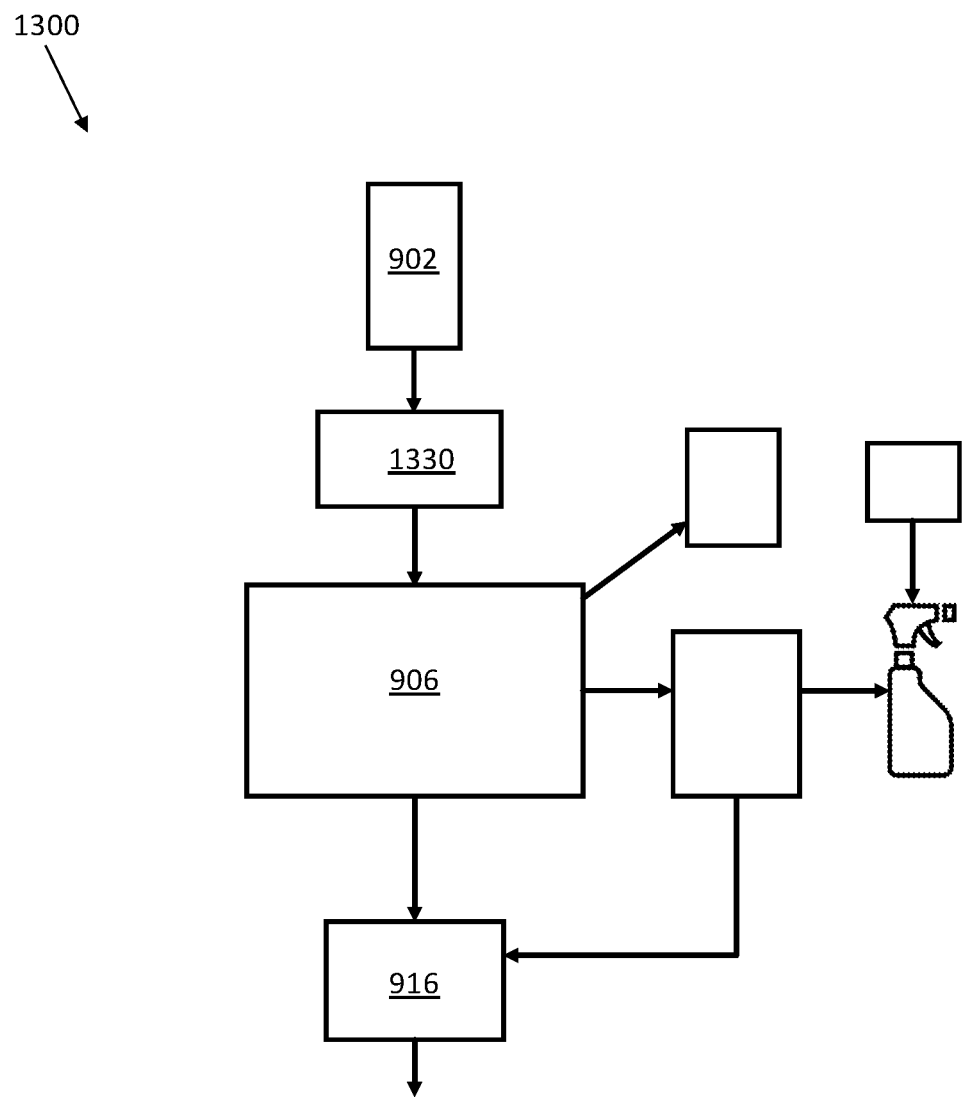
FIG. 13 illustrates a system 1300 for generation of an antimicrobial gas and/or solution.
Figure 14:
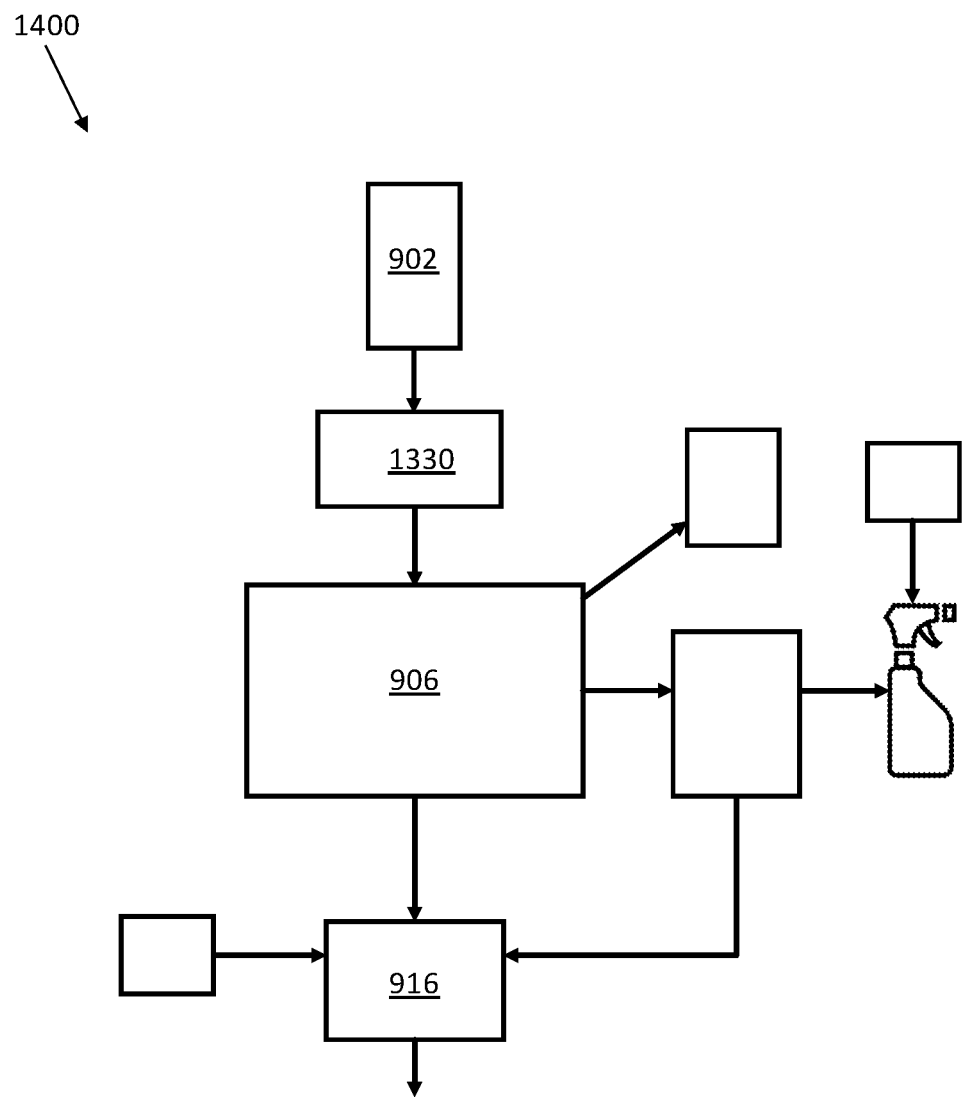
FIG. 14 illustrates a system 1400 for generation of an antimicrobial gas and/or solution.
Figure 15:
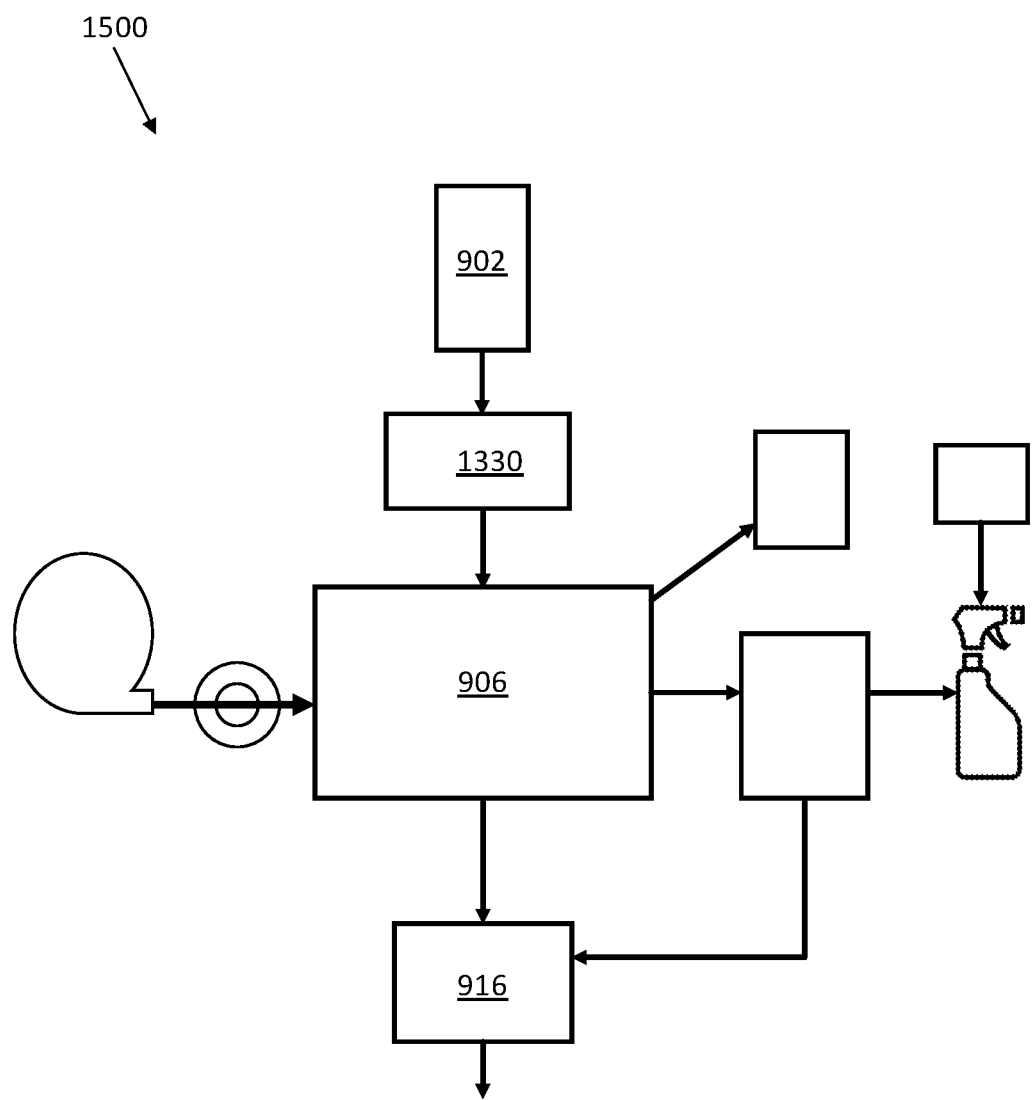
FIG. 15 illustrates a system 1500 for generation of an antimicrobial gas and/or solution.
Figure 16:
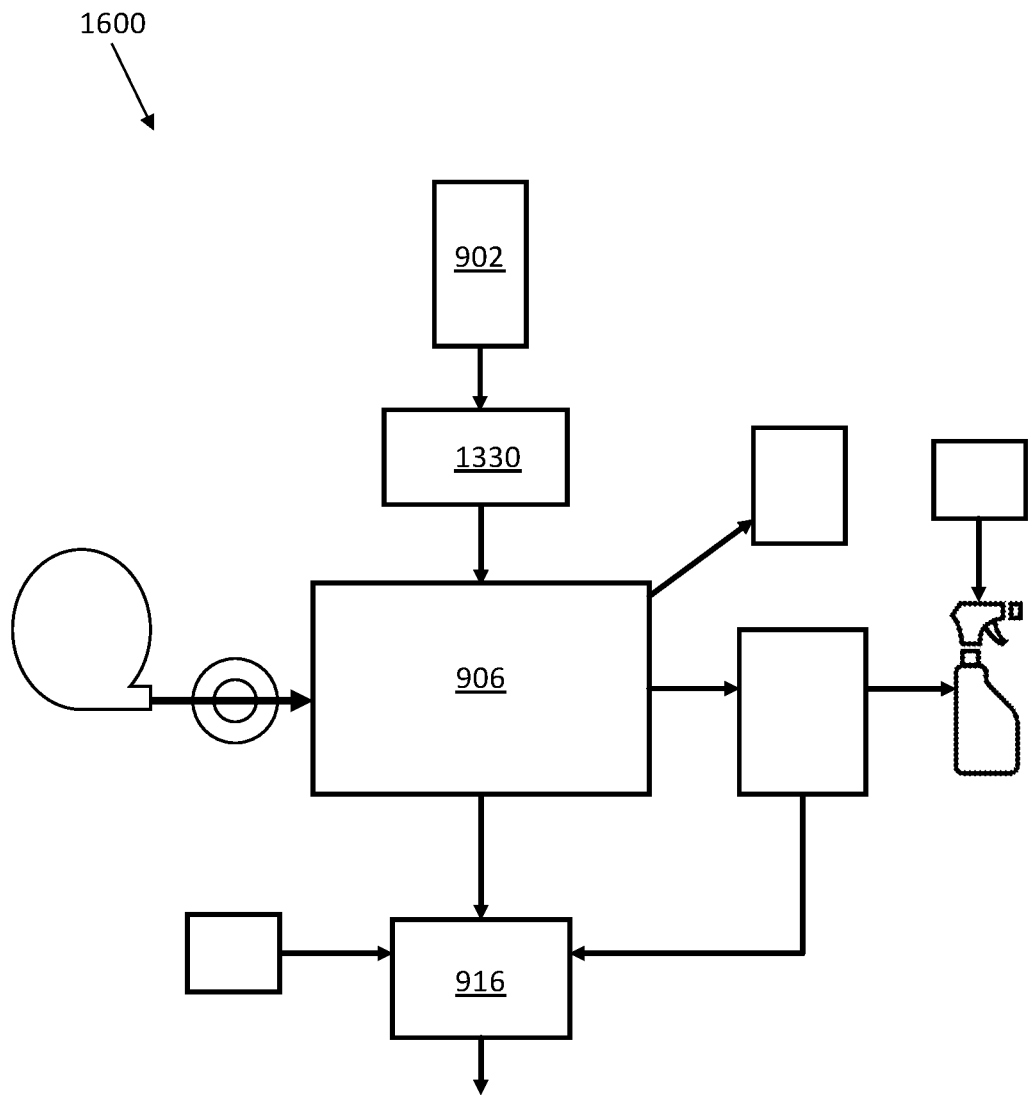
FIG. 16 illustrates a system 1600 for generation of an antimicrobial gas and/or solution.
Figure 17:
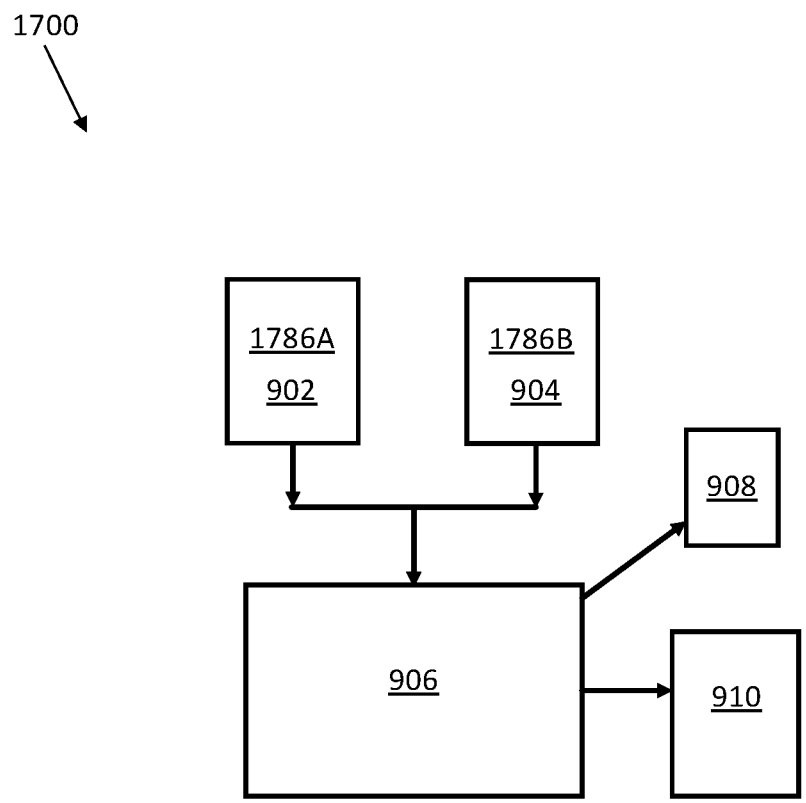
FIG. 17 illustrates a system 1700 for generation of an antimicrobial gas and/or solution.
Figure 18A:
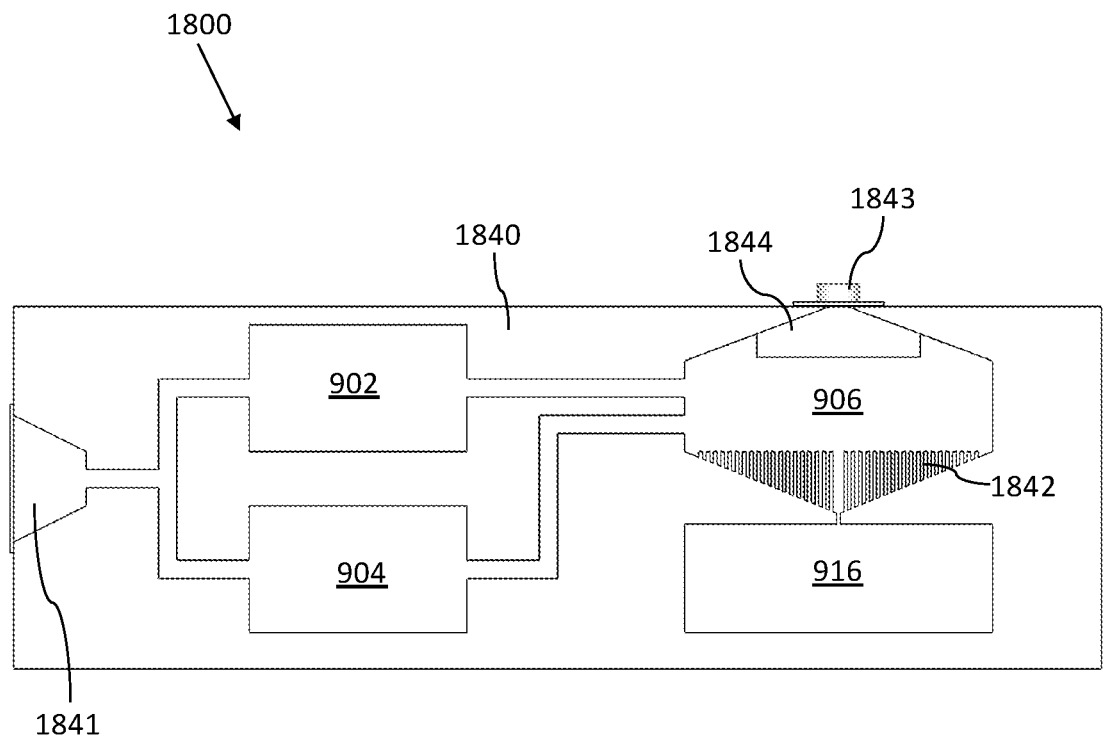
FIG. 18A illustrates a plan view of a reactor 1800 for generating an antimicrobial gas.
Figure 18B:
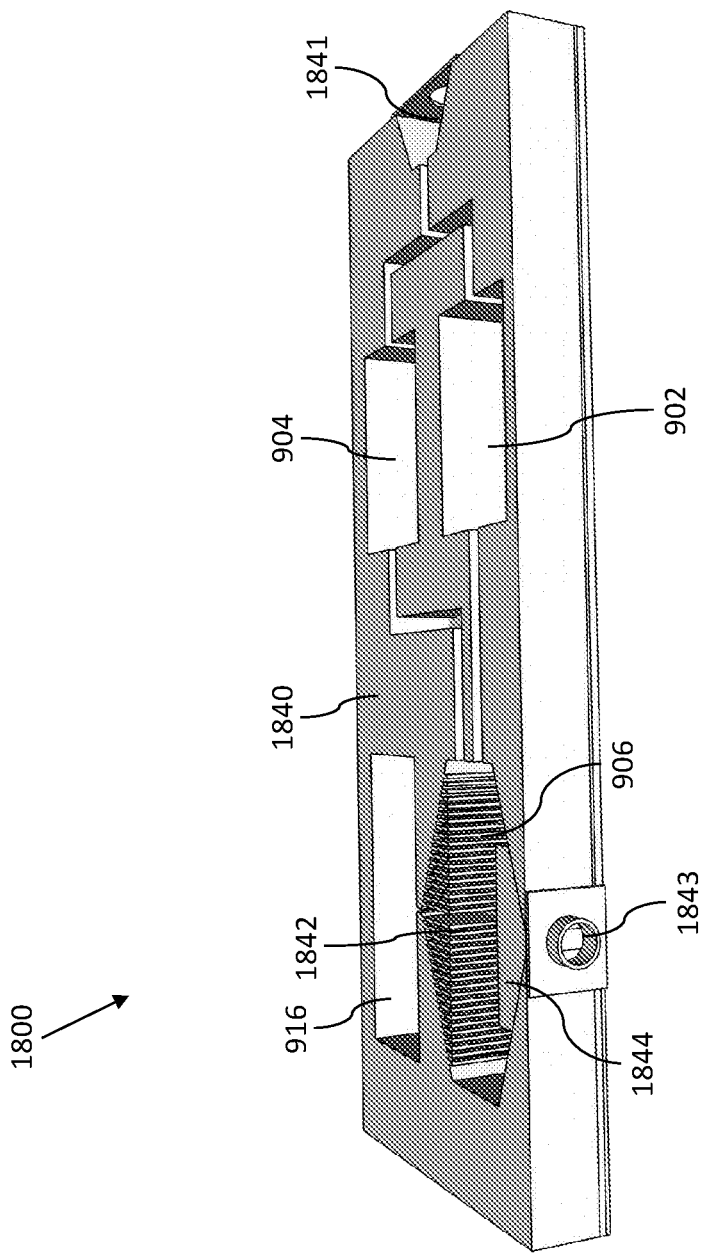
FIG. 18B illustrates a front perspective view of reactor 1800 for generating an antimicrobial gas.
Figure 18C:
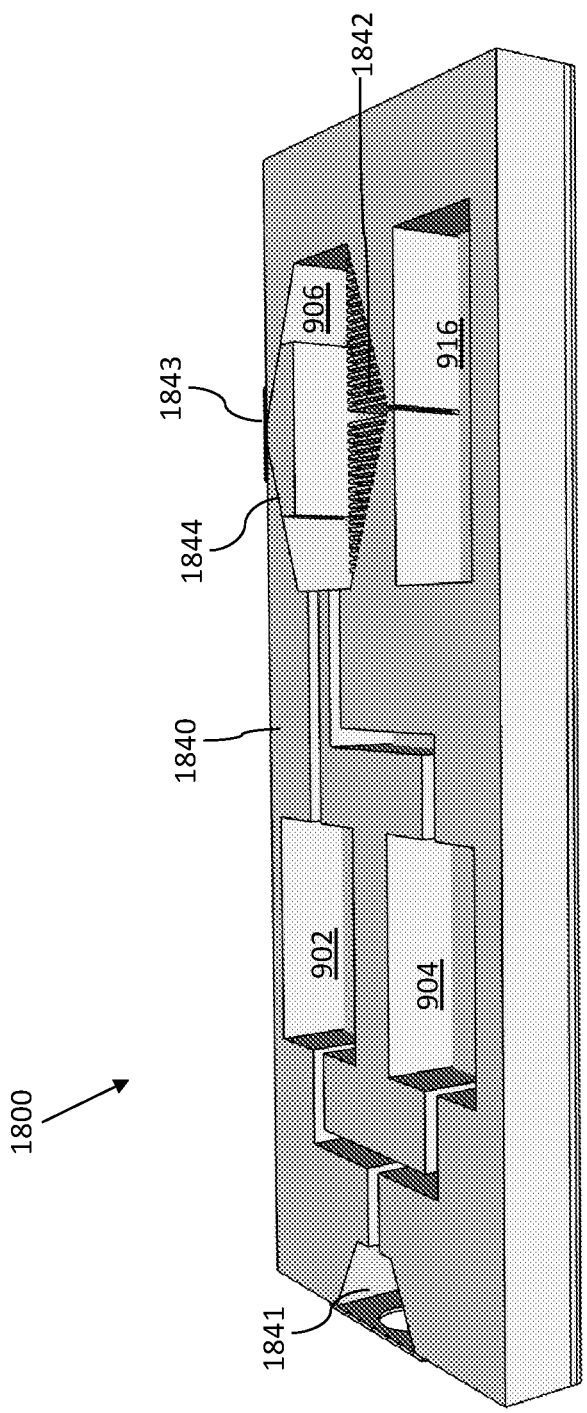
FIG. 18C illustrates a top perspective view of reactor 1800 for generating an antimicrobial gas.
Figure 18D:
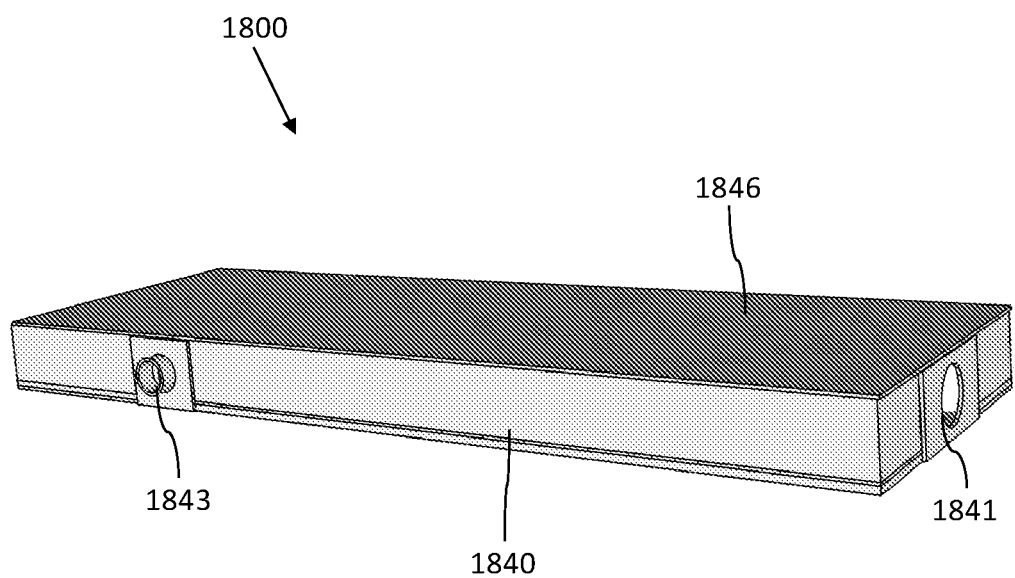
FIG. 18D illustrates a front perspective view of reactor 1800 for generating an antimicrobial gas.

In both systems 300 and 400, ambient air 302 may be ducted to air pump 308C, which causes a sample of ambient air 302 to enter a concentrator 324. Concentrator 324 may separate antimicrobial gas (e.g., $ClO_2$ gas) from the mostly diamagnetic other components of ambient air 302. One aspect of a concentrator is illustrated in FIGS. 8A and 8B. Concentrator 324 may separate and concentrate a very low concentration of antimicrobial gas (e.g., $ClO_2$ gas) so that a more accurate measurement of its concentration may be obtained. Concentrator 324 may utilize magnets to separate diamagnetic gases from antimicrobial gas, thus permitting the testing of a concentrated and amplified level of antimicrobial gas. Diamagnetic gases may be passed back into the ambient environment after separation. In one aspect, antimicrobial gas may be amplified at least 100 times prior to further concentration testing.

Systems 300 and 400 may include a sensing system 326. Sensing system 326 may sense the concentration of antimicrobial gas (e.g., $ClO_2$ gas) (which may be amplified 100 times or more following processing in concentrator 324). Sensing system 326 may measure a time weighted average of the concentration of antimicrobial gas (e.g., $ClO_2$) in ambient air 302. Data regarding the concentration is passed to microcontroller 306, and if necessary, microcontroller 306 causes system 300 or 400 to generate more or less antimicrobial gas based upon the concentration measured in sensing system 326.

After sensing in sensing system 326, the sampled gas passes via a passage to off-gas and waste chamber 322 and is ultimately passed into the ambient atmosphere with the generated antimicrobial gas.

Thus, systems 300 and 400 may measure the concentration of antimicrobial gas (e.g., $ClO_2$ gas) in ambient air 302, and if the concentration is below the target concentration, microcontroller 306 can cause system 300 or 400 to generate more antimicrobial gas to raise the concentration of antimicrobial gas (e.g., ClO$_2$ gas) in ambient air 302 until the sampled ambient air 302 meets the target concentration threshold.

All microcontrollers referenced herein (including microcontroller 306), may have the computational ability and local data storage ability to enable closed-loop control of the antimicrobial gas generation system (including systems 300, 400, 600, and 700), including but not limited to: (1) local storage and microcontroller operations on data from sensor systems for antimicrobial gas (e.g., ClO$_2$) levels to the space environment variables such as barometric pressure, humidity, temperature, occupancy, or sounds that may be used to alter generation system (including systems 300, 400, 600, and 700) performance automatically or via user intervention; (2) measurement, local storage, and microcontroller operations on data from microfluidic sub-systems such as mass/volume sensors of reagents, pressure generator performance, microfluidic chip-borne sensors, valve status and/or any other electronic sub-system to provide control as well as storage of system performance data for maintenance, alert, troubleshooting, inactive modes of operation, active modes of operation, and local setup.

In another aspect, the system (including systems 300, 400, 600, and 700) has a communication device connected to the microcontroller and/or electronic components such that data from any electronic component within, on, or connected to the systems (including systems 300, 400, 600, and 700) or housing 304 can be gathered, locally stored, operated on by the microcontroller, and transmitted to external data gathering systems on mobile and/or fixed devices.

In another aspect, machine learning and/or artificial intelligence algorithms can be incorporated into the system (including systems 300, 400, 600, and 700) microcontroller (including microcontroller 306) to alter system performance automatically or by user interactions. An example of local control includes alteration of system performance for detection of a virus or bacteria in the ambient air, altitude, temperature, air changes in the local space measured by changes in antimicrobial gas (e.g., ClO$_2$) concentration in the air of spaces containing antimicrobial gas (e.g., ClO$_2$), changes in occupancy by living beings, alterations for user preference, prediction of cycles of occupancy/vacancy, alerts as to normal or abnormal performance of the system, and the like. In one aspect, microcontroller 306 is controlled by machine learning algorithms to alter system performance. In another aspect, microcontroller 306 is controlled by artificial intelligence algorithms to alter system performance. Microcontroller 306 may alter system performance automatically. Microcontroller 306 may alter system performance by control by a user. Microcontroller 306 may alter the system performance based upon at least one of: a detection of a virus or bacteria in the ambient air; an altitude of the system; a temperature of the system; changes in the ambient air measured by changes in a concentration of antimicrobial gas (e.g., ClO$_2$) in ambient air; changes in occupancy by living beings of an area containing the system; alterations for a user's preferences; prediction of cycles of occupancy and vacancy by living beings of the area containing the system; and a diagnosis of normal or abnormal performance of the system.

In another aspect, the system (including systems 300, 400, 600, and 700) for distribution and monitoring of antimicrobial gas (e.g., ClO$_2$ gas) in a three-dimensional space will be designed for a plurality of operating modes. A first operating mode may be designed for occupied spaces, while a second operating mode may be designed for un-occupied spaces. Future user or engineered operating modes may be added. These operating modes may be changed by authorized users on the system (including systems 300, 400, 600, and 700) network (e.g., network 300) connected to a plurality of system (including systems 300, 400, 600, and 700).

Figure 5:
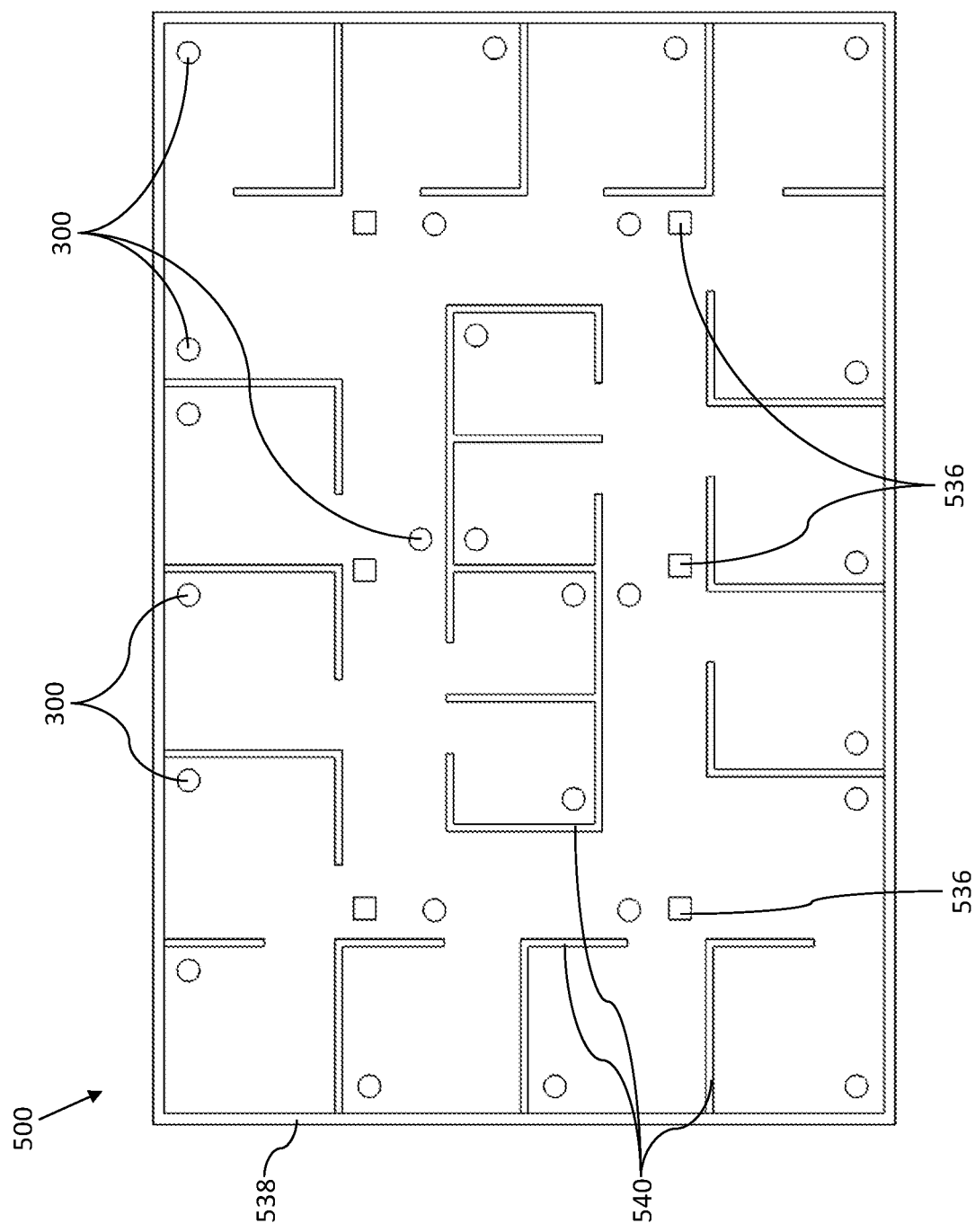
FIG. 5 illustrates an example blueprint of a network 500 of antimicrobial gas systems 300 and sensors distributed in rooms and spaces within a floor of a building.

FIG. 5 illustrates an example blueprint of a network 500 of disinfecting gas (e.g., ClO$_2$ gas) generator systems 300 and sensors 536 distributed in rooms and spaces in a floor of a building. Network 500 illustrates a floor of a building bounded by exterior walls 538 and divided by interior walls 540. Gas generator systems 300 may operate with the configuration and method of systems 300 or 400 described above, or 600 or 700 described below, and thus may include disinfecting gas (e.g., ClO$_2$ gas) concentration sensors. As illustrated, gas generator systems 300 may be oriented in each individual room of the floor, as well as in open spaces between the individual rooms. Standalone sensors 536 (configured simply to sense the concentration of disinfecting gas, such as ClO$_2$ gas, in the ambient air) supplement network 500 to ensure that the target concentration is achieved throughout network 500.

The various gas generator systems 300 may operate to generate disinfecting gas (e.g., ClO$_2$ gas) independent of one another, and at different concentration target values depending upon the desired function of a particular gas generator systems 300.

For example, where a room is occupied by a patient (e.g., in a hospital or nursing facility), employee (e.g., in an office), a guest (e.g., in a hotel), or the like, the gas generator system 300 in that particular room may have a target disinfecting gas (e.g., ClO$_2$ gas) concentration of about 50 ppb. After the room is no longer occupied (e.g., patient is moved from the room for a set period of time, employee is gone for the night, guest checks out, etc.), the gas generator system 300 in that room may increase its target disinfecting gas (e.g., ClO$_2$ gas) concentration to about 1,000 ppb to about 5,000 ppb for a set period of time. In this manner, the room can be decontaminated (1,000 ppb to 5,000 ppb concentration level, or 50,000 ppb to 300,000 ppb concentration level for extreme pathogens) between its use by particular individuals, or on a regular time schedule, and maintain a lower safe (to humans) concentration of 50 ppb for prevention or mitigation of virus spreading while occupied.

In another aspect, a plurality of systems 300 within a plurality of spaces which are arranged into network 500 can be connected via communication devices (as described above) to each other for distributed control via coordination of each system's microcontroller (e.g., microcontroller 306), centralized unit control, and/or a combination of both local and distributed control.

In another aspect, machine learning and/or artificial intelligence algorithms can be incorporated into the distributed network 500 of systems 300 by the aspects described above. Examples of distributed control include adjusting individual systems 300 to achieve uniform and/or deliberately non-uniform distribution of disinfecting gas (e.g., ClO$_2$) in each individual generator system 300's location across an entire building floor to the entire building due to changes in disinfecting gas (e.g., ClO$_2$) concentration from HVAC, consumption or self-dissipation of disinfecting gas, control of day/night generation cycles, sensing patterns across time, three-dimensional volumes, seasonal variations, and/or previously unknown factors that can be sensed either directly by the sensor systems 300 in/on the network 500, inferred or traced to the signal measured, or directly traceable to the variations observed in disinfecting gas (e.g., ClO$_2$) concentrations across a collection of systems 300 installed across distinctly separate and/or varying interconnection of real world spaces in which control of infectious species is desired.

FIGS. 6 and 7 illustrate schematics of example systems 600 and 700 for generating and monitoring antimicrobial gas (e.g., $ClO_2$ gas). Systems 600 and 700 are substantially similar to systems 300 and 400, respectively, except that air pumps 308A and 308B and pressure relief valves 310A and 310B are replaced with check valves 609A and 609B. These check valves are one-way, directional flow valves that permit the passage of fluid through check valves 609A, 609B toward reagent containers 312A, 312B, but prevent the passage of fluid away from reagent containers 312A, 312B through check valves 609A, 609B.

Such an arrangement may be used where reagent containers 312A, 312B are pressurized by an external source before or during assembly of systems 600, 700. Thus, reagent containers 312A, 312B may be pressurized containers housing reagents 314A, 314B, and as such do not need air pumps 308A, 308B to cause reagent 314A, 314B to flow to microfluidic mixer 320. The flow of pressurized reagent 314A, 314B may be controlled by a valve, such as valves 316A, 316B. When valves 316A, 316B are opened, pressurized reagent 314A, 314B may flow from pressurized reagent containers 312A, 312B, through microfluidic flow sensors 318A, 318B, and into microfluid mixer 320.

In one aspect, a closed-loop system to maintain target concentrations of an antimicrobial gas in the air, between lower bounds and upper bounds. The system may include an automated estimation of room volume (or a related characteristic) based on calculated concentration decay of a precise dosage of a gas. The system may be oriented within spaces where there is a desired and/or target gas concentration in a volume. The system includes one or more of: (a) the capability to generate and release an antimicrobial gas, (b) the capability to measure the concentration of the gas, (c) the capability to control the generation and release of the gas according to control parameters either programmed in software or controlled by digital or analog means, and/or (d) the capability to adapt to changing conditions and still maintain the target concentration.

The system may include capabilities for use in any application where a volume is unknown, where the user desires to apply, create, and/or generate a gas (or similar) in that volume, and where the gas (or similar) has a known decay characteristic such as percent decay per minute.

The system provides an advantage in that the physical volume (e.g., cubic feet or cubic meters) of the volume under treatment (e.g., a room) does not need to be previously known or previously calculated, and input into the system for the system to maintain a target concentration of an antimicrobial gas in the air. Where a system requires manual input of a predetermined volume (e.g., cubic feet or cubic meters), risk of overproduction (too high of a concentration to be safe) or underproduction (too low of a concentration to effectively manage microbials) is possible due to user volume miscalculation, user volume entry errors, and the like.

Additionally, removing a requirement for manual space volume input by a user improves safety, cost efficiency, and streamlines the adaption of the system to changing conditions (e.g., a higher antimicrobial concentration for decontamination versus a lower antimicrobial concentration for maintenance, moving the system to a different volume under treatment (having a different physical volume).

The system's automated physical volume estimation and calibration may provide a consistent, data-driven method for estimating a physical volume and the benefit of ensuring safe and efficient dosage and dispensing of an antimicrobial gas even if multiple same-size volumes exhibit different gas decay characteristics. The system permits recursive refinement of (a) the gas decay response (how the volume under treatment (e.g., a room) reacts to the dosage), and (b) the optimization of the gas generation and release cycle to improve target concentration accuracy and consistency (reduce overshoot or under-tolerance) which improves safety, cost efficiency, concentration consistency (so that other factors do not have to be tightly controlled), and the like.

The data logging of the system's sensor and other operating data generated may provide for stable, complete, regulatorily-required, and standards-based reporting of long term conditions of the volume under treatment and activities of the system suitable for submission to required and desirable government and facility management programs.

The system may permit closed-loop intelligent, digital control of very small quantities of precursors in specific ratios (e.g., from 1:1 to 1:n) and in varying dosages that are tailored for a volume under treatment, monitored for status, traceability, and quality assurance, and which can be fine-tuned to respond to changing volume under treatment conditions and/or adjusted to serve multiple treatment scenarios. The system does not rely on manual intervention for treatment, monitoring, or record keeping. The system adapts to changing conditions of the volume under treatment (e.g., light, HVAC, entry/exit of living beings, occupancy levels, and the like). The system may include built-in recording, logging, and communications to cloud services for accurate record keeping.

The system may utilize automated physical volume estimation. Automated physical volume estimation eliminates costly and error-prone measurements that would typically be used to define the treatment parameters. When used recursively, the same or similar algorithm can periodically be used to refine the treatment parameters in order to optimize for one or more performance characteristics (e.g., concentration consistency, lower operational cycle frequency, and the like). The automated physical volume estimation provides input for treatment parameters that are specific to the physical volume, and eliminates guesswork for setup parameters related to antimicrobial dosage.

In one example, a volume under treatment has an unknown physical volume. The system may generate enough gas to fill a 10 $m^3$ room to a concentration of 100 ppb. The system may wait for a specific duration and then measure the concentration of the antimicrobial gas in the volume under treatment using the device's sensor array. Knowing the expected decay rate of the antimicrobial gas in a room, the system may compare the measured antimicrobial gas concentration to the expected antimicrobial gas concentration, and calculate a ratio. The system may then apply the ratio to the 10 $m^3$ room to obtain the estimated physical volume of the room. Finally, using either an algorithm or a scaled lookup table, the system may determine the desired generation "dose" based upon the estimated physical volume of the room.

The device and system may include various modes of operation, including a normal mode of operation wherein the device at least one of: (a) establishes and maintains target concentration of an antimicrobial gas without external inputs, (b) records the performance of the device and stores the data, (c) communicates data and status when possible, (d) receives inputs from secure, authorized sources, and (e) shuts down when outside of normal operating parameters or upon experiencing an error. When the device is powered on, the device may assess the current conditions, periodically generate an antimicrobial gas (e.g., $CLO_2$) and sense the resulting concentration of the antimicrobial gas in the ambient atmosphere, ramping up to and maintaining a target concentration using closed-loop control. The device will thus generate, sense, and communicate its sensed concentrations. The device's default mode may be autonomous operation.

Figure 56:
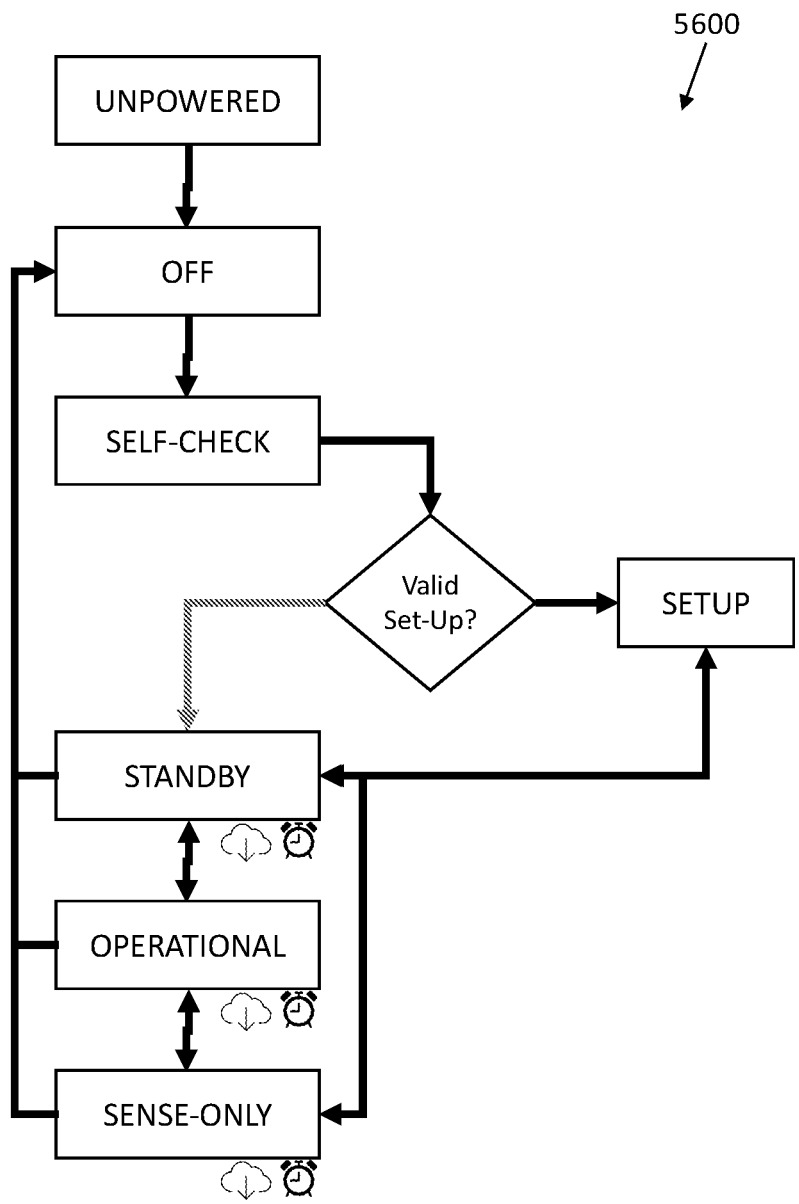
FIG. 56 illustrates a diagram of an example system 5600 for various operational modes.

FIG. 56 illustrates a diagram of an example system 5600 for various operational modes of the device, including one or more of: (a) an unpowered mode (no power is available to the device), (b) an off mode (power is available but the device is not generating or sensing), (c) a self-check mode (a standard power-on self-test ("POST") for the device CPU, checking function of control, generator, sensing, and communication sub-systems), (d) a setup mode (optional mode when device configuration needs to be updated), (e) a standby mode (the device is not operational (no generation and no sensing) but the device is configured and has power and communication functions), (f) an operational mode (the device is executing its prime directive of sensing, generating, recording, and reporting), and (g) a sense-only mode (the device is executing a portion of the prime directive, including sensing, recording and reporting, but not generating).

Cloud communication or application-based communication (e.g., from a mobile device such as a smart phone) may suggest a mode for the device, plus a duration of operation for that mode. The device may accept or decline the suggestion. For safety, the mode setting may automatically expire after some predetermined amount of time.

Standby mode (e) may include a binary toggle for the device to be powered on and communicating, but not operating (no generation, no sensing). Standby mode may provide a power-on and communication-on mode used for reporting and/or audit access. Standby mode may also be useful for a device capability wherein the device is externally switched to the operational mode (e.g., an onboard schedule or connected application tells the device to operate in operational mode (f)).

Sense-only mode (g) may include a binary toggle that disengages the gas generate function. Sense-only mode may retain communication and sensing functions. Sense-only mode (g) may be used when consumables required for antimicrobial gas (e.g., reagents) are empty. Sense-only mode may be activated from an application and/or the system may include sense-only as an automatic default option when consumables are empty.

The system and device may be set to designate operational times during a 7-day week. A default mode may be constant (e.g., 24 hours a day and 7 days a week) autonomous generation required for the device to maintain a target concentration in an operational mode. That is, the device is constantly sensing, generating, recording, and reporting. A user may activate a preset timer to activate sense-only mode (g) for a desired amount of time (e.g., x hours), wherein the device thereafter returns to operational mode (f). Other possible schedules include a preset for a particular work shift (e.g., first shift) wherein the device operates for set hours and days corresponding to that shift, which may be for example 8 AM-5 PM each day from Monday through Friday. Another possible schedule may include an occasional daily "keep fresh" schedule as desired by a user of x generation cycles per day while ignoring the target concentration, with the goal of keeping a vacant room fresh and/or reduce mold and mildew growth. Finally, a user may be able to make a custom schedule through the associated application.

Other possible device and system modes include a drone mode (h) wherein the device and system operate on command from a controller (e.g., an edge device) and reports local measures while acting to ensure its own safety parameters are not exceeded. That is, the device and system may be activated as a result of data provided by neighboring devices so as to buttress those neighboring devices. Other possible device and system modes include a team or flocking mode (i) wherein the device and system reports local measures (from its sensors) to an edge device (e.g., neighboring device). Team or flocking mode (i) may act in concert with a nearby network of peer devices to monitor and maintain an antimicrobial gas concentration in a space larger than suitable for a single device. The devices in a flocked/team mode (i) may not know they are part of a team; the cloud may gather the devices as a group based upon some relationship (e.g., proximity to one another). The cloud may evaluate data from each device and activate pre-defined onboard modes to toggle the performance of a device while maintaining the target concentrations.

The system integrates four primary sub-systems, which are supported by power and physical housing, including: (a) command and control sub-system, (b) communications sub-system, (c) sensing sub-system, and (d) generation sub-system.

Figure 57:
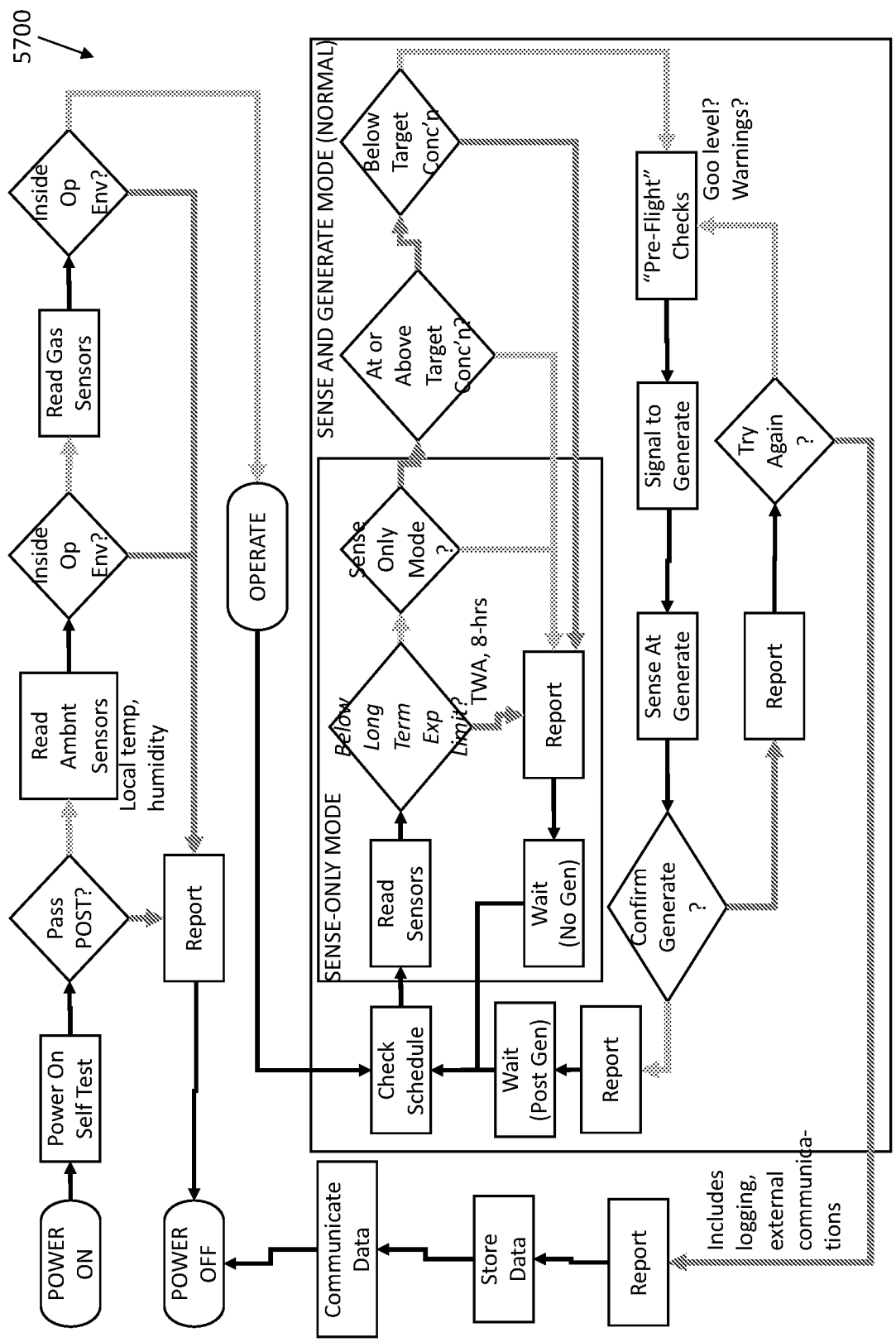
FIG. 57 illustrates a control sub-system 5700.

(a) The control sub-system is illustrated as sub-system 5700 in FIG. 57. The control sub-system 5700 manages the other sub-systems and ensures that the device performs as expected. Control sub-system 5700 may manage device initialization (new install) to prompt for and allow configuration of parameters that support normal operation, including one or more of: (i) configure and store device identification and location information, (ii) configure and store networking communications settings, and (iii) configure and store any other user preferences or performance parameters.

Control sub-system 5700 may manage device startup (power on), which may include checking communications sub-system, generation sub-system, and sensing sub-systems for any errors or conditions that would indicate against operation, including one or more of: (i) critical system errors, (ii) ambient conditions outside of operating parameters, (iii) gas sensing conditions outside of operating parameters, and (iv) generator errors or insufficient consumables.

Control sub-system 5700 may determine a desired operating mode and subsequently may run according to the operating mode, which may include one or more of: (i) run sensor and read levels, (ii) check levels against exposure limits, (iii) run generator if needed (iv) report on status, (v) wait for next cycle, and (vi) change mode and/or shut down the system if warranted.

Control sub-system 5700 may listen for any interrupts or commands, log information locally, and communicate information externally.

A power system may support the device and system by taking input power (standard AC) and delivering output power to the components of the device and system. Alternatively, the power system draws from onboard storage (e.g., batteries) to ensure device viability during periods of absence of facility power sources, and providing for the graceful shutdown with assured storage of important data during extended facility power outages.

A housing may support the device and system by providing packaging, protection, and location support. The housing may: (a) hold and position all of the components, (b) provide features for mounting to a wall or placement on a surface, (c) protect the device from external hazards, including liquids, particles, and physical impacts, (d) provide aesthetic features increasing the acceptability of the presence of the device in occupied spaces, (e) provide additional security of the consumable components should their supply containment fail, (f) provide standards based locations for product labeling and regulatory required information, (g) provide visually detectable device identification and authentication features ensuring the manufacturers identity, (h) provide ports for connections between internal components (e.g., onboard power system or networking system) and facility services (standard AC power, internet, and the like), (i) provide feedback device viewports (e.g., a display device or LED status lights), and/or (j) provide venting for thermal control of exhaust of heat and intake of room air for measurements. The housing may additionally include electromagnetic interference ("EMI") shielding to protect device components from EMI exposure and/or limit radiation of EMI from the device into the surrounding environment.

(b) The communication sub-system connects either via standard wired (e.g., USB, serial wires, ethernet, and the like) and/or wirelessly (e.g., wireless ethernet, Bluetooth, near field communications, and the like) to a network and exchanges data with a cloud service on an external network. Via the communication sub-system, the device and system may use networking to connect securely through a local intranet and to a cloud service on an external network. The communications protocols may be secured using standard-based industry practices including the exchange of security certificates held in secure persistent microelectronics resident on the device. Via the communication sub-system, the device may send performance, status, and history data to a cloud service for secure off-site storage as well as further analysis.

(c) The sensing sub-system utilizes a set of sensors, controls, air pumps, and air flow chambers to evaluate ambient air and measure and/or report multiple parameters. A blower may move (pull) ambient air from the volume under treatment, through a filter, into a plenum that houses multiple sensors which are connected to control sub-system 5700. Clean ambient air may be filtered to remove dust and other particles that could adversely affect the sensors; filters may be selected such that the filters do not interact with measured gas(es) or change the temperature, relative humidity, or other parameters material to the functioning of one or more of the sensor components. Air may be routed through the plenum (a specifically designed set of ducts that route air across multiple digital and/or analog sensors mounted to a sensor circuit board). Air flow rates may be managed across a set of sensors through control of the blower.

The sensors may measure and report values to control sub-system 5700, which is connected to the sensors via wires. The sensors may report temperature, humidity, the presence and activity of reducing and/or oxidizing gases including many commonly found volatile organic compounds ("VOCs"), and the specific gas of interest (e.g., antimicrobial gas) to the system. VOCs may be characterized by the interpolation of characteristic patterns of sensor readings at, for instance, different temperature settings of components of the digital sensing device. At least one additional, identical VOC sensor may provide redundant measurements related to VOCs. The additional VOC sensor may be left inactive in order to act as a replacement should another sensor fail, thereby increasing the reliability and lifespan of the device and system. The additional VOC sensor may also be shielded from exposure to environmental gases and used as a baseline control to support differential signal analysis. A control algorithm may adjudicate the functionality of one or more of the sensor devices such that data from malfunctioning sensors may be excluded from further processing to avoid corrupting the data.

Figure 58:
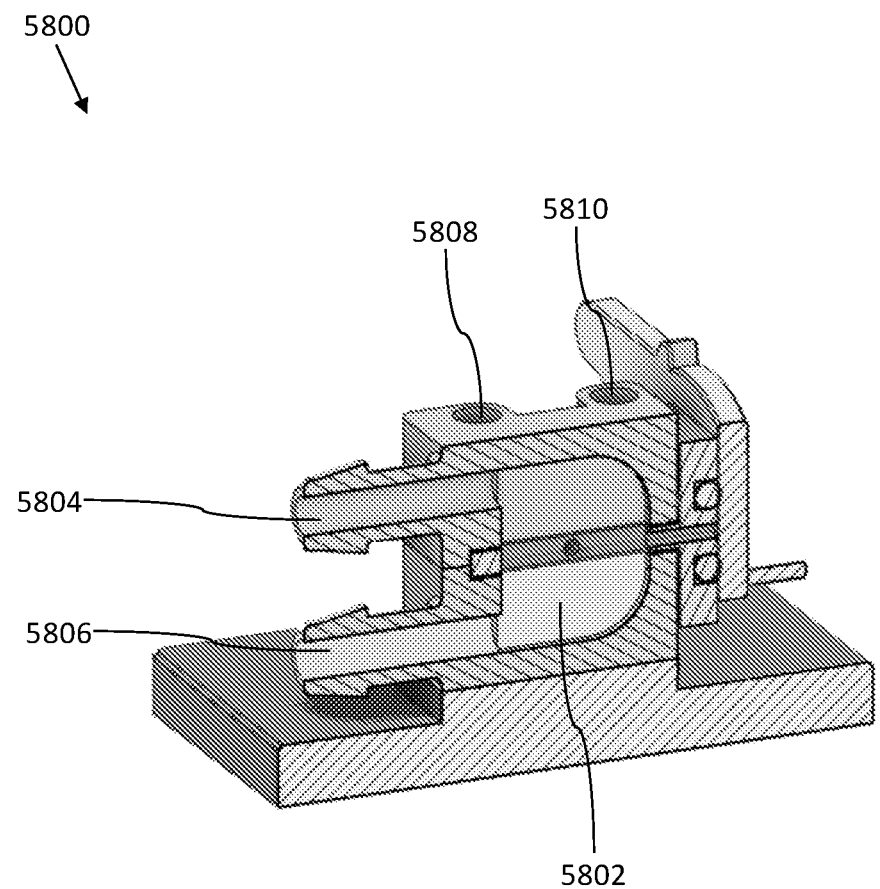
FIG. 58 illustrates a reactor 5800 for generating an antimicrobial gas.

(d) The generation sub-system utilizes differential pressure or pumps to convey precursors in a specified ratio to a reactor, such as reactor 5800 illustrated in FIG. 58. Reactor 5800 may include at least one peristaltic, or other high accuracy, pump(s) provide fluid handling. The pumps may be digitally controlled and monitored to ensure accurate dosage and recordable history. Peristaltic pumps provide accurate dose measurement and may eliminate need for optional check valves or other backflow prevention, are capable of self-priming, and are tolerant of bubbles in the hoses. Peristaltic pumps may use replaceable tube sets with one or more choices for tubing inner diameter to provide a wide range of precision and volume options. Peristaltic pumps can be independent, or the pump heads can be combined to drive multiple parallel tube sets using the same motor drive, reducing motor cost and complexity.

The pump mechanism can be contained in a removable and/or replaceable consumables cartridge to limit fluid connections or interfaces, and ensure quality pumping for the life of the consumables because the tube sets and other mechanical components of the pump head will wear with usage. The pump mechanism can be custom designed for high volume production, compact packaging, and predictable and reliable function. The pump mechanisms can be designed for very low power consumption, increasing the lifetime of the unit and extending the time between maintenance and/or changes to, for instance, battery power systems.

Reactor 5800 includes a mixing chamber 5802 where two liquid reagents meet from two input tubes 5804, 5806, and two air chambers 5808, 5810 that help direct the output antimicrobial gas to exit reactor 5800. The liquid reagents react and generate the desired antimicrobial gas. Two air chambers 5808, 5810 surround mixing chamber 5802, and each air chamber 5808, 5810 contains a hydrophobic membrane to keep the liquids inside the fluid mixing chamber 5802. The two hydrophobic membranes may be mechanically secured between the components of the reactor to prevent leaks and ensure liquid containment. Reactor 5800's design may be parametric to easily scale reactor 5800 for different doses. Reactor 5800 may utilize a wide range of air pressures and flow rates to leverage existing air flow devices and reduce need for duplicate components. In one aspect, the same blower used to pull air into the sensing sub-system may be used to push air into reactor 5800.

The blower may move (push) air into reactor 5800 in low volumes and low pressures consistent with standards required for various volumes under treatment, such as HVAC standards for hospital rooms. This air moved into reactor 5800 may help facilitate liquid mixing, encourage thorough antimicrobial gas generation, and usher the antimicrobial gas out of the device. The blower may be designed and deployed in the airflow pathway such that incoming air is drawn through and over the sensor plenum before passing through the blower to remove the possibility of blower materials affecting the various measurements acquired by the sensors.

Figure 59:
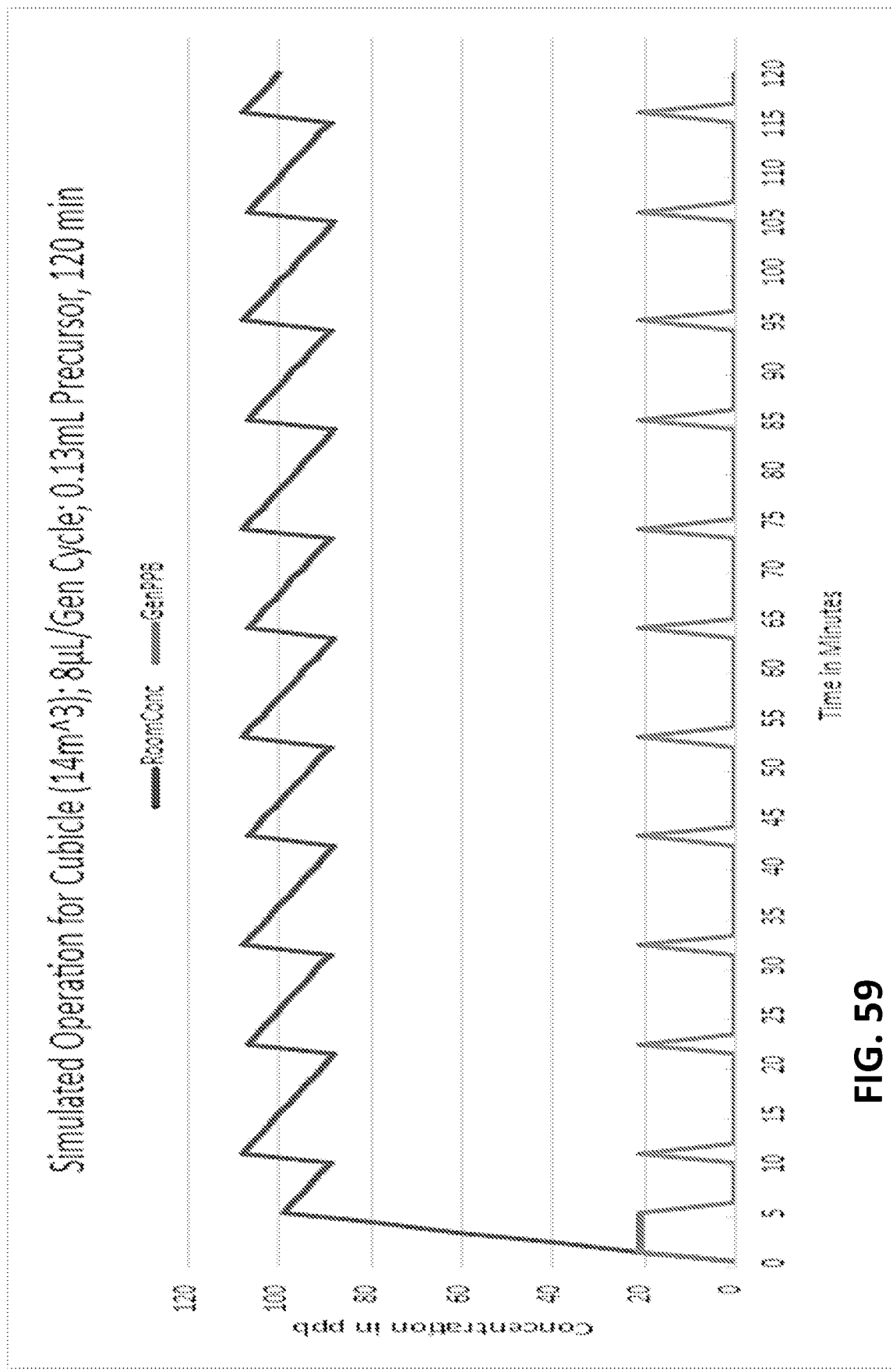
FIG. 59 illustrates a graph of concentration of antimicrobial gas versus time for a simulated operation of an antimicrobial gas system and device.

FIG. 59 illustrates a graph of concentration in ppb of antimicrobial gas versus time in minutes for a simulated operation of the system and device for a cubicle. The cubicle has a volume of 14 m$^3$. The system and device generate antimicrobial gas in the amount of 8 μL/generation cycle. The antimicrobial gas is generated using 0.13 mL of precursor. The simulation and graph cover 120 minutes of operation. The upper line is the room concentration of antimicrobial gas in ppb, while the lower line is the concentration of antimicrobial gas generated in each generation cycle, in ppb.

Figure 60:
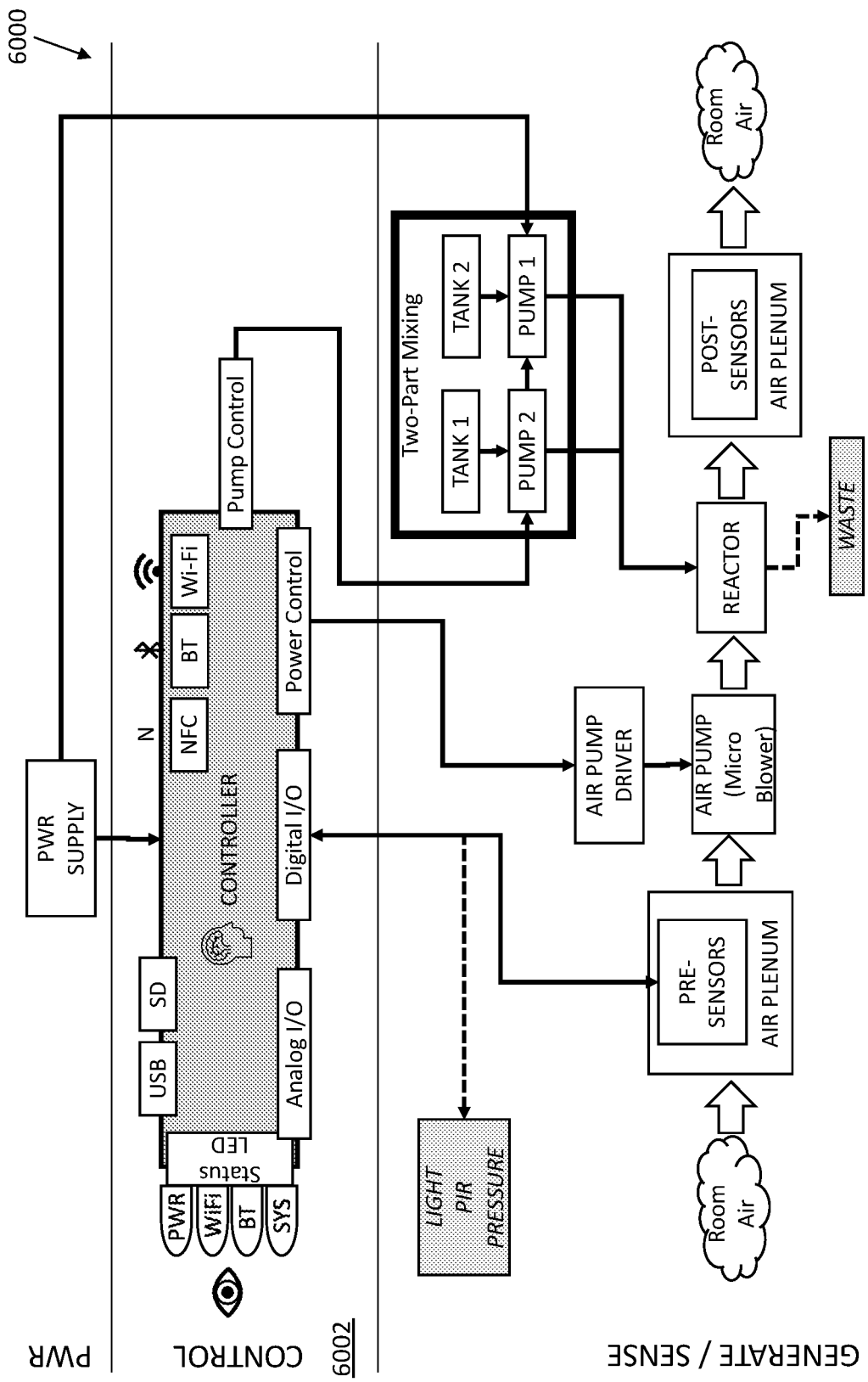
FIG. 60 illustrates a schematic of a closed-loop system 6000 to maintain target concentrations of an antimicrobial gas in the air.

FIG. 60 illustrates a schematic of a closed-loop system 6000 to maintain target concentrations of an antimicrobial gas in the air, between lower bounds and upper bounds. System 6000 includes a power supply electrically connected to a control sub-system 6002 and a combined generation and sensing sub-system 6004. Specifically, the power supply may be electrically connected to a controller unit of the control sub-system 6002 and one or more pumps in the generation and sensing sub-system 6004.

The controller unit may include communication elements (part of a communications sub-system) such as near-field communication (NFC), Bluetooth (BT), and Wi-Fi capabilities. The controller unit may include input/output ports such as universal serial bus (USB) and secure digital (SD) ports, which may also function as part of a communications sub-system. The controller may include status lights (status LED) indicating power status, Wi-Fi status, Bluetooth status, and system online status. The controller unit may include analog and digital inputs and outputs. The controller may include power control operatively connected to an air pump driver and an air pump (e.g., a micro blower) of the generation and sensing sub-system 6004, and a pump control operatively connected to the one or more pump of the generation and sensing sub-system 6004.

System 6000 uses the air pump of generation and sensing sub-system 6004 to pull room air into a plenum that houses multiple pre-sensors. Alternatively, system 6000 may include multiple pre-sensors and/or sensors outside of the plenum. The air pump then moves that same room air into a reactor in generation and sensing sub-system 6004 (the reactor may be similar to reactor 5800 for example, or any of the variety of other reactors described herein). The reactor may receive two or more reagents from tanks (e.g., tanks 1 and 2), pumped by pumps (e.g., pumps 1 and 2), into a mixing chamber. Waste from the mixing chamber may be directed out of the reactor, while a resultant antimicrobial gas may be directed into a plenum that houses multiple post-sensors. The resultant antimicrobial gas may be introduced to the ambient, room air for treatment of the room air.

Measurements and data from the pre-sensors and/or post-sensors may be communicated to the controller for reporting, storage, and/or analysis.

Antimicrobial Target Control

In one aspect, the target concentration of antimicrobial in the volume under treatment may be controlled via a proportional, integral, and derivative ("PID") control using mathematical calculations to take the kinetics of a complex system into account without knowing the underlying causes of some of the complex occurrences within that complex system.

PID does not need to understand what is causing the observed changes in system dynamics. PID focuses upon the target concentration and the immediate and past history of trying to achieve the target concentration mathematically drives electronic to computation controls based upon mathematical operations on the target signal, rather than the complex and changing extrinsic (and often unmeasurable) real world causes of deflection from the target concentration.

System level performance changes may have real world impact in PID control schemes. For example, control constants may be adjusted to make the system more responsive, acting to achieve the target concentration more rapidly. If the target concentration in the volume under treatment is within allowable limits using this scheme, then this strategy can be employed to ensure that the system is maximized for quick changes in response to volume under treatment changes, such as the number of people in the volume, the opening or closing of doors and windows, adjustment of the HVAC system, and other events common in real world volumes under treatment.

Alternatively, the PID may be set by varying only the three PID constants to make the system much slower in response, and designed to never exceed a fixed hard maximum target (e.g., the maximum safe concentration for a particular volume under treatment).

In another aspect, the target concentration of antimicrobial in the volume under treatment may be controlled via a linear target control including the following steps: (1) input or use automated volume estimation to quantify the three-dimensional spatial volume of a volume under treatment; (2) measure the current antimicrobial concentration in the volume under treatment via antimicrobial concentration sensing; (3a) if the concentration of the antimicrobial is zero or functionally equivalent to zero (considering that concentration=mass/volume and the volume is known or estimated in step 1), instruct the antimicrobial generator to express a mass of antimicrobial estimated to be sufficient to attain the desired target antimicrobial concentration in the known volume of the volume under treatment; and/or (3b) if the concentration of the antimicrobial is non-zero, if the volume under treatment concentration is greater than the target antimicrobial concentration then the antimicrobial generator is held until the concentration is not greater than the target; and if the volume under treatment concentration is less than the target antimicrobial concentration then the antimicrobial generator is instructed to generate a mass proportional to the target antimicrobial minus the volume under treatment concentration, multiplied by the volume of the volume under treatment to bring the concentration of the antimicrobial in the volume under treatment to or above the target concentration.

Safety Assurance

In a given volume under treatment, various factors may cause decreases in antimicrobial concentration. The kinetics of decreases in antimicrobial concentration due to intrinsic characteristics associated with the volume under treatment may yield expected antimicrobial concentration losses of between 0.1% and 25.0% per minute, with real world expectations and experimental proof demonstrating a range of between 1.0% and 6.0% for indoor rooms, and up to 25.0% for airplanes and small vehicles (e.g., automobile) volumes under treatment.

In one aspect, with the aforementioned loss rates in mind, the antimicrobial generators may be capable of dosing an antimicrobial to fill or make-up concentration in cycles that have a generation duration of at least 0.25 seconds.

The systems herein may include a circuit, algorithm, or secondary component that can act as a programmable governor on the frequency generation (and the inverse delay durations) cycles of the antimicrobial generator. As opposed to simple delay circuits, in the context of a digital disinfection strategy, the systems described herein may vary this programmable governor based upon simple factors, including for example: (1) the dispersion time variable; (2) the antimicrobial decay variable; (3) the user input or estimated volume of the volume under treatment; and (4) user input features of a volume under treatment, including for example, windows, doors, known HVAC design parameters, the presence of absorptive materials in the volume under treatment (e.g., furniture, carpet, curtains, bedding), and the like.

In another aspect, the systems described herein may be closed-loop system with the means to measure, record, store, and act on, within the target antimicrobial concentrations, a sensor signal proportional to or indicative of the concentration of an antimicrobial in the volume under treatment. The closed-loop systems can use the antimicrobial concentration sensing system to: (1) confirm that a cycle of emission from the antimicrobial generator has the expected concentration effect in the volume under treatment; and/or (2) monitor the power consumption, activation voltages, amperages, or digital signals to components that are utilized in the options of the antimicrobial generators described herein.

With respect to (1) described immediately above, if one or more cycles of generation have occurred and no volume under treatment concentration is sensed by the antimicrobial concentration sensing device, the closed-loop system will pause/stop/disable the generation unit and ensure that visual, auditory, tactile, and/or data-driven alerts/alarms/warnings are issued to avoid providing a dangerous concentration of antimicrobial to the volume under treatment. Where the concentration in a volume under treatment exceeds an accepted target antimicrobial concentration, an alert may be issued for a non-threatening overconcentration, while an alarm and a stop to all generation activities is issued for a threatening overconcentration. Where the concentration in a volume under treatment does not reach the target antimicrobial concentration when the closed-loop system expects it to reach that concentration (as sensed by the antimicrobial concentration sensing system), then generation activities may be stopped and service personnel may be alerted to examine the unit to ascertain why the target function of the closed-loop system is not being achieved.

With respect to (2) described immediately above, where the antimicrobial generator is an electrochemical generation with cationic membrane or electrochemical generation with evaporative extraction, measurement of the duration of the applied voltage, amperage, and/or power consumption may result in the closed-loop system shutting down generation where those voltages, amperages, or power consumption values exceed threshold values. This generation shut down may occur regardless of whether the antimicrobial concentration sensing system has detected an error. The generation shut down may trigger an alert or alarm depending upon how much the threshold values were exceeded.

Where the antimicrobial generator includes UV with evaporative extraction, the duration that the UV emitter is on, total power consumed, and the like, can be disabled once a particular threshold is achieved, independent of the other channels of data.

Where the antimicrobial generator includes two chemicals with evaporative extraction, including the use of liquid precursors, an independent encoder on a pump driver's shaft, or a time of driver voltage, amperage, pulse width modulation, and/or other signals can be totaled and compared to safe threshold values.

Antimicrobial Generation Systems and Devices

FIG. 17 illustrates a system 1700 that is substantially similar to system 900 illustrated in FIG. 9 and described above, where like reference numbers indicate like elements. System 1700 additionally includes pressurized aerosol containers 1786A and 1786B. Aerosol container 1786A may contain liquid precursor 902, while aerosol container 1786B may contain liquid activator 904. Liquid precursor 902 and liquid activator 904 may be delivered to a reaction chamber 906 using the pressure within containers 1786A and 1786B to cause the delivery. Such an embodiment may eliminate the need for electrically powered components for antimicrobial generation and dispersal.

FIGS. 18A-18D illustrate a reactor 1800 for generating an antimicrobial gas (e.g., $ClO_2$ gas). Reactor 1800 may be a prepackaged device loaded with a liquid precursor 902 and a liquid activator 904 within containers inside reactor 1800. Liquid precursor 902 may be sealed within its container and may require pressurized air to flow into reaction chamber 906. Liquid activator 904 may be sealed within its container and may require pressurized air to flow into reaction chamber 906.

Reactor 1800 may include a housing 1840 containing liquid precursor 902, activator 904, a reaction chamber 906, and a waste liquid container 916, wherein device elements are machined or otherwise formed out of a housing material, as in common in the production of microfluidic devices. Reactor 1800 may be a microfluidic device.

Reactor 1800 may include a pressure input 1841 capable of applying an air pressure to liquid precursor 902 and activator 904 to break seals within their respective containers and/or cause them to travel to reaction chamber 906. Pressure input 1841 may receive pressure from a pump, a syringe, or the like.

Reaction chamber 906 may include a capillary filter 1842 that permits waste liquid to travel into waste liquid container 916 via capillary action. Waste liquid container 916 may include an inactivator, neutralizing agent, or the like capable of rendering waste liquid from reaction chamber 906 into a safe state.

Reaction chamber 906 may include a gas permeable membrane 1844, which allows an antimicrobial gas (e.g., $ClO_2$ gas) created in reaction chamber 906 to pass through membrane 1844 at a controlled rate but prevents a waste liquid from reaction chamber 906 from passing through membrane 1844. Antimicrobial gas (e.g., $ClO_2$ gas) may exit reactor 1800 via a gas outlet 1843. Gas outlet 1843 may permit antimicrobial gas (e.g., $ClO_2$ gas) to exit reactor 1800 and enter the surrounding area, including for example an enclosed space (e.g., a room within a building).

As illustrated in FIG. 18D, reactor 1800 may include a cover 1846 that seals the above-referenced contents (e.g., liquid precursor 902, activator 904, reaction chamber 906, and waste liquid container 916) within housing 1840.

FIGS. 19A-19I illustrate a reactor 1900 for generating a disinfecting gas (e.g., $ClO_2$ gas). Reactor 1900 may include a housing 1950 having an upper surface 1952. Housing 1950 may include a container 1970 and a reaction chamber 1972 connected to one another by a chamber duct 1976, wherein device elements are machined or otherwise formed out of a housing material, as in common in the production of microfluidic devices. Reactor 1900 may be a microfluidic device.

Container 1970 may include a solid container cover 1954 oriented on or near upper surface 1952. Reaction chamber 1972 may include a reaction chamber cover 1956 oriented on or near upper surface 1952. Reaction chamber cover 1956 may include an outlet 1960 having an aperture 1958 in fluid communication with the interior of reaction chamber 1972. Aperture 1958 may include a gas permeable membrane that allows a gas (e.g., $ClO_2$) to pass through, but prevents a liquid (e.g., waste liquid) from passing through.

Chamber duct 1976 may include a valve 1980. Valve 1980 may be a check valve, backflow valve, seal, or the like that prevents the contends of container 1970 and the contents of reaction chamber 1972 from coming into contact with one another until a user selectively causes the contents of container 1970 to be transferred to reaction chamber 1972.

Container 1970 may contain a liquid activator as described above, while reaction chamber 1972 may contain a liquid or solid precursor (e.g., liquid $NaClO_2$ or solid $NaClO_2$). Alternatively, container 1970 may contain a liquid precursor (e.g., $NaClO_2$) as described above, while reaction chamber 1972 contains a solid activator or liquid activator.

Figure 19A:
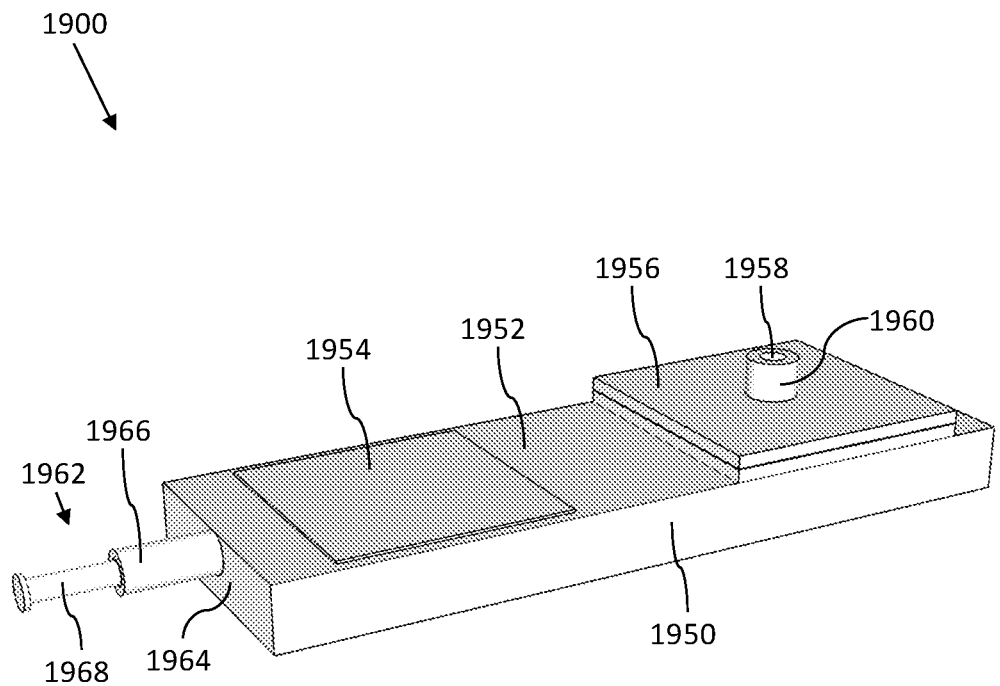
FIG. 19A illustrates a side perspective view of a reactor 1900 for generating an antimicrobial gas.
Figure 19B:
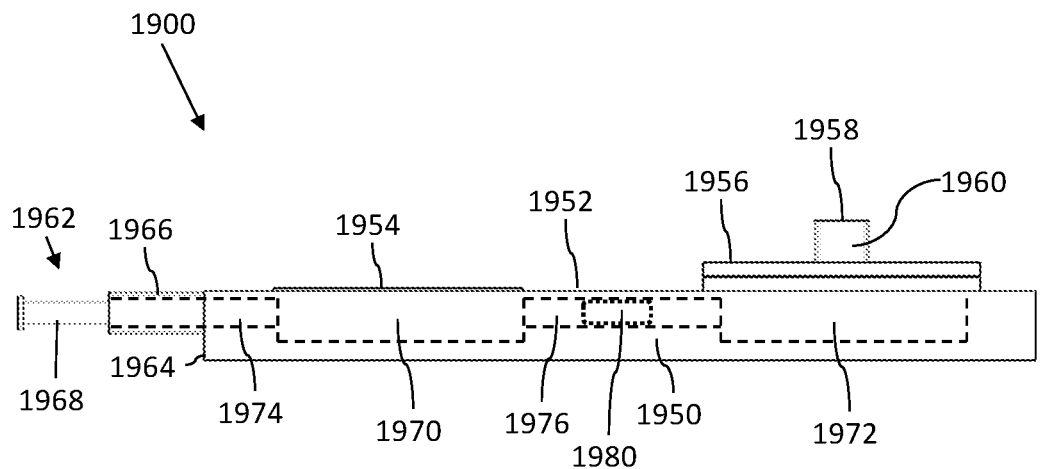
FIG. 19B illustrates a side elevational view of reactor 1900 for generating an antimicrobial gas.
Figure 19C:
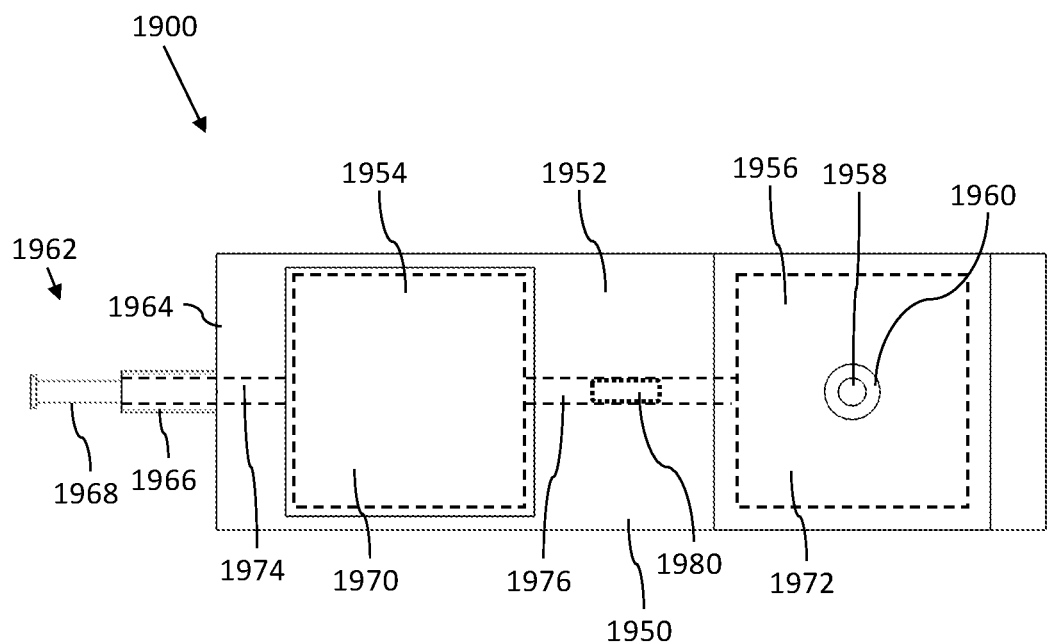
FIG. 19C illustrates a plan view of reactor 1900 for generating an antimicrobial gas.
Figure 19D:
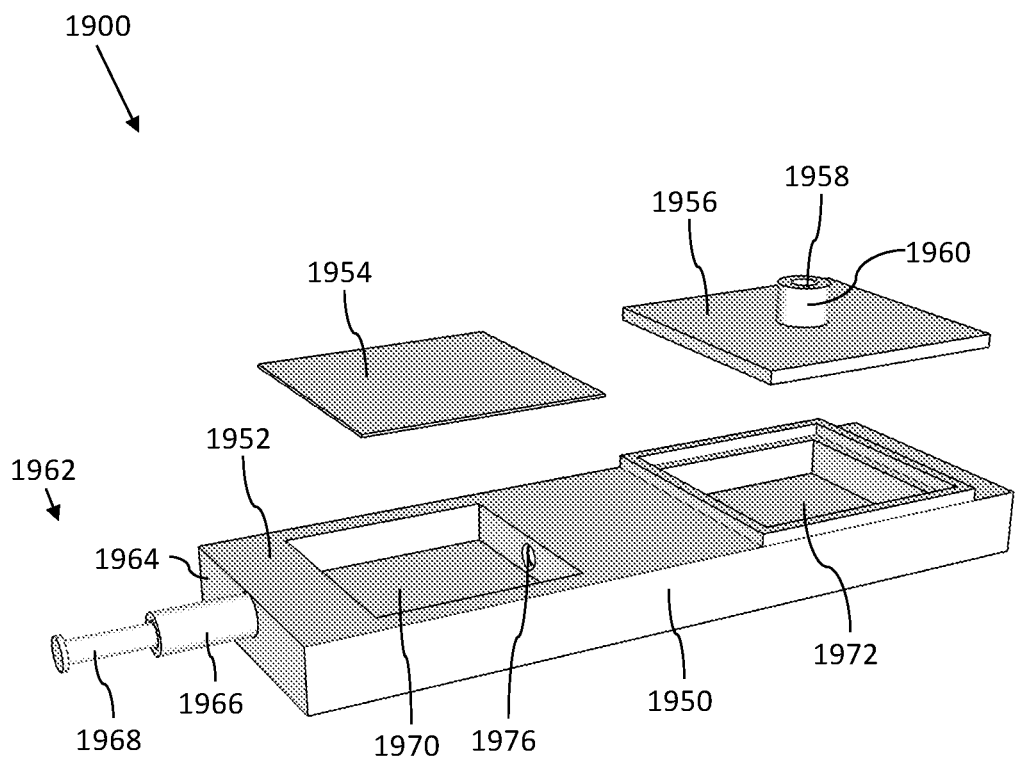
FIG. 19D illustrates an exploded side perspective view of reactor 1900 for generating an antimicrobial gas.
Figure 19E:
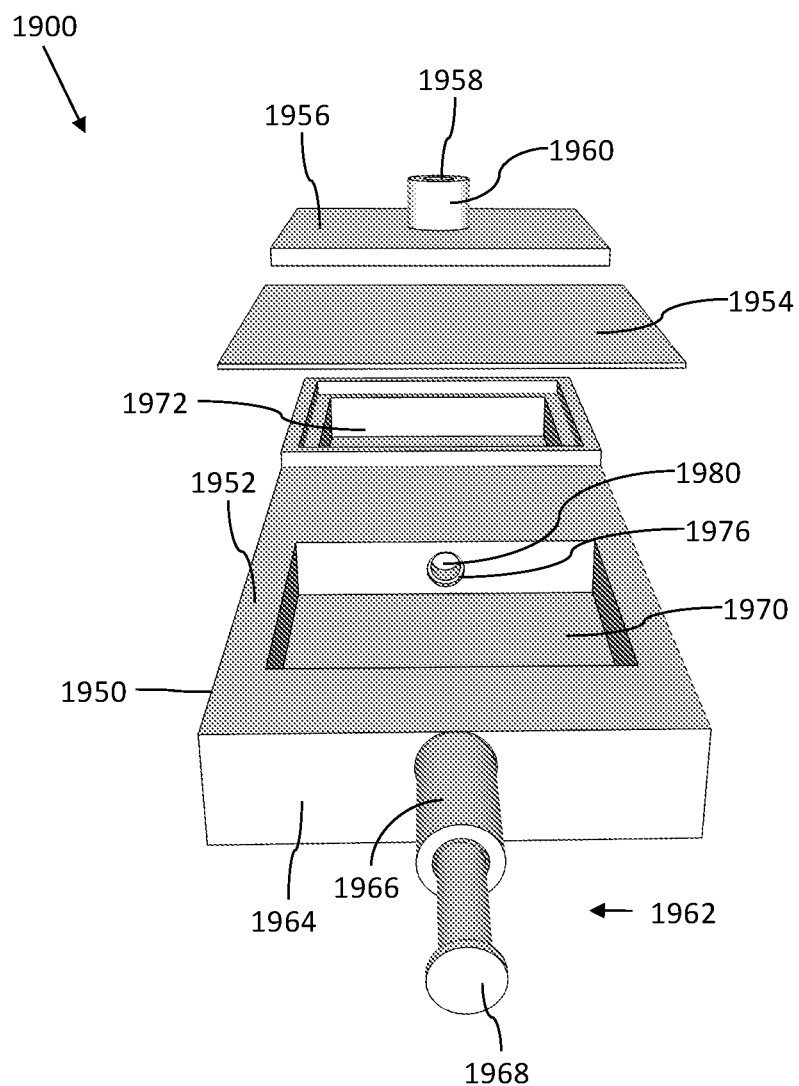
FIG. 19E illustrates an exploded front perspective view of reactor 1900 for generating an antimicrobial gas.
Figure 19F:
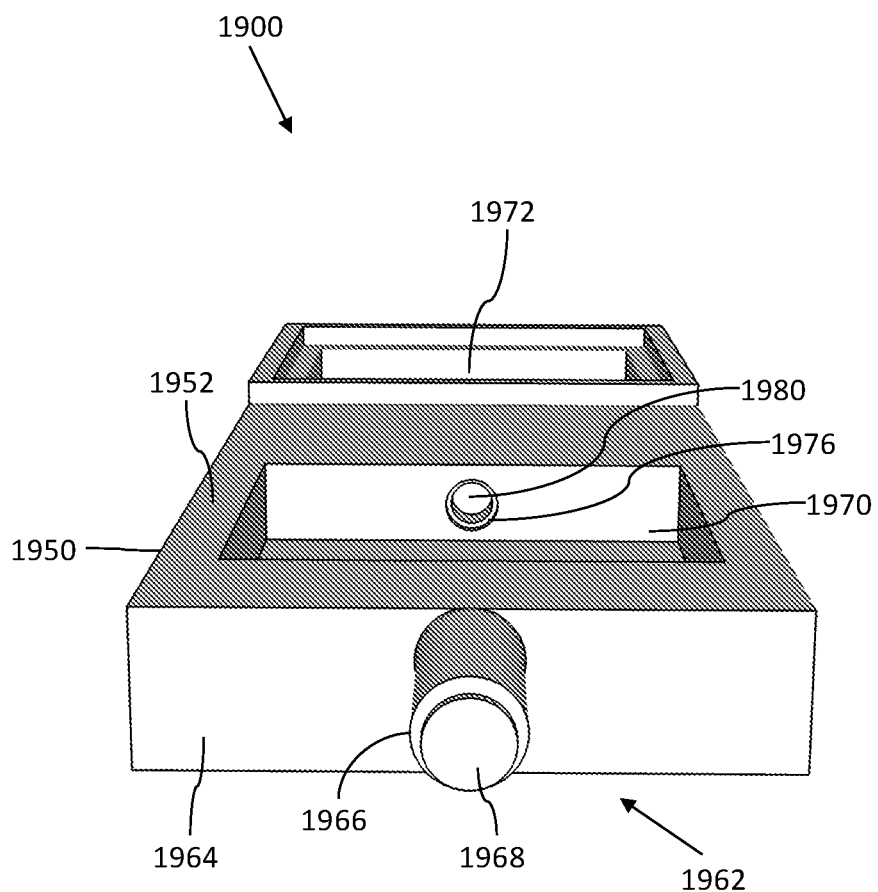
FIG. 19F illustrates a front perspective view of reactor 1900 for generating an antimicrobial gas.
Figure 19G:
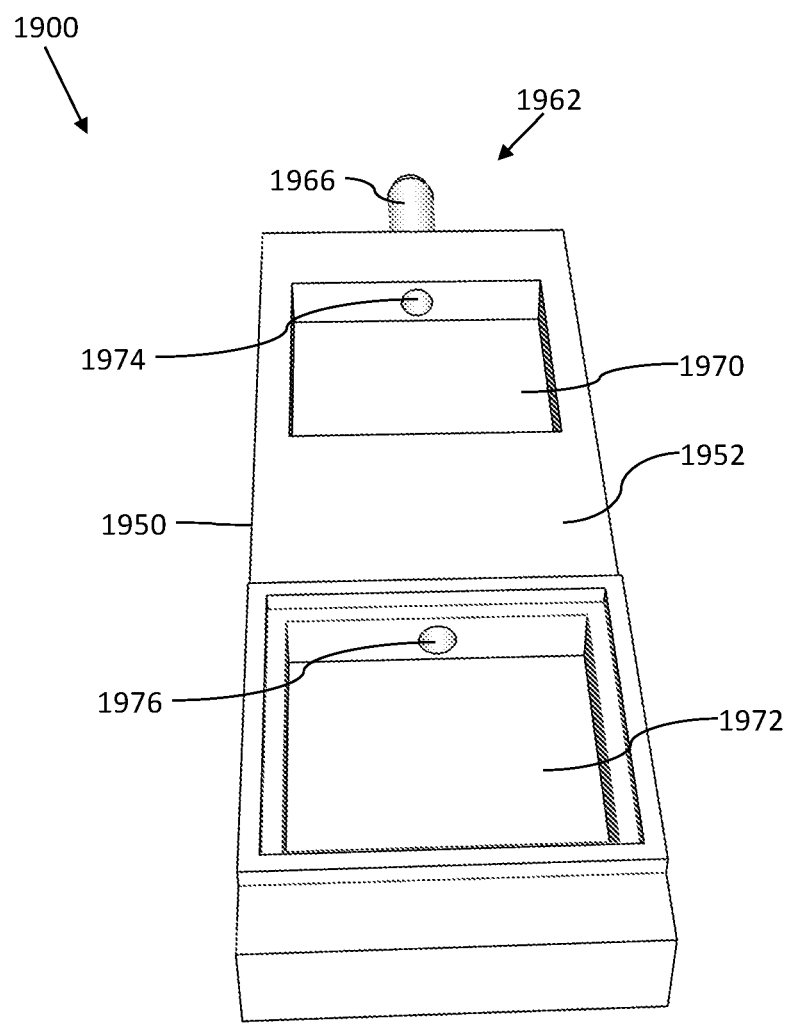
FIG. 19G illustrates a rear perspective view of reactor 1900 for generating an antimicrobial gas.
Figure 19H:
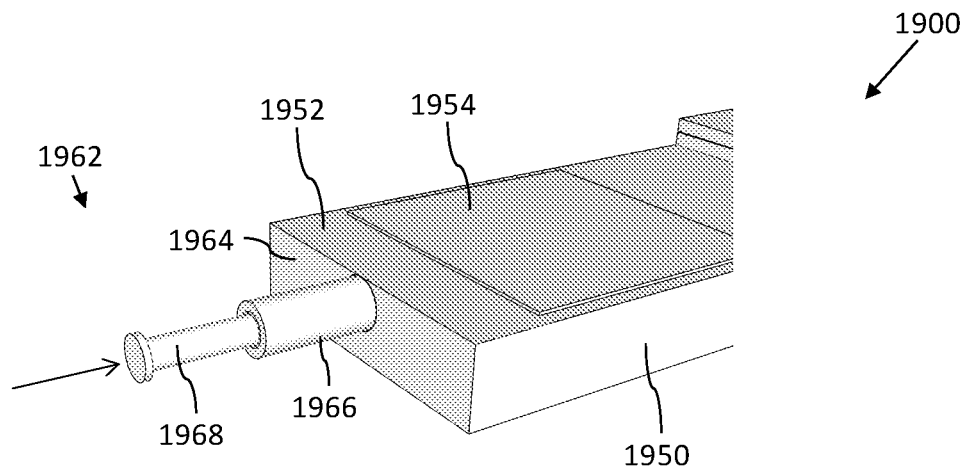
FIG. 19H illustrates a side perspective view of reactor input mechanism 1962 in a first position.
Figure 19I:
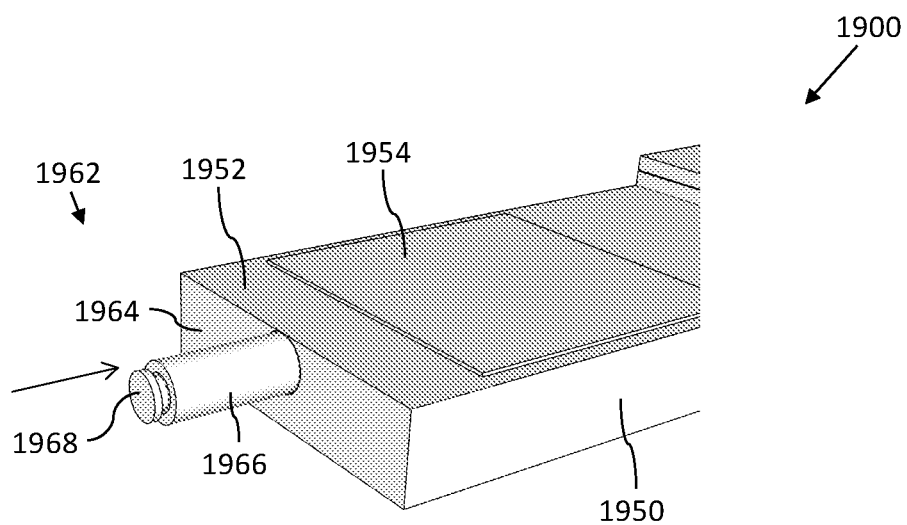
FIG. 19I illustrates a side perspective view of reactor input mechanism 1962 in a second position.

Housing 1950 may include an end 1964 including a pressurization device 1962. Pressurization device may include any device capable of pressurizing the contents of container 1970, thereby causing the contents of container 1970 to overcome and pass valve 1980 and enter reaction chamber 1972. Pressurization device 1962 may include a plunger device including a hollow body 1966 extending from end 1964 and in fluid communication with container 1970 via a pressurization duct 1974, and a plunger 1968 extending into hollow body 1966. As illustrated in FIGS. 19H and 19I, plunger 1968 may be actuated by a user and pressed into hollow body 1966, thus causing pressurization of the contents of container 1970, which overcome and pass valve 1980 and flow into reaction chamber 1972. Antimicrobial gas (e.g., $ClO_2$ gas) is allowed to escape aperture 1958 via an optional gas permeable membrane, while waste liquid is contained within reaction chamber 1972 until reactor 1900 is cleaned and recharged (fresh precursor and activator is added).

Pressurization device 1962 may be removable. Alternatively, pressurization device 1962 may be entirely separate from housing 1950 and may be applied to housing 1950 by a user only when the user desires to activate reactor 1900. Pressurization duct 1974 may likewise include a valve 1980, which may be a check valve, backflow valve, seal, or the like.

FIGS. 20A-20D illustrate a reactor 2000 for generating an antimicrobial gas (e.g., $ClO_2$ gas). Reactor 2000 may be a prepackaged device loaded with a liquid precursor 902, and a solid activator 1330 within containers inside reactor 2000. Liquid precursor 902 may be sealed within its container and may require pressurized air to flow into reaction chamber 906. Solid activator 1330 may be sealed within the reaction chamber 906.

Reactor 2000 may include a housing 2040 containing liquid precursor 902, activator 1330, a reaction chamber 906, and a waste liquid container 916, wherein device elements are machined or otherwise formed out of a housing material, as in common in the production of microfluidic devices. Reactor 2000 may be a microfluidic device.

Reactor 2000 may include a pressure input 2041 capable of applying an air pressure to liquid precursor 902 to break a seal within its container and/or cause liquid precursor 902 to travel to reaction chamber 906. Pressure input 2041 may receive pressure from a pump, a syringe, or the like.

Reaction chamber 906 may include a capillary element 2042 that permits waste liquid to travel into waste liquid container 916 via capillary action. Waste liquid container 916 may include an inactivator, neutralizing agent, or the like capable of rendering waste liquid from reaction chamber 906 into a safe state.

Reaction chamber 906 may include a gas permeable membrane 2044, which allows antimicrobial gas (e.g., $ClO_2$ gas) created in reaction chamber 906 to pass through membrane 2044 at a controlled rate but prevents a waste liquid from reaction chamber 906 from passing through membrane 2044. Antimicrobial gas (e.g., $ClO_2$ gas) may exit reactor 2000 via a gas outlet 2043. Gas outlet 2043 may permit antimicrobial gas (e.g., $ClO_2$ gas) to exit reactor 2000 and enter the surrounding area, including for example an enclosed space (e.g., a room within a building).

Figure 20A:
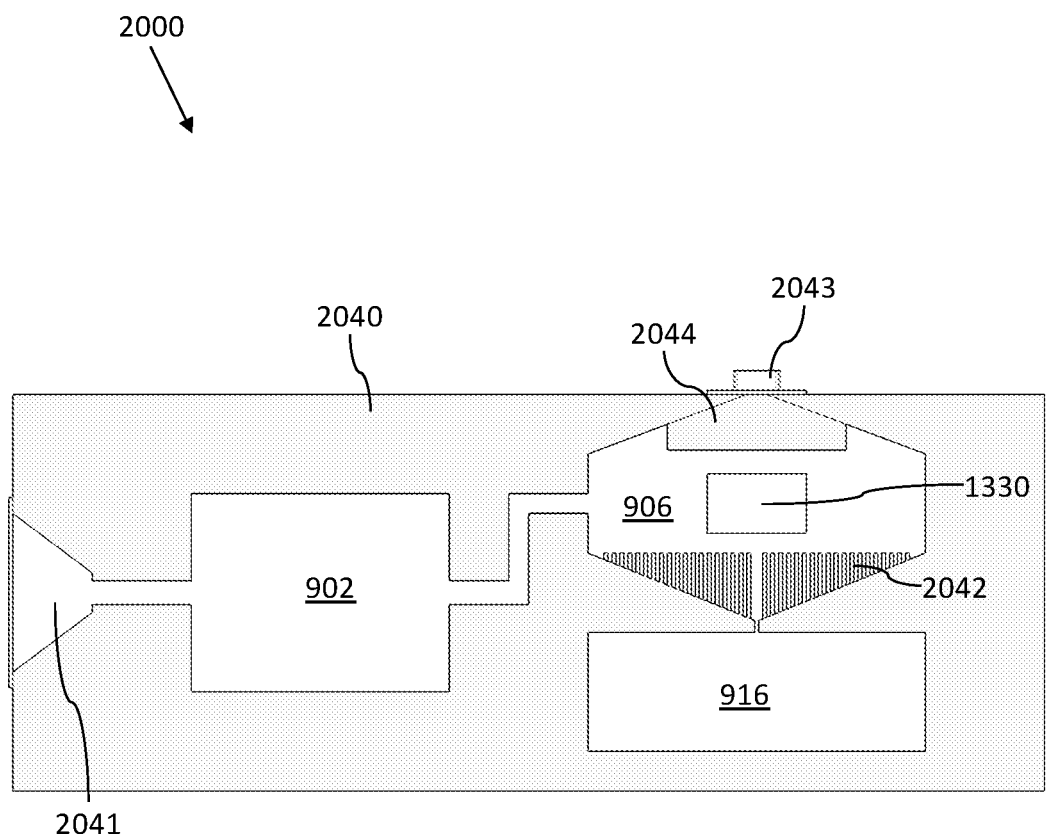
FIG. 20A illustrates a plan view of a reactor 2000 for generating an antimicrobial gas.
Figure 20B:
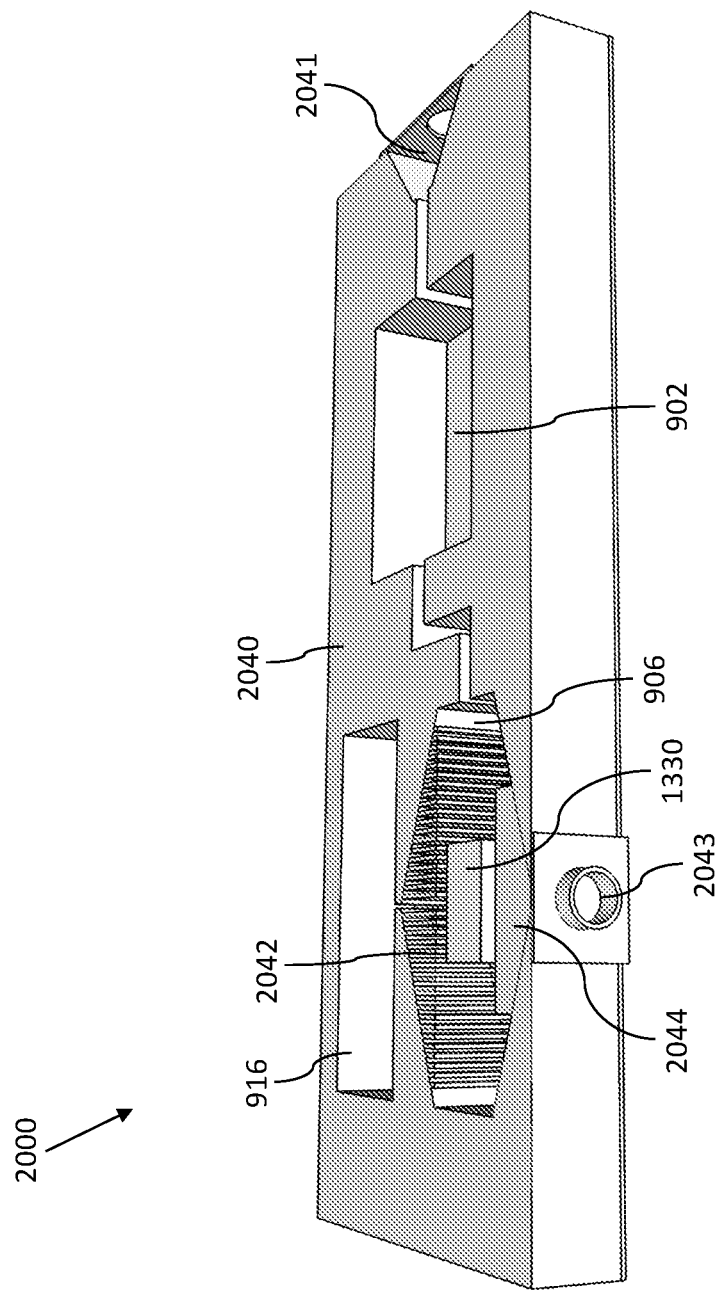
FIG. 20B illustrates a front perspective view of reactor 2000 for generating an antimicrobial gas.
Figure 20C:
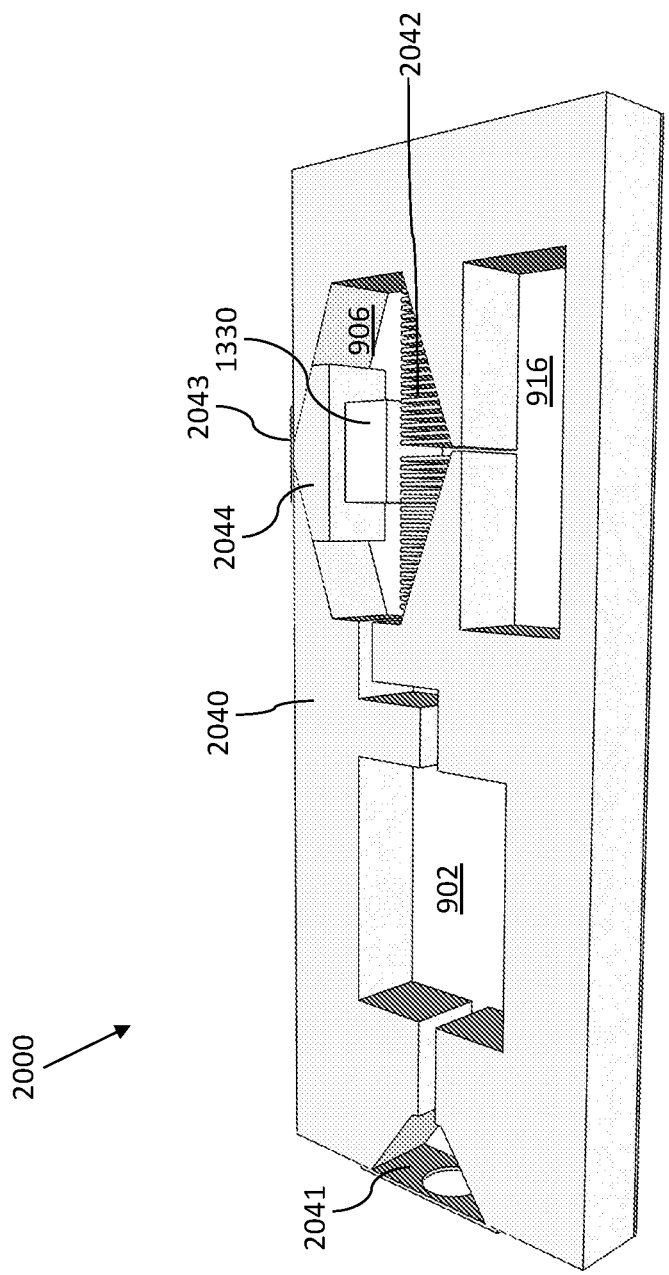
FIG. 20C illustrates a top perspective view of reactor 2000 for generating an antimicrobial gas.
Figure 20D:
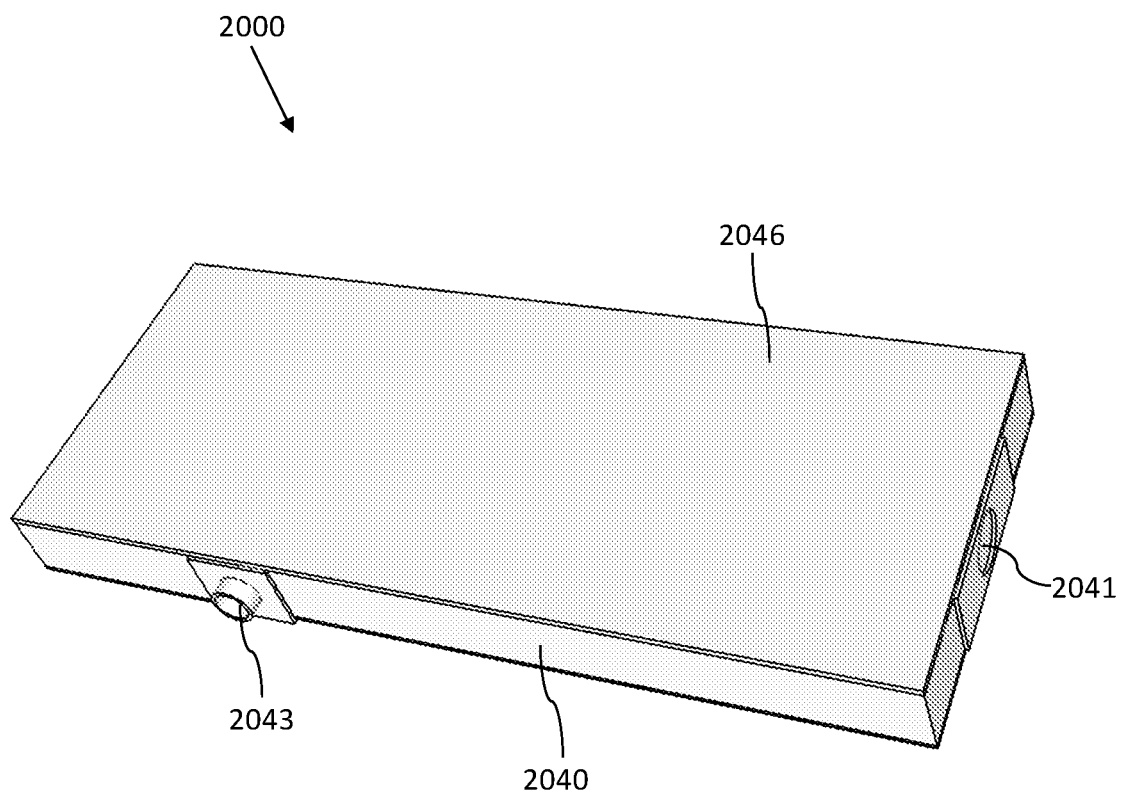
FIG. 20D illustrates a front perspective view of reactor 2000 for generating an antimicrobial gas.
Figure 21A:
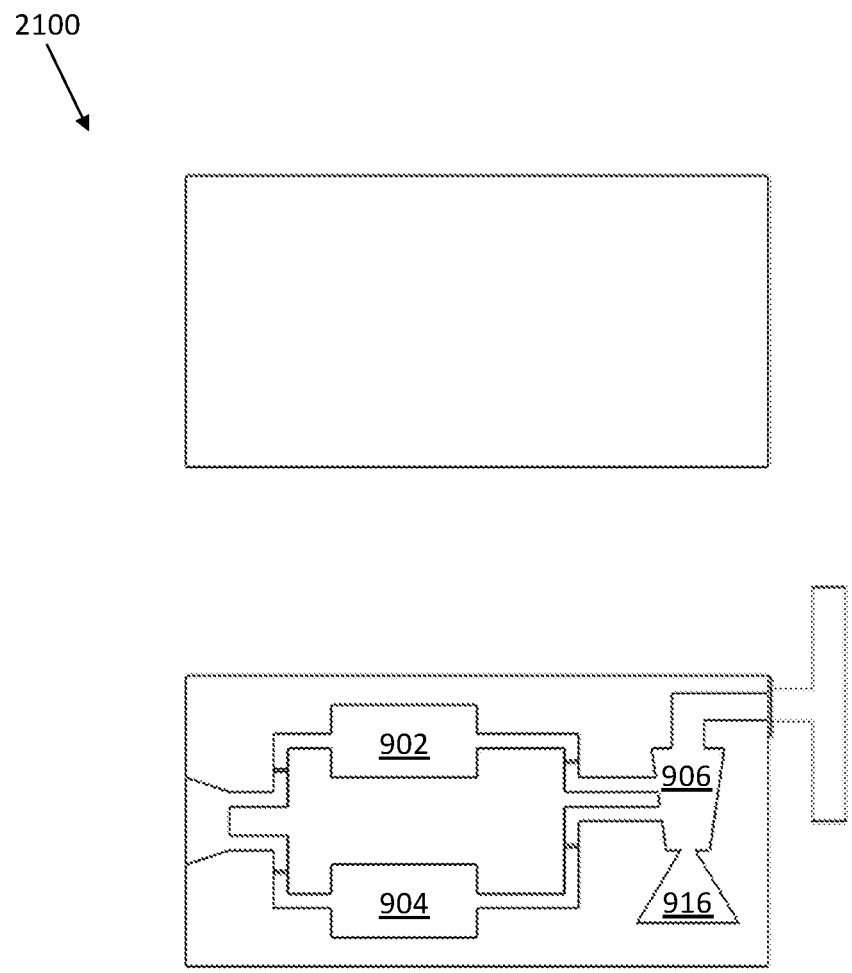
FIG. 21A illustrates a plan view of a reactor 2100 for generating an antimicrobial gas.
Figure 21B:
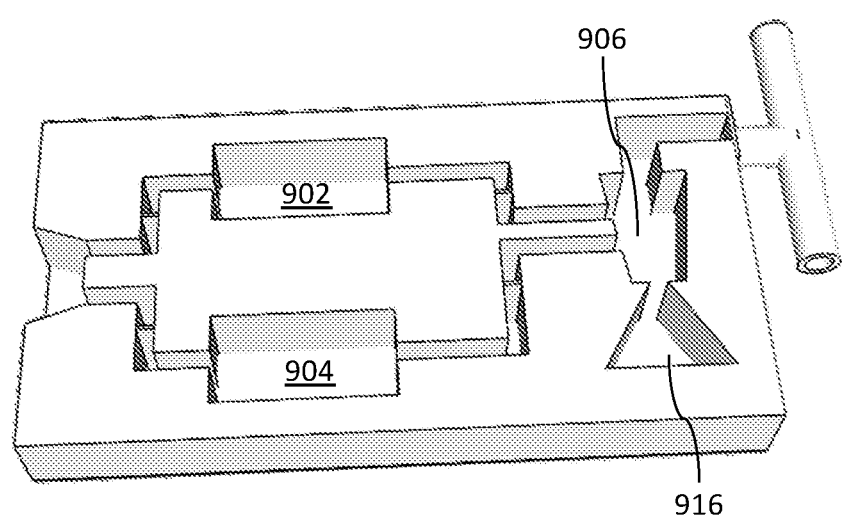
FIG. 21B illustrates a top perspective view of reactor 2100 for generating an antimicrobial gas.
Figure 21C:
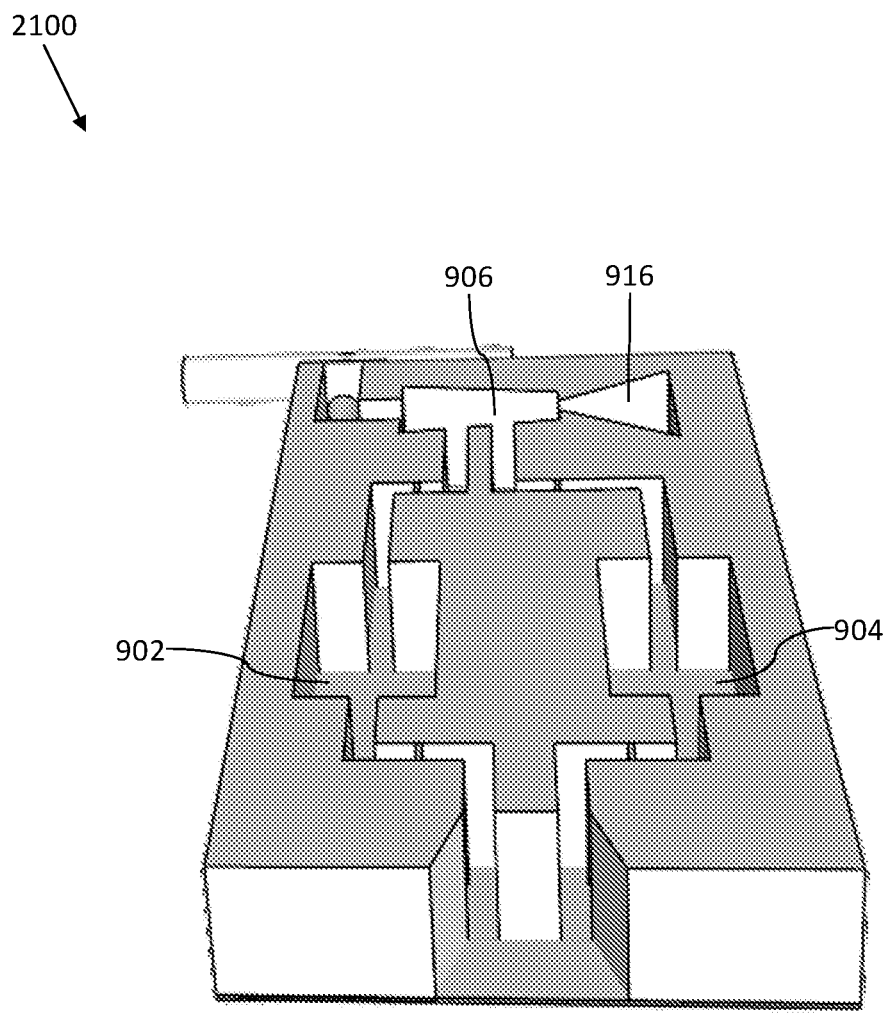
FIG. 21C illustrates a rear perspective view of reactor 2100 for generating an antimicrobial gas.
Figure 21D:
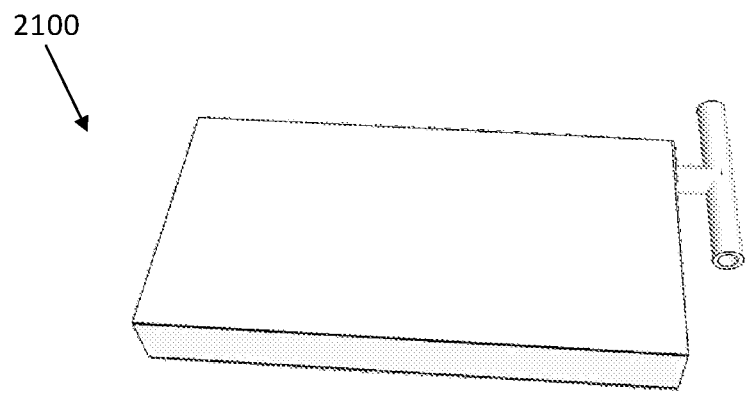
FIG. 21D illustrates a top perspective view of reactor 2100 for generating an antimicrobial gas.
Figure 21E:
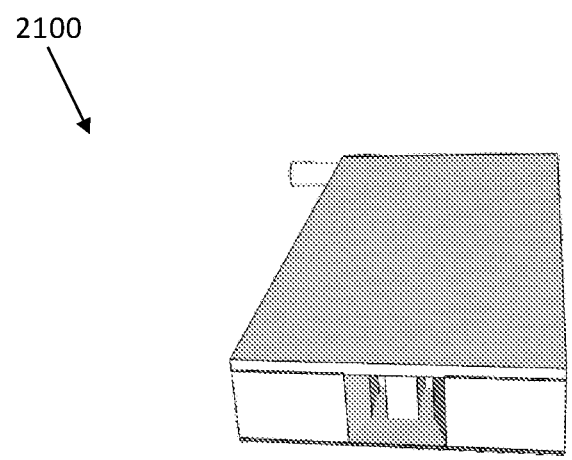
FIG. 21E illustrates a rear perspective view of reactor 2100 for generating an antimicrobial gas.
Figure 22A:
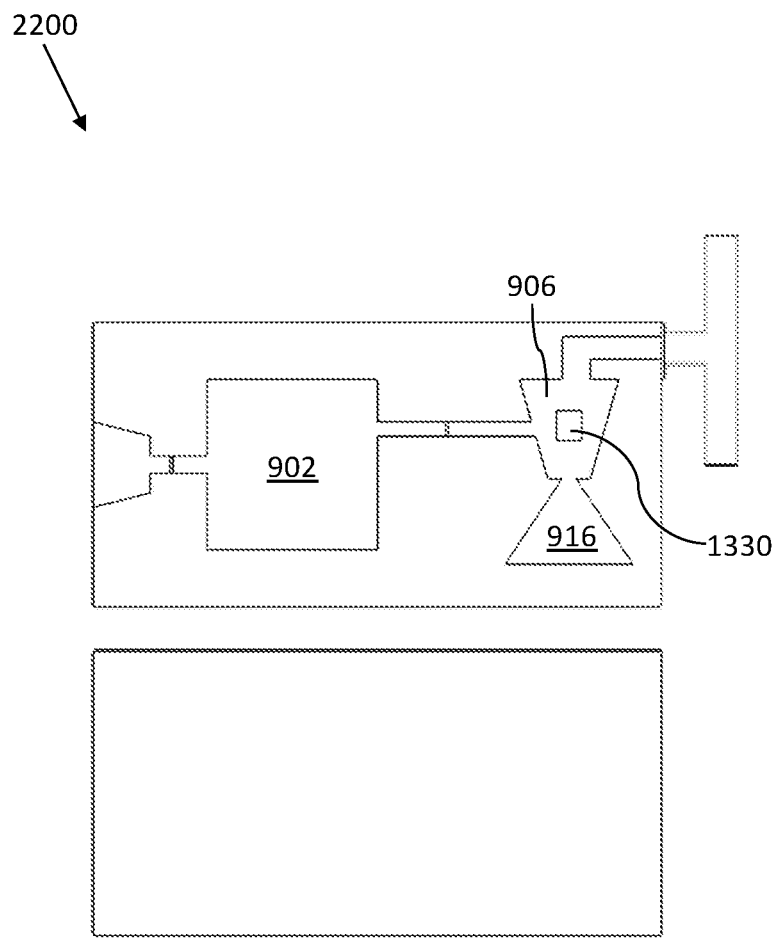
FIG. 22A illustrates a plan view of a reactor 2200 for generating an antimicrobial gas.
Figure 22B:
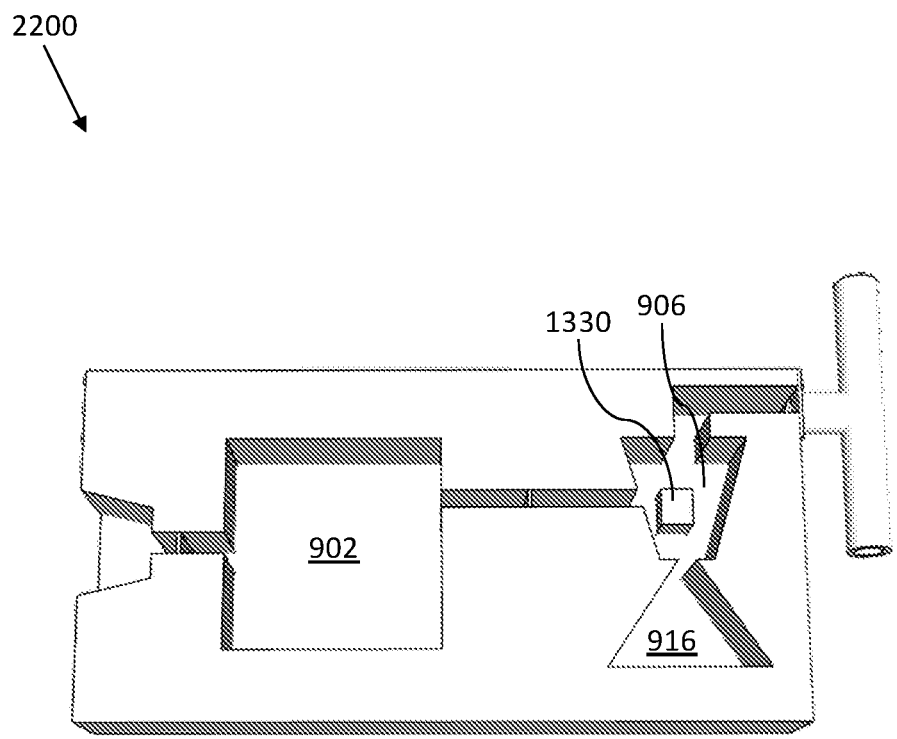
FIG. 22B illustrates a top perspective view of reactor 2200 for generating an antimicrobial gas.
Figure 22C:
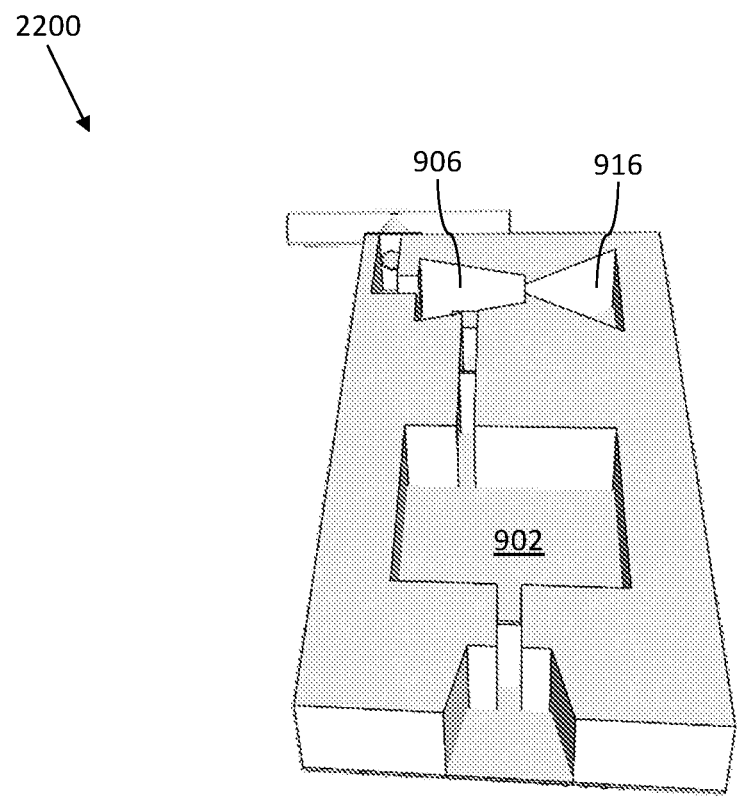
FIG. 22C illustrates a rear perspective view of reactor 2200 for generating an antimicrobial gas.
Figure 22D:
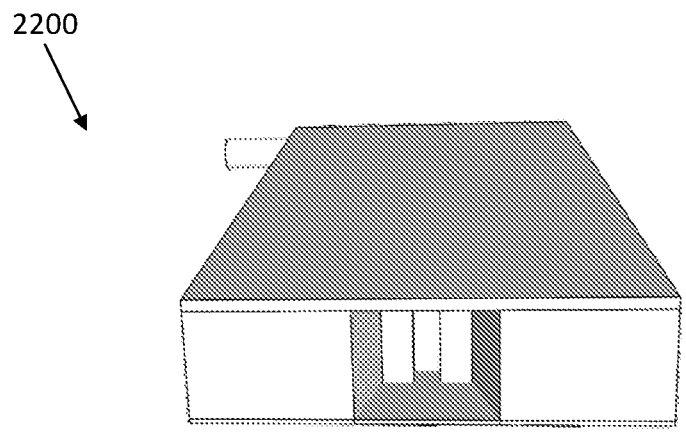
FIG. 22D illustrates a rear perspective view of reactor 2200 for generating an antimicrobial gas.
Figure 22E:
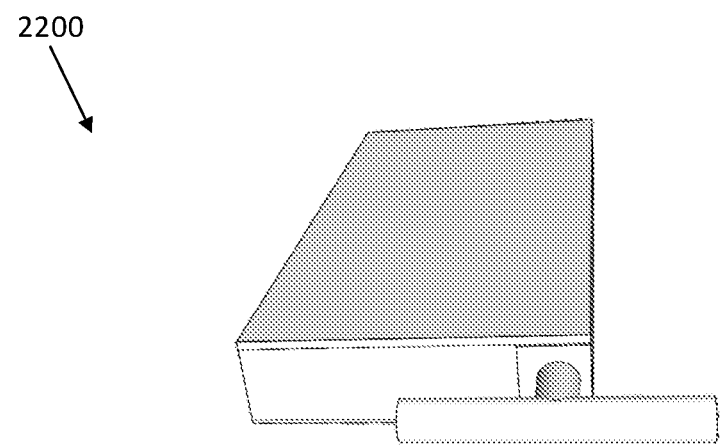
FIG. 22E illustrates a front perspective view of reactor 2200 for generating an antimicrobial gas.

As illustrated in FIG. 20D, reactor 2000 may include a cover 2046 that seals the above-referenced contents (e.g., liquid precursor 902, reaction chamber 906, and waste liquid container 916) within housing 2040.

FIGS. 23A-23G, and FIG. 24 illustrate an example antimicrobial gas (e.g., $ClO_2$ gas) generator 2300, 2400, respectively. Generator 2400 is substantially similar to generator 2300, but includes a second reagent container 2356, a second pressure generator 2366, and all associated ducts and passages to permit the second reagent to flow to a generation chamber 2374.

Antimicrobial gas (e.g., $ClO_2$ gas) generator 2300, 2400 may include a base 2354, at least one reagent container 2356 holding a liquid reagent 2358, and a reagent container lid 2360 with air permeable seal configured to prevent escape of liquid reagent 2358.

Within base 2354, at least one pressure chamber 2362 is oriented below at least one reagent container 2356, with at least one chamber passage 2364 in communication with pressure chamber 2362 and reagent container 2356. At least one pressure generator 2366 is oriented in communication with both pressure chamber 2362 and passage 2364, such that pressure generator 2366 can selectively block or unblock the entrance of chamber passage 2364 into pressure chamber 2362. Pressure generator 2366 is biased into a position by at least one biasing device 2368. Biasing device 2368 may be a common biasing device such as a spring. Biasing device 2368 may bias pressure generator 2366 into an open position. Biasing device 2368 may bias pressure generator 2366 into a closed position.

At least one fluid duct 2370 extends through base 2354 from pressure chamber 2362 to a microfluidic chip 2372. Microfluidic chip 2372 may include a generation chamber 2374. A generation duct 2376 may extend partly through base 2354 and partly through the wall of an off-gas and waste chamber 2378. Chamber 2378 may include an absorber material, an evaporator, or the like. Chamber 2378 may include an absorber material for absorbing spent reagent waste. Chamber 2378 may include an inactivator for waste. Chamber 2378 may include a gas permeable lid 2380 configured to allow the passage of antimicrobial gas (e.g., $ClO_2$ gas) out of chamber 2378. Lid 2380 may be a gas permeable membrane.

Each of the reagent container 2356, microfluidic chip 2372, and off-gas and waste chamber 2378 may be attached to and supported upon base 2354.

Figure 23A:
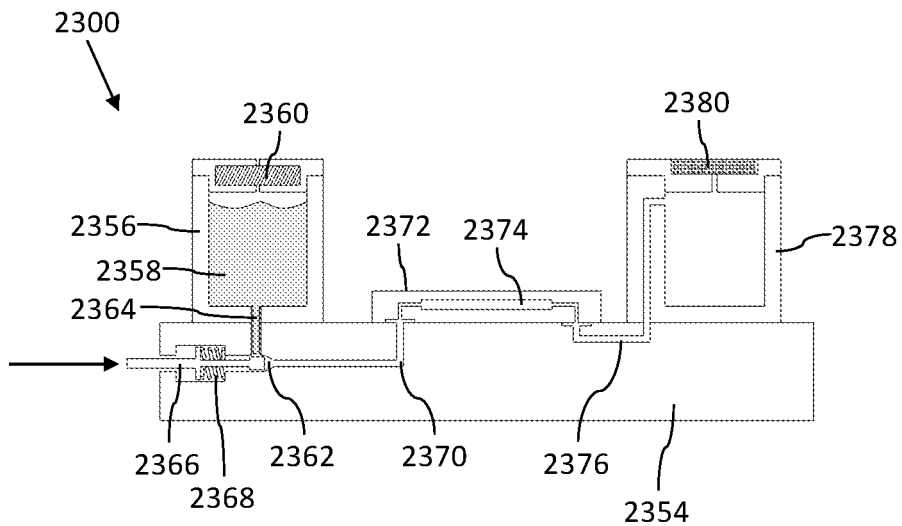
FIG. 23A illustrates a sectional view of an example antimicrobial gas generator 2300.
Figure 23B:
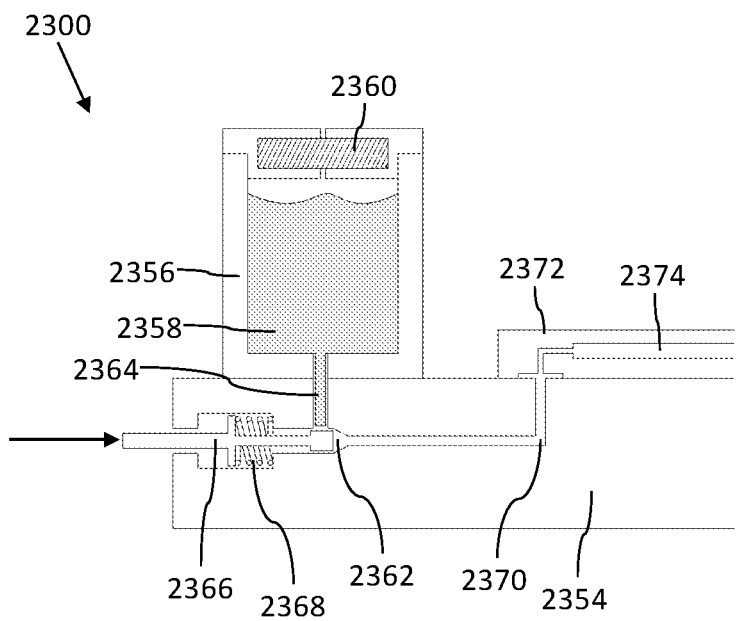
FIG. 23B illustrates a partial sectional view of antimicrobial gas generator 2300.
Figure 23C:
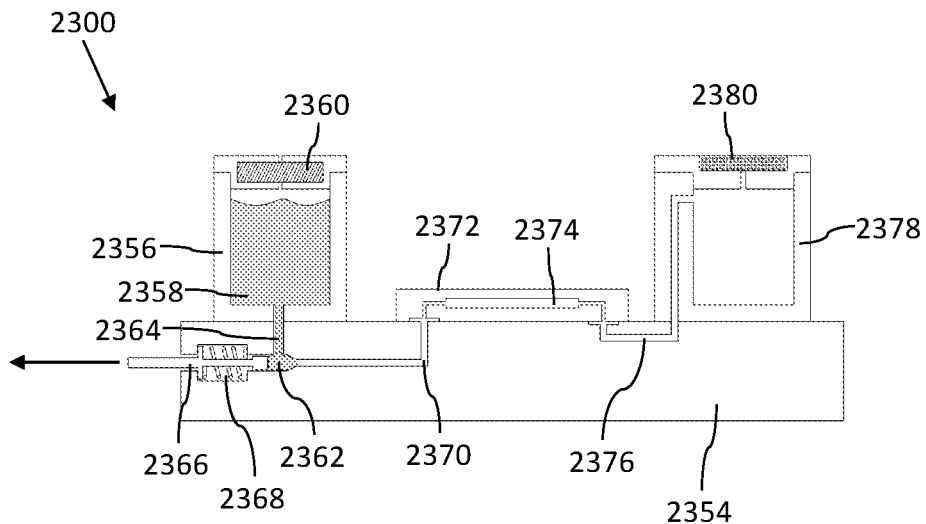
FIG. 23C illustrates a sectional view of antimicrobial gas generator 2300.
Figure 23D:
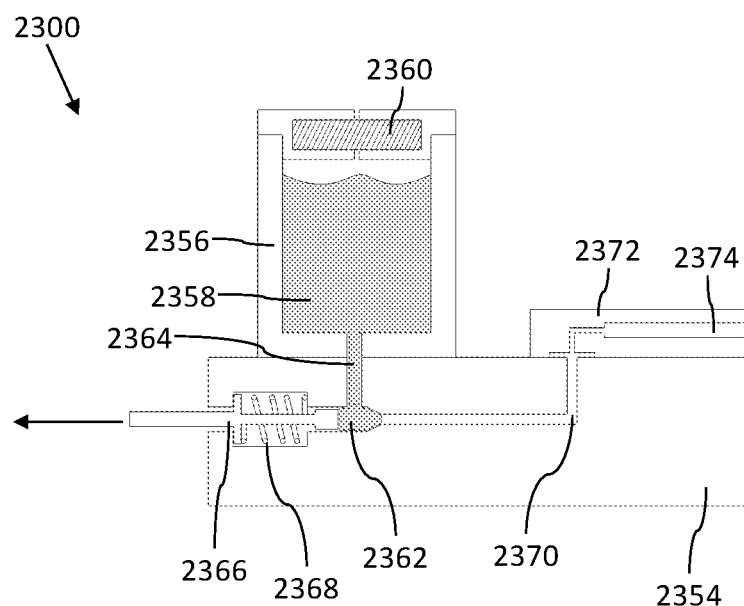
FIG. 23D illustrates a partial sectional view of antimicrobial gas generator 2300.
Figure 23E:
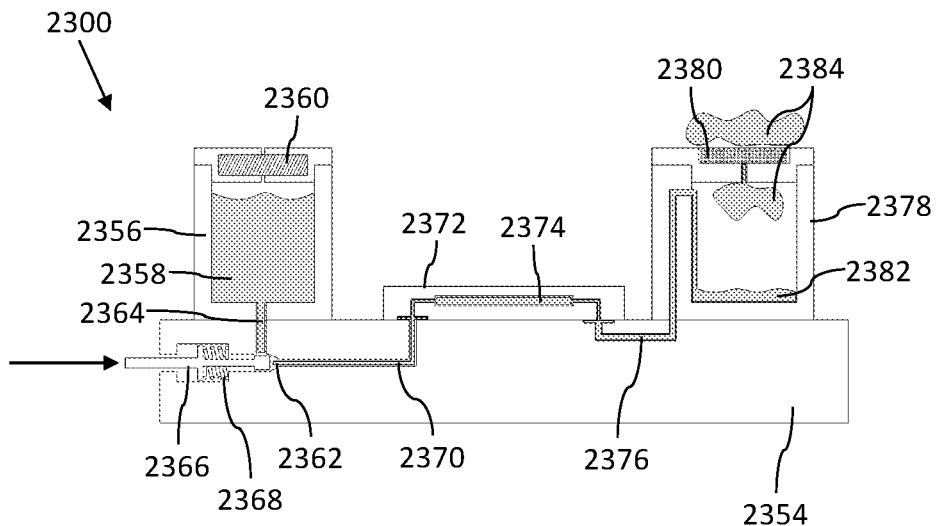
FIG. 23E illustrates a sectional view of antimicrobial gas generator 2300.
Figure 23F:
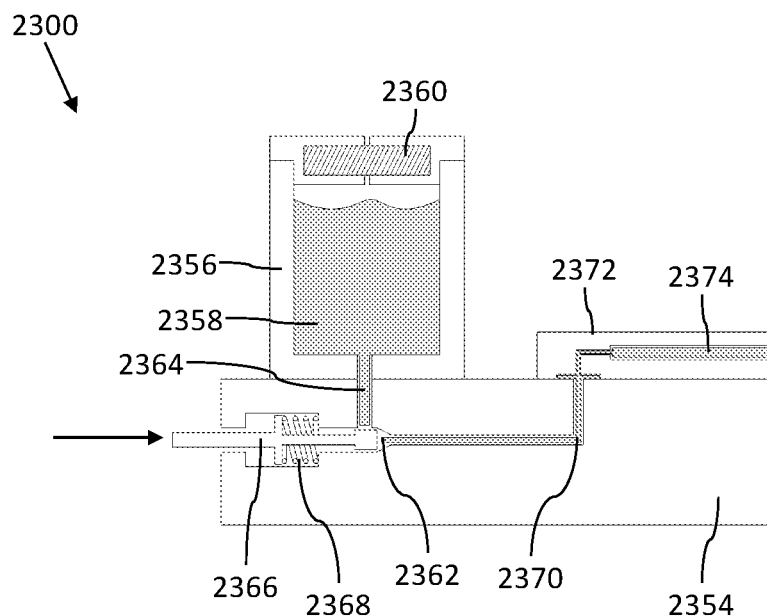
FIG. 23F illustrates a partial sectional view of antimicrobial gas generator 2300.
Figure 23G:
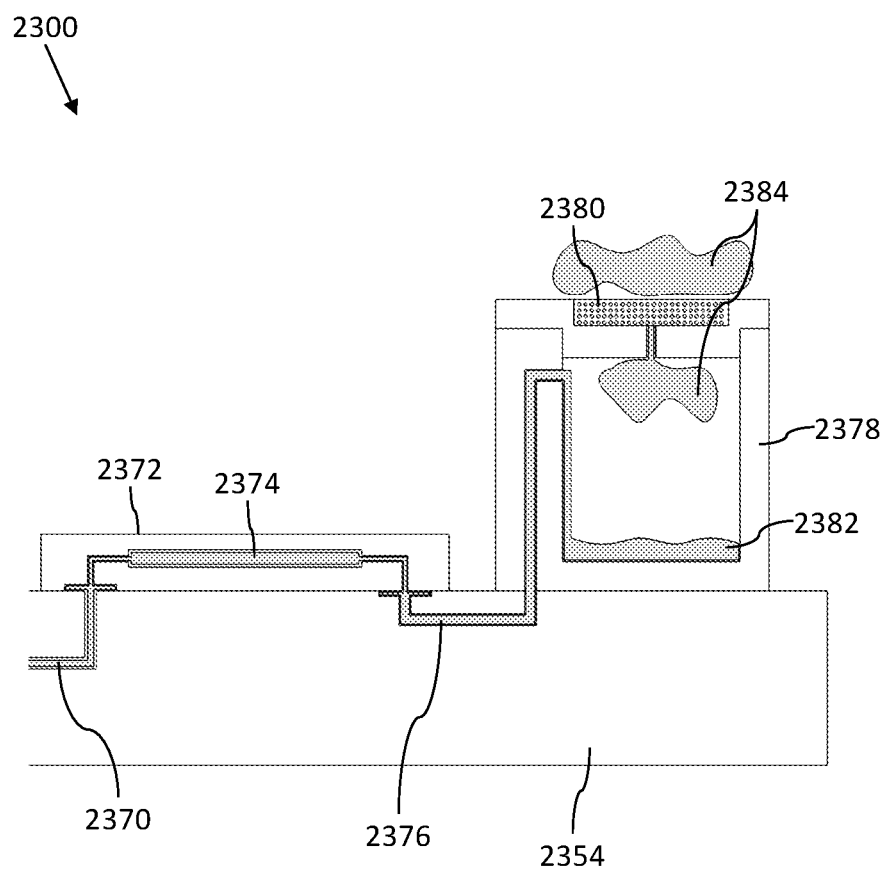
FIG. 23G illustrates a partial sectional view of antimicrobial gas generator 2300.

In operation, pressure generator 2366 begins in its closed position, as illustrated in FIGS. 23A and 23B. In this position, pressure generator 2366 seals chamber passage 2364, such that no liquid reagent 2358 may enter chamber 2362. Upon an instruction to generate antimicrobial gas (such as $ClO_2$ gas) (e.g., from a microcontroller such as microcontroller 306), pressure generator 2366 moves to its open position, as illustrated in FIGS. 23C and 23D. Liquid reagent 2358 passes out of reagent container 2356 and into pressure chamber 2362. Pressure chamber 2362 may be sized and shaped to permit a specific desired volume of liquid reagent 2358 to fill pressure chamber 2362 for transfer to microfluidic chip 2372. Finally, pressure generator 2366 moves back to its closed position, as illustrated in FIGS. 23E-23G, at once sealing chamber passage 2364 to prevent further introduction of liquid reagent 2358 from reagent container 2356, and pressurizing the liquid reagent within chamber 2362, so as to force the liquid reagent through the remainder of the system. Specifically, the liquid reagent is forced through fluid duct 2370, through generation chamber 2374, through generation duct 2376, and into off-gas and waste chamber 2378. Here, liquid waste 2382 is captured within chamber 2378, while antimicrobial gas (e.g., $ClO_2$ gas) 2384 passes through gas permeable lid 2380 and into the ambient environment.

It is understood that more than one cycle of pressure generator 2366 from its closed position, to its open position, and back to its closed position, may be required to push reagent 2358 completely through the system. Particularly, when antimicrobial gas (e.g., $ClO_2$ gas) generator 2300 is new, a few cycles of pressure generator 2366 may be required to begin generating antimicrobial gas (e.g., $ClO_2$ gas).

As illustrated in FIGS. 23A-23G, generator 2300 may include a single liquid reagent 2358 that enters generation chamber 2374 to generate an antimicrobial gas (e.g., $ClO_2$ gas). Thus, microfluidic chip 2372 may utilize a microfluidic electrochemical generator as described above.

Alternatively, as illustrated in FIGS. 23A-23G, generator 2300 may include a single liquid reagent 2358 comprising $NaClO_2$ that enters generation chamber 2374 where a solid activator is contained, thus generating an antimicrobial gas, such as $ClO_2$ gas.

Figure 24:
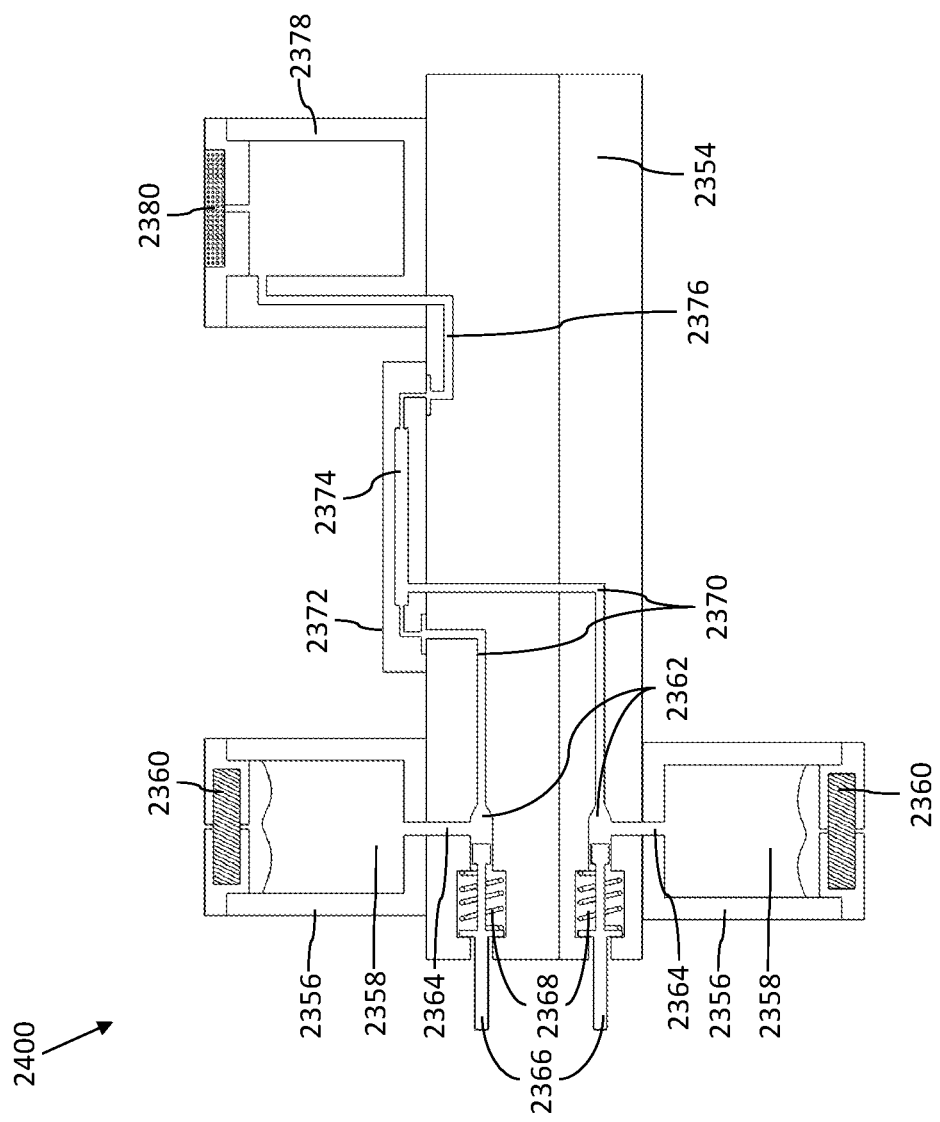
FIG. 24 illustrates a sectional view of an example antimicrobial gas generator 2400.
Figure 25A:
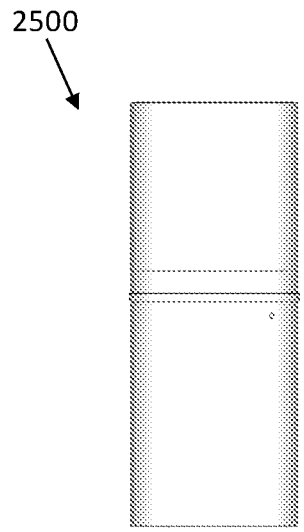
FIG. 25A illustrates an elevation view of an example antimicrobial gas generator and sensor device 2500.
Figure 25B:
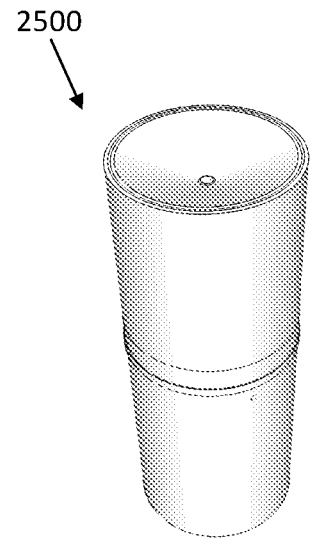
FIG. 25B illustrates a perspective view of antimicrobial gas generator and sensor device 2500.
Figure 25C:
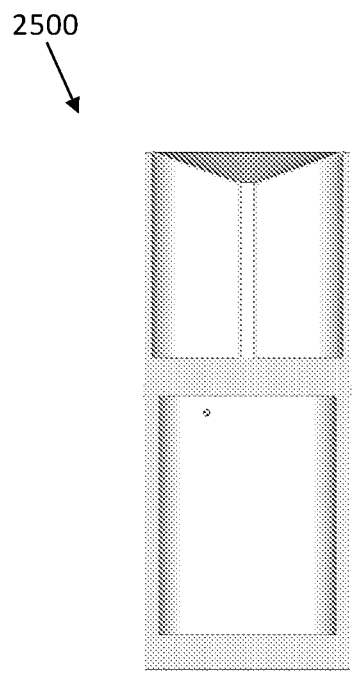
FIG. 25C illustrates a sectional view of antimicrobial gas generator and sensor device 2500.
Figure 26A:
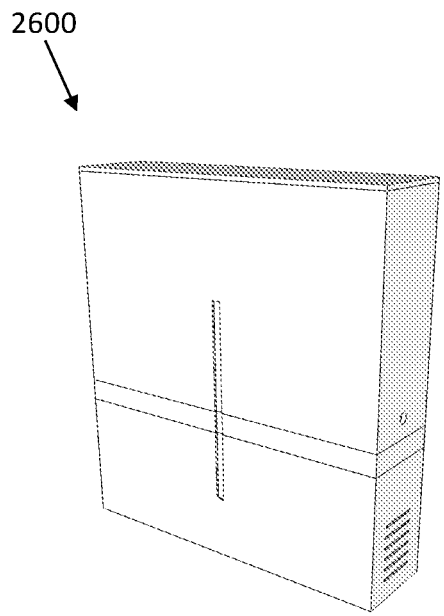
FIG. 26A illustrates a perspective view of an example antimicrobial gas generator and sensor device 2600.
Figure 26B:
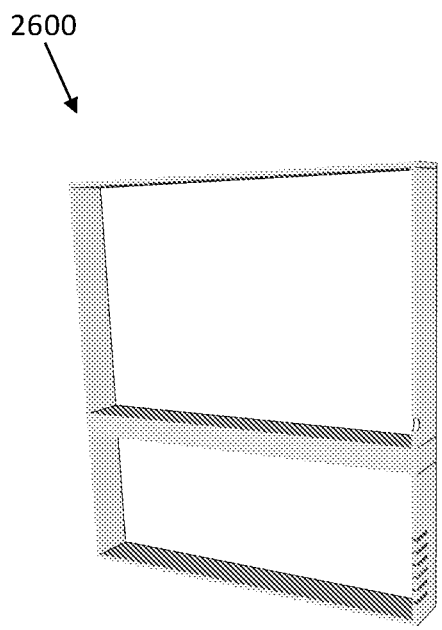
FIG. 26B illustrates a sectional view of antimicrobial gas generator and sensor device 2600.
Figure 27A:
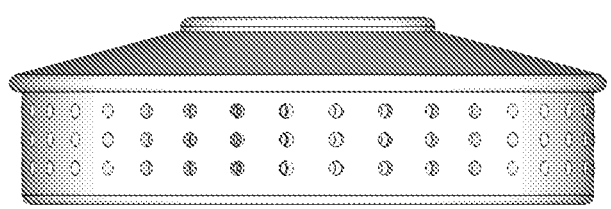
FIG. 27A illustrates an elevation view of an example antimicrobial gas generator and sensor device 2700.
Figure 27B:
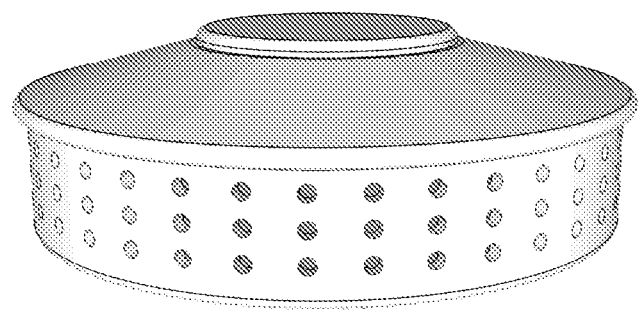
FIG. 27B illustrates a perspective view of antimicrobial gas generator and sensor device 2700.
Figure 28A:
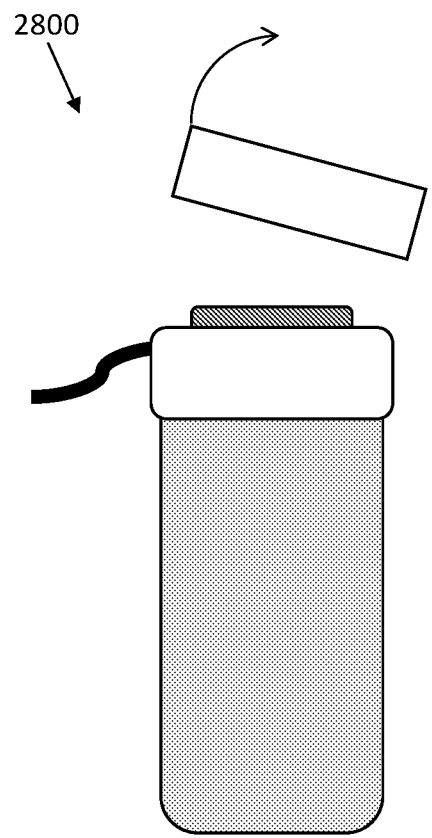
FIG. 28A illustrates an elevation view of an example portable antimicrobial gas reactor 2800.
Figure 28B:
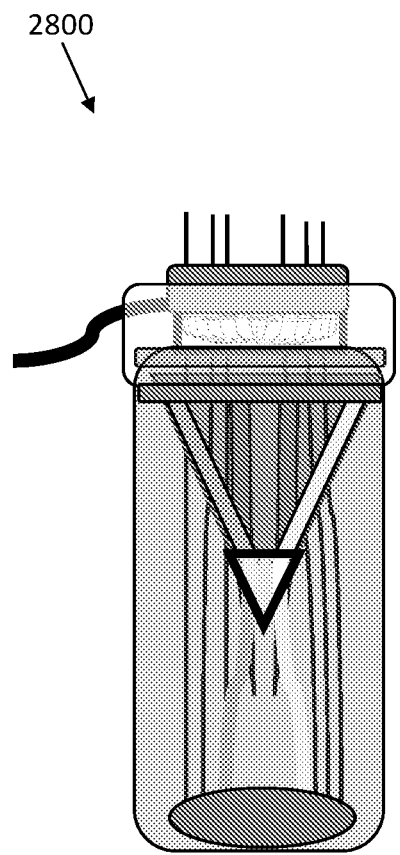
FIG. 28B illustrates a schematic view of portable antimicrobial gas reactor 2800.
Figure 29A:
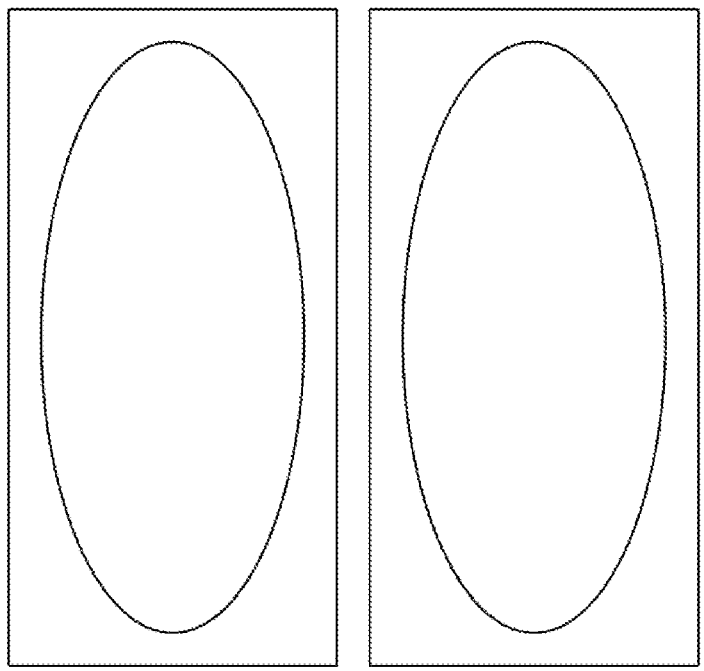
FIG. 29A illustrates a plan view of an example packaged antimicrobial gas generator solution and packaged activator solution.
Figure 29B:
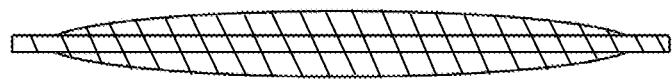
FIG. 29B illustrates a sectional view of packaged antimicrobial gas generator solution and packaged activator solution.
Figure 30A:
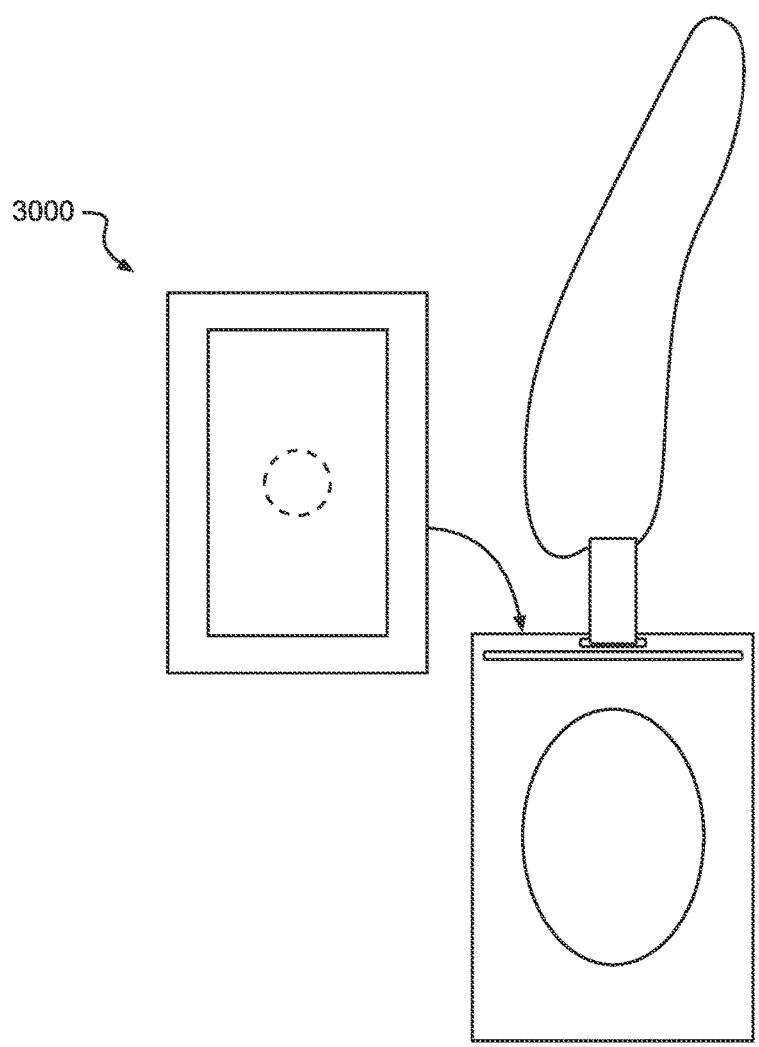
FIG. 30A illustrates an elevation view of an example of an antimicrobial gas generator 3000 in the form of a card shape or a sheet.
Figure 30B:
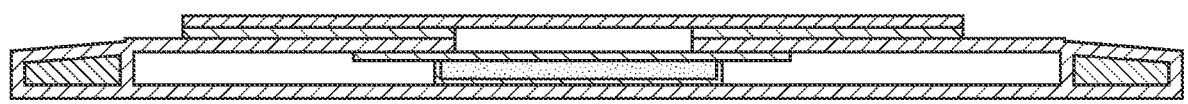
FIG. 30B illustrates a sectional view antimicrobial gas generator 3000 containing an antimicrobial generating compound.
Figure 31:
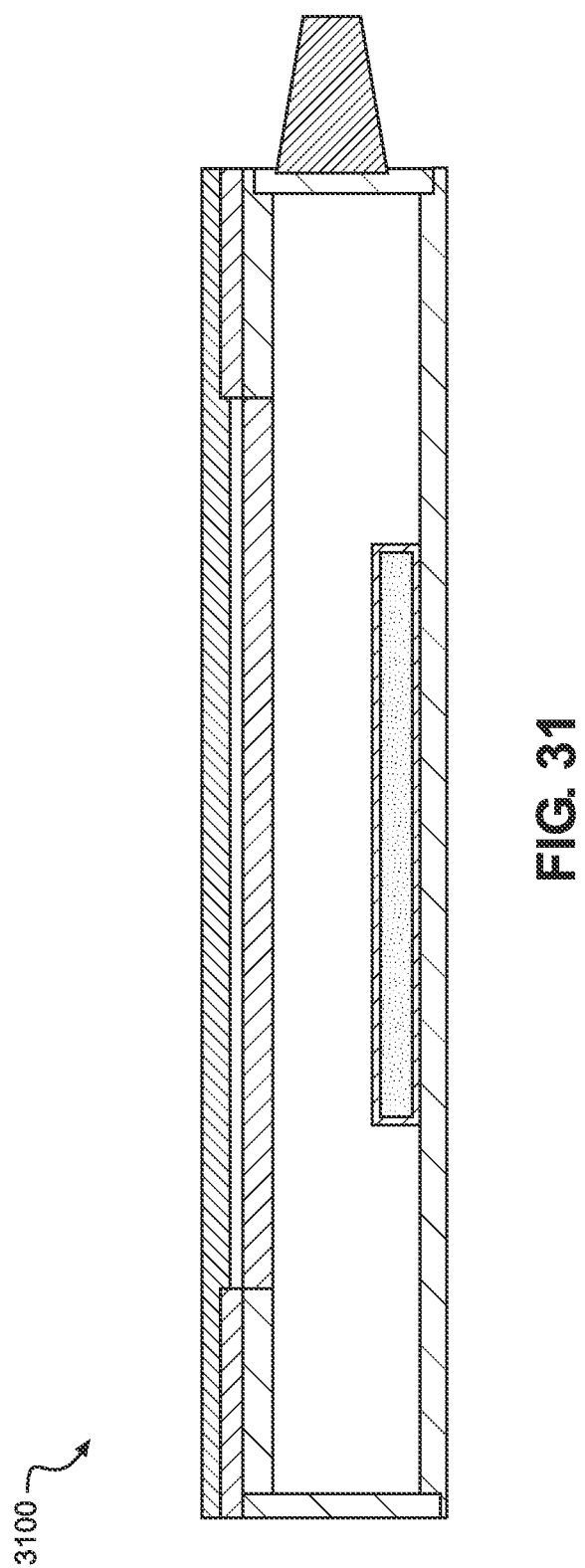
FIG. 31 illustrates an example of an antimicrobial generator 3100 in the form of a pouch with optional addition of water internal to the pouch.
Figure 32E:
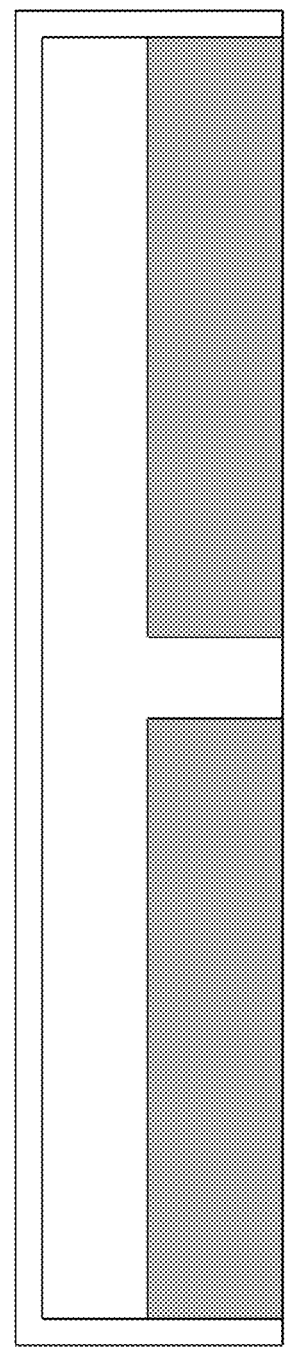
FIG. 32E illustrates an example of antimicrobial generator 3200 where reagent materials of FIGS. 32A-32C are configured side by side with optional materials to support activation and control release.
Figure 33A:
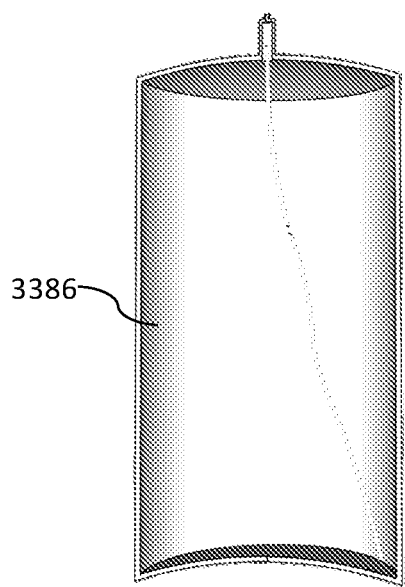
FIG. 33A illustrates a cutaway view of an aerosol container 3386 including an interrupted dip tube.
Figure 33B:
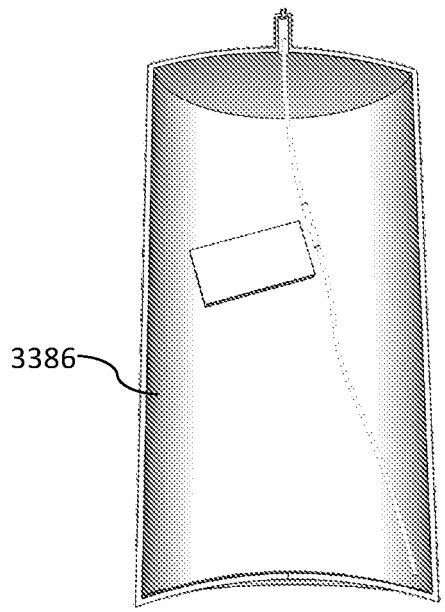
FIG. 33B illustrates a cutaway view of aerosol container 3386 including reactor engaged with dip tube.
Figure 33C:
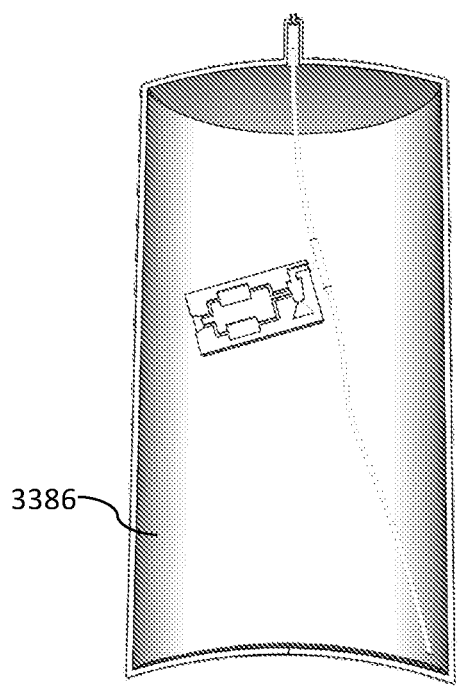
FIG. 33C illustrates a cutaway view of aerosol container 3386 including reactor engaged with dip tube.
Figure 33D:
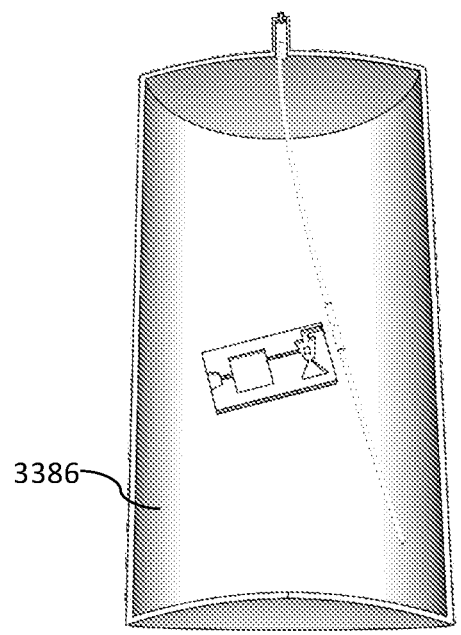
FIG. 33D illustrates a cutaway view of aerosol container 3386 including reactor engaged with dip tube.
Figure 34:
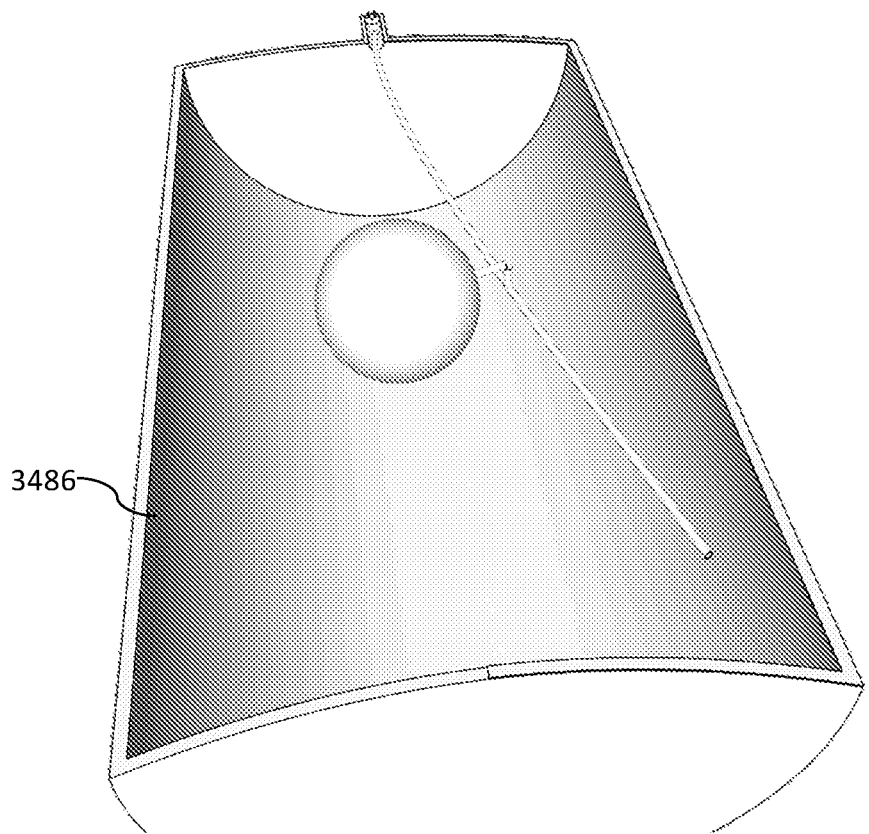
FIG. 34 illustrates a cutaway view of an aerosol container 3486 including a flexible bladder connected to a dip tube.
Figure 35A:
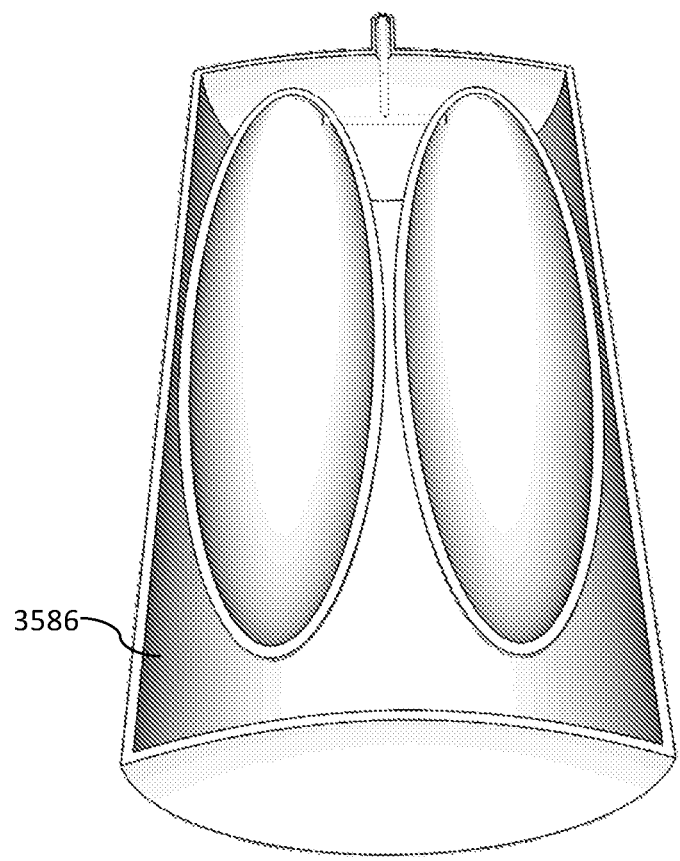
FIG. 35A illustrates a cutaway view of an aerosol container 3586 including a plurality of flexible bladders.
Figure 35B:
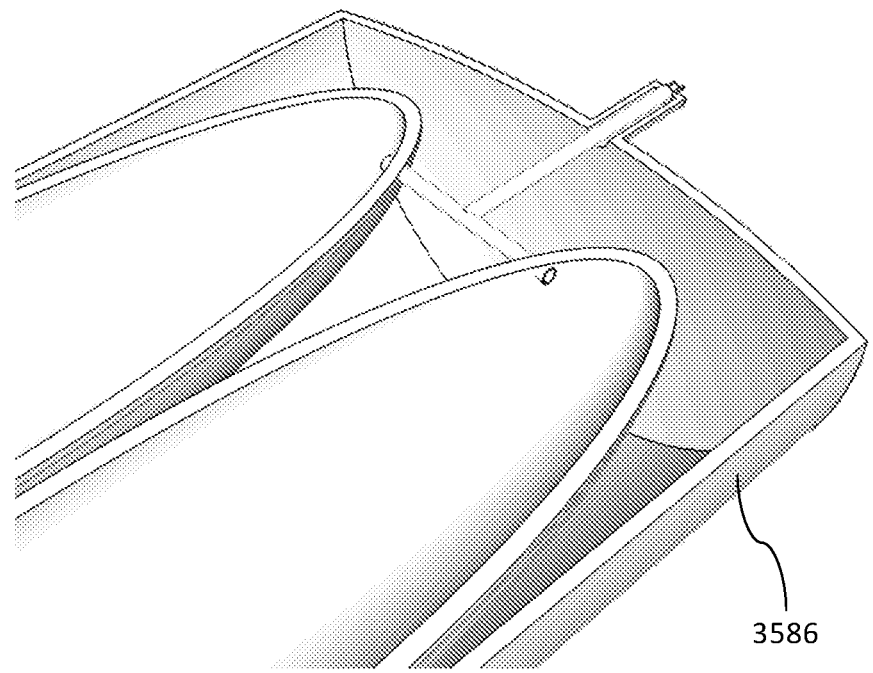
FIG. 35B illustrates a cutaway view of aerosol container 3586 including a plurality of flexible bladders.
Figure 36:
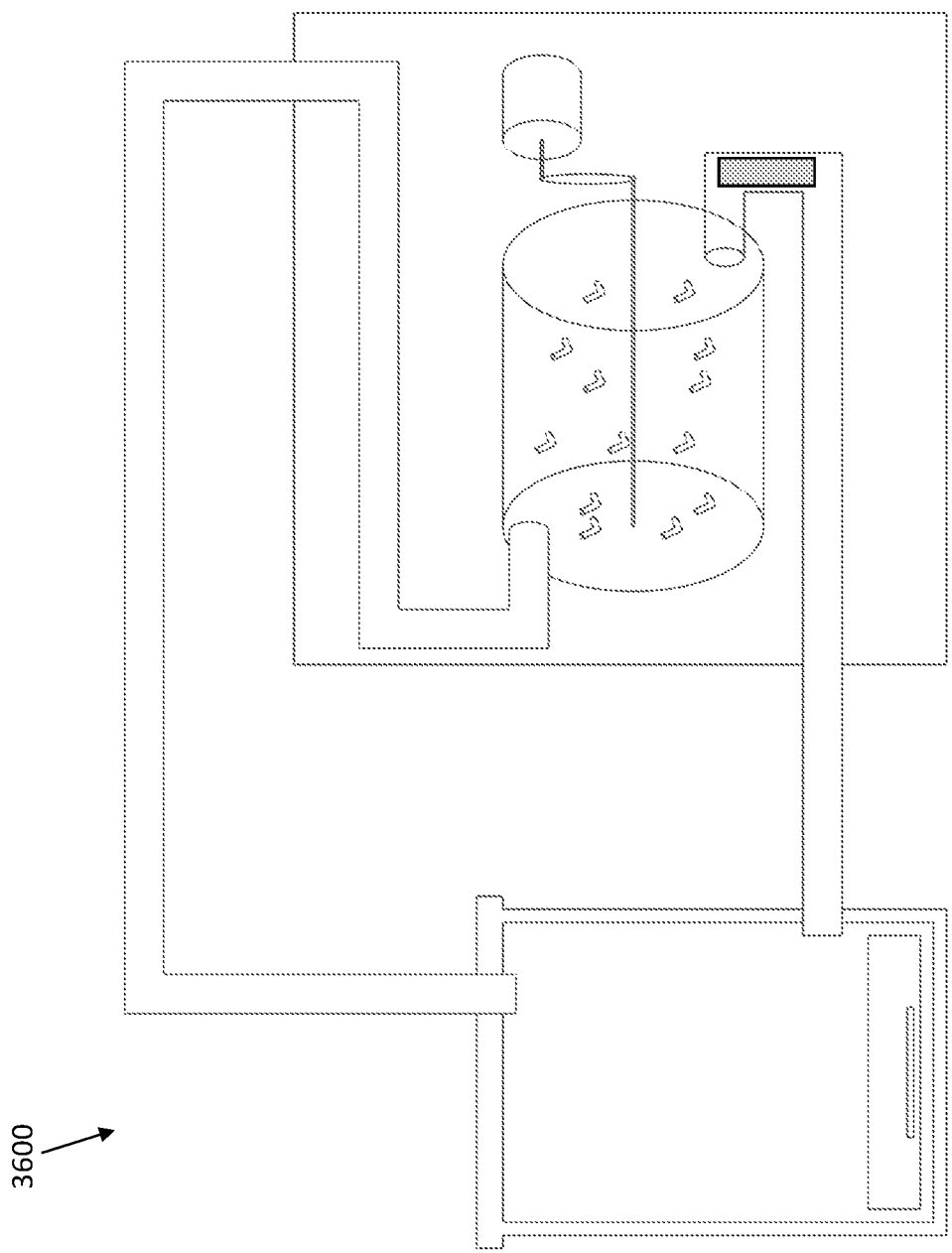
FIG. 36 illustrates a schematic diagram of an apparatus 3600 for generating antimicrobial gas or vapor external to a sealed environment for disinfecting items therein.

Alternatively, as illustrated in FIG. 24, generator 2400 may include two separate reagent containers 2356, with two separate pressure chambers 2362, two separate pressure generators 2366, and two separate fluid ducts 2370, such that the two separate liquid reagents enter generation chamber 2374 separately where they combine and mix to generate antimicrobial gas (e.g., $ClO_2$ gas).

Pressure generator 2366 may be actuated via a connection to an actuator (not shown), including for example an electric motor, including an electric step motor, or the like. Pressure generator 2366 may be a plunger and may generate pressure via translation fore and aft (longitudinally).

Pressure generator 2366 may be, and translate in a direction, coaxial with chamber 2362 and fluid duct 2370. Pressure generator 2366 may be oriented at, and translate in a direction at, an angle to chamber passage 2364. In one aspect, pressure generator 2366 translates along an axis that is at a right angle (90 degrees) from the axis of chamber passage 2364.

Generator 2300, 2400 may include one or more control valves (not shown) in communication with pressure generator(s) 2366 and/or reagent container(s) 2356. Likewise, one or more control valve (not shown) may be in communication with chamber passage(s) 2364 and microfluidic chip 2372. These valves may selectively permit, prevent, or otherwise control the flow of reagents into generation chamber 2374. Generator 2300, 2400 may include a sensor system for determining the quantity, mass, volume, or the like of reagents transiting chamber passage(s) 2364.

As such, while these alternative embodiments are not illustrated, they are contemplated and as such, the figures are not intended to be limiting.

Antimicrobial Distribution Systems and Devices

Figure 37:
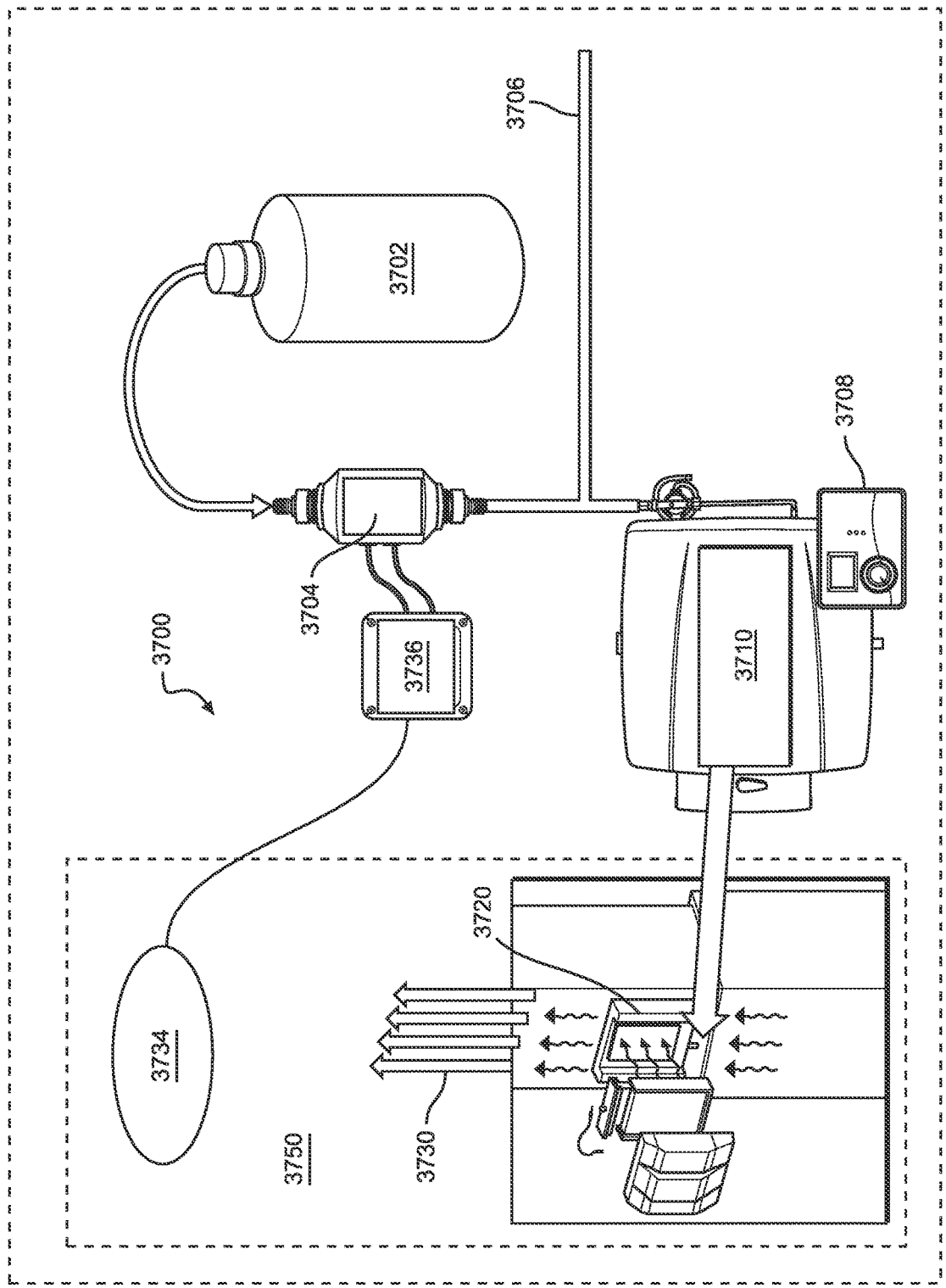
FIG. 37 illustrates a schematic diagram of a system 3700 generating antimicrobial gas or vapor external to a sealed environment for disinfecting items therein.
Figure 38A:
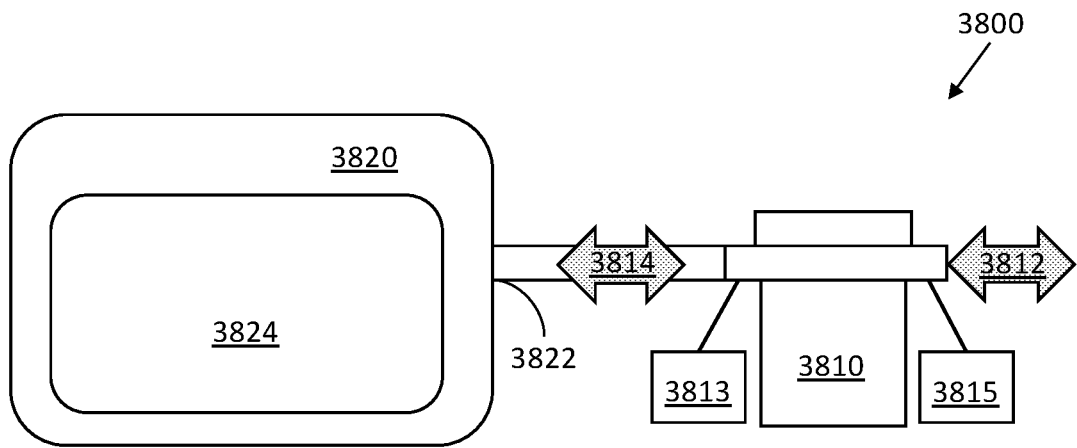
FIG. 38A illustrates a schematic diagram of a system 3800 generating antimicrobial gas or vapor within a sealed environment for disinfecting items in the sealed environment.
Figure 38B:
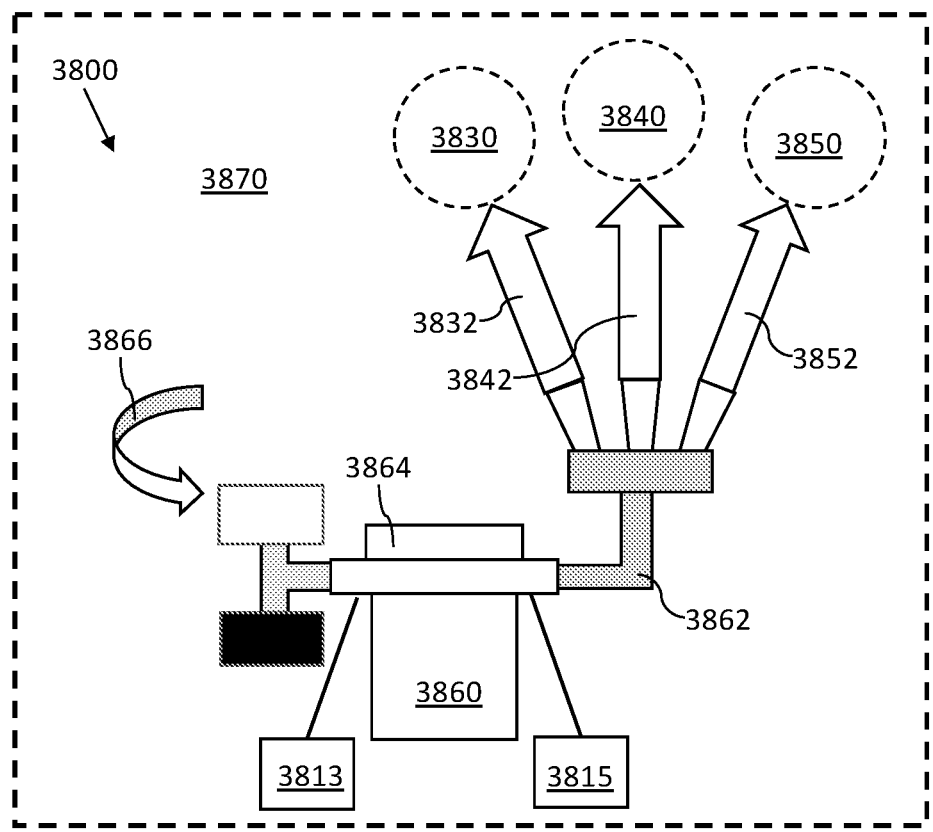
FIG. 38B illustrates a schematic diagram of apparatus 3800 generating antimicrobial gas or vapor within a sealed environment for disinfecting items in the sealed environment.
Figures 39A, 39B, 39C:
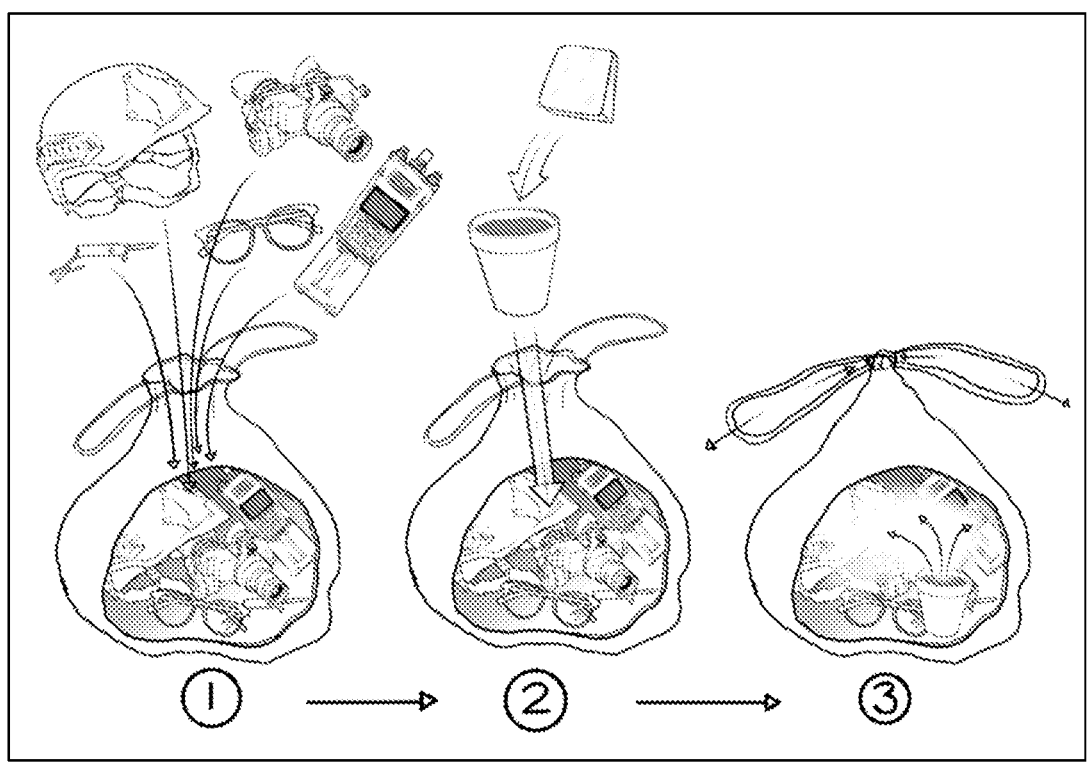
FIG. 39A illustrates an apparatus 3900 generating antimicrobial vapor within a sealed environment for disinfecting items therein.
FIG. 39B illustrates apparatus 3900 generating antimicrobial vapor within a sealed environment for disinfecting items therein.
FIG. 39C illustrates apparatus 3900 generating antimicrobial vapor within a sealed environment for disinfecting items therein.
Figure 40:
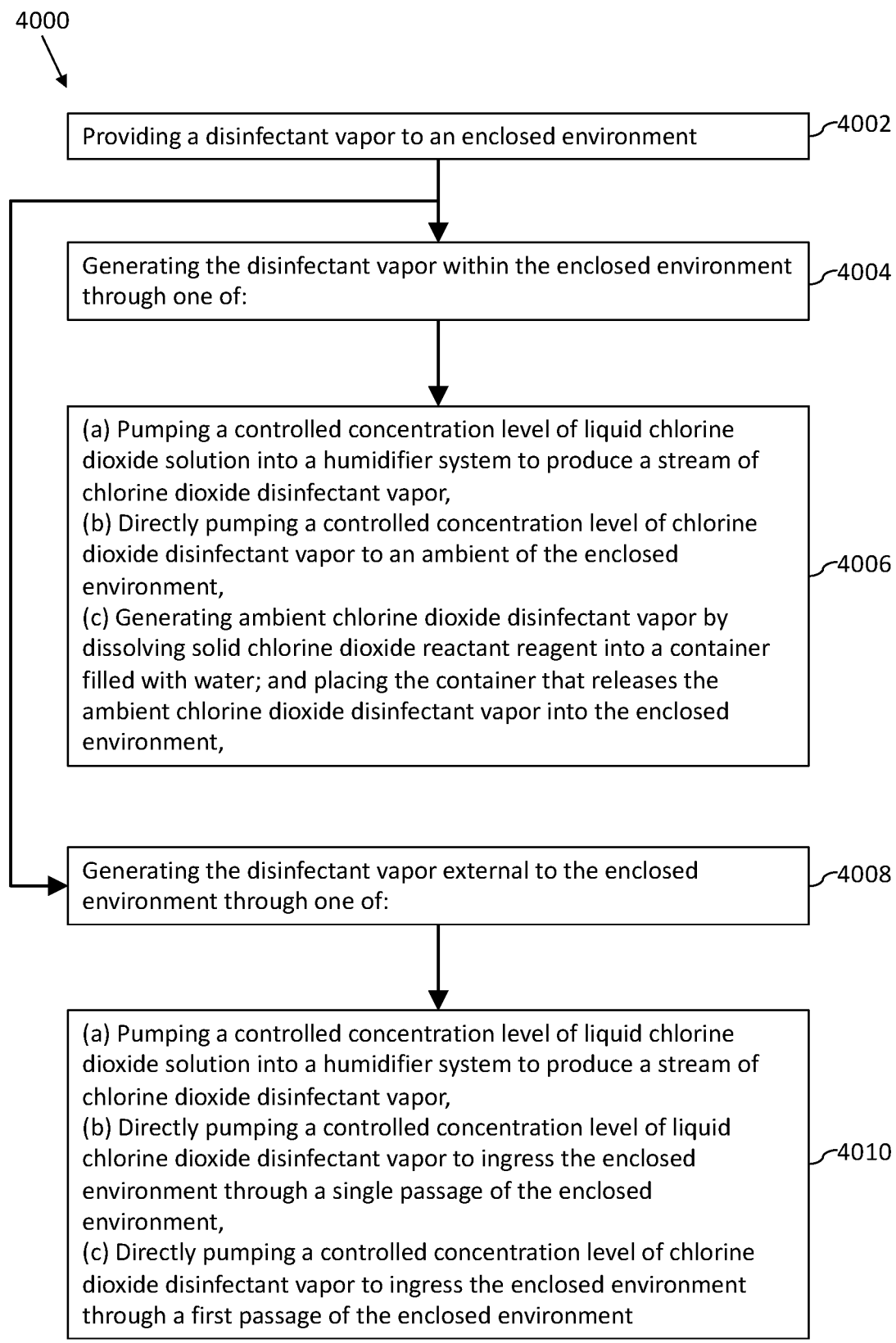
FIG. 40 illustrates methods of generating antimicrobial gas or vapor within a sealed environment or external to the sealed environment to disinfect items within the sealed environment.
Figure 41A:
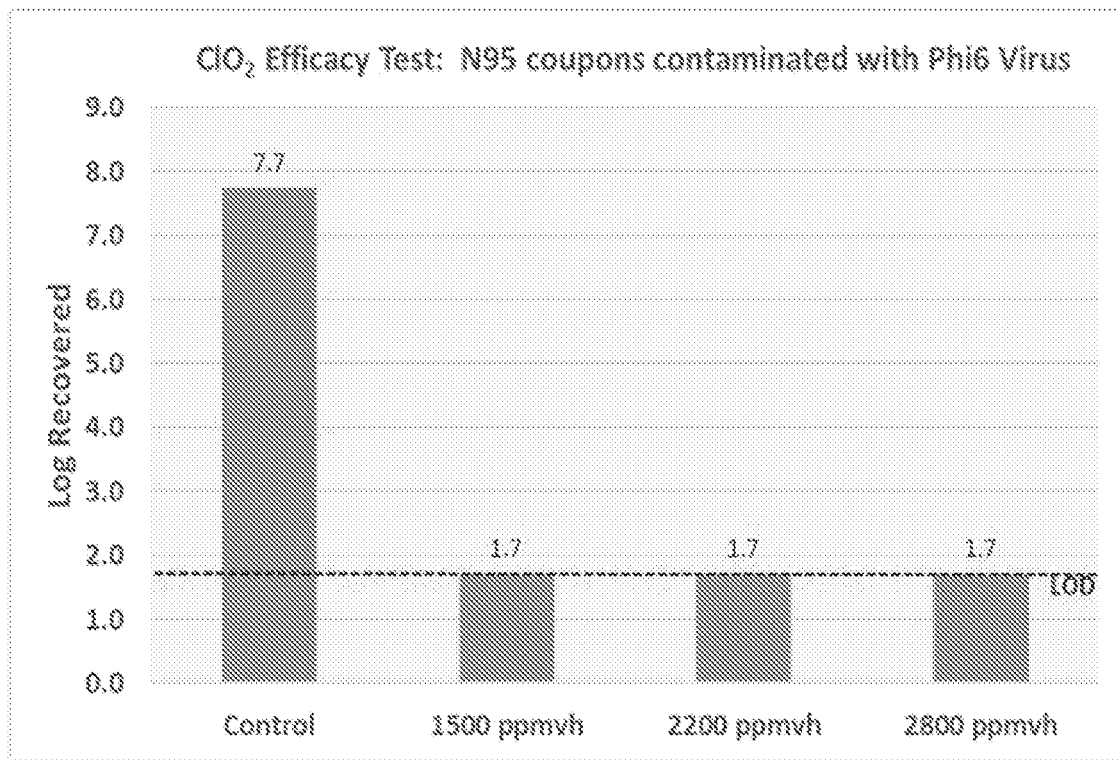
FIG. 41A illustrates $ClO_2$ efficacy test data on controlled samples.
Figure 41B:
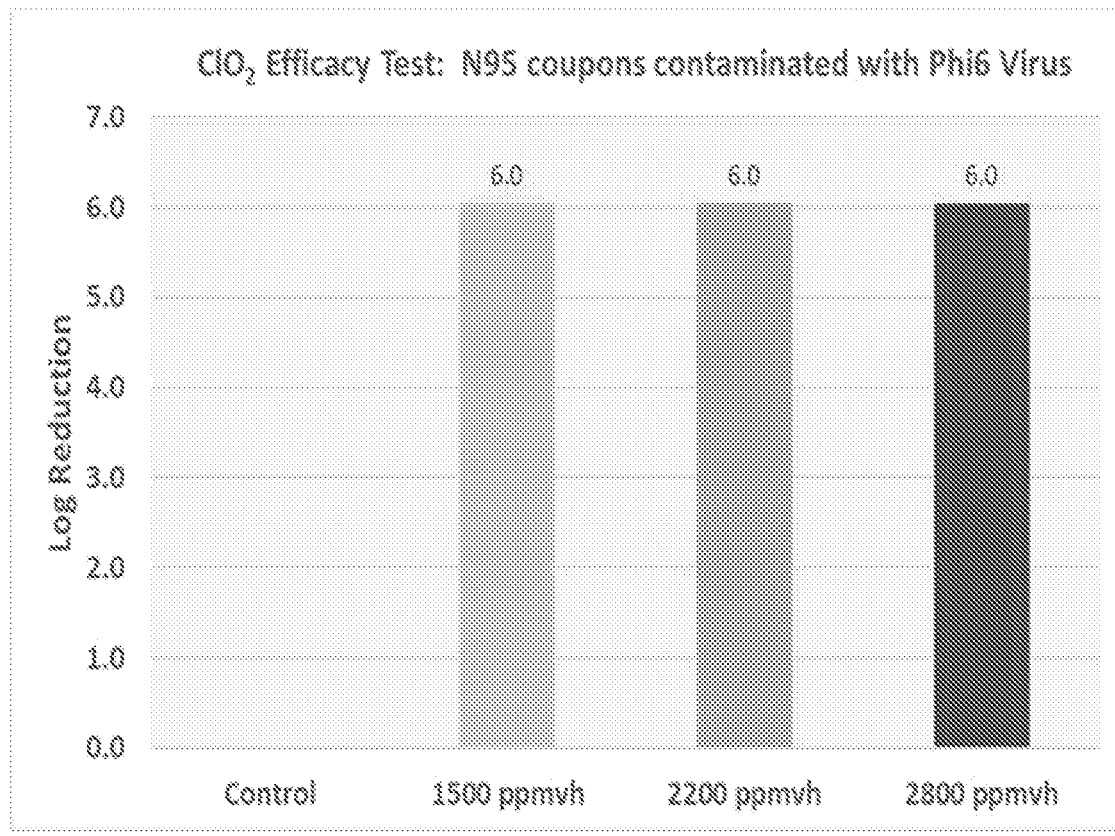
FIG. 41B illustrates $ClO_2$ efficacy test data on controlled samples.

FIG. 37 illustrates a system 3700 generating antimicrobial gas or vapor external to a sealed environment for disinfecting items therein. FIGS. 38A and 38B illustrate a system 3800 generating antimicrobial gas or vapor within a sealed environment for disinfecting items in the sealed environment. FIG. 40 illustrates methods of generating antimicrobial gas or vapor within a sealed environment or external to the sealed environment to disinfect items within the sealed environment. FIGS. 41A and 41B illustrate $ClO_2$ efficacy test data on controlled samples.

As used herein, the term "items" may include both personal protective equipment ("PPE") and non-PPE items, such as personal items, garments, medical equipment, apparel, garments, shoes, personal electronic devices, furniture, office supplies, built-in structures, drapes, fabrics, utensils, fixtures, decorative items, food, and plants. In addition, the term "sealed environment" may include any of: a sealable bag, a tent, a storage container, a drum, a tumbler drum, a chamber, a room, an office, a store, a warehouse, a home, a hospital, a floor of a multi-level building, a cabin, an aircraft cabin, a vehicle cabin, a shipping container, a surface vessel cabin, an underwater vessel cabin, public transportation vehicles.

Apparatuses/systems 3700 and 3800 utilize an antimicrobial gas, such as chlorine dioxide ($ClO_2$) gas, for disinfecting PPE including, without limitation, N95 respirators, surgical masks, protective suits, goggles, and helmets, making them safe for reuse by healthcare professionals and patients, as well as personal items and facilities in office and home settings. In addition, the disclosed methods and apparatuses may be applicable to general decontamination of contained spaces and items.

The technology has been shown effective against an Ebola surrogate on common hard surface and porous household materials and as a broad-spectrum chemical and biological decontaminant for sensitive equipment. The feasibility of disinfecting and reusing N95 masks has previously been demonstrated using hydrogen peroxide gas or vapor, but the need for specialized (and expensive) equipment requires moving used/contaminated N95 masks to a single location for treatment.

With the proposed approach, used N95s may be placed in a sealable chamber and exposed to the headspace of an antimicrobial gas (e.g., $ClO_2$ solution, generated on-site and at the time of use). After a short antimicrobial gas generation period, dissolved antimicrobial gas is off-gassed within the chamber, allowing the antimicrobial gas to penetrate and disinfect the respirators. After a sufficient disinfection period, the liquid and gas disinfection solution (e.g., $ClO_2$) are neutralized before opening the chamber to retrieve the disinfected N95s. Neutralization may be performed by adding a small quantity of neutralizing agent, such as a non-hazardous dry chemical packaged with the kit. The spent disinfection solution and any packaging materials are then disposed as non-hazardous waste. The system design is very scalable, from a single item construct for small batches (approx. 1-20 respirators) to a room-size chambers or dedicated rooms for large batches (hundreds or thousands of N95s) for use at treatment facilities, forward operating bases, or hospitals to treat large numbers of N95 masks and other equipment. The method requires no electricity, and the decontamination kit (including the reactive ingredients and a container, such as a plastic bag) can be easily transported with other field equipment. Optionally, gas dispersion units ("GDU") within large room-size chambers for dedicated rooms for large batches may include fans or blowers to accelerate the liberation of $ClO_2$ while forcing $ClO_2$ out into the enclosure for faster and more uniform distribution. The GDU may require very little power (e.g., may be operated with a battery).

Preliminary efficacy testing (FIGS. 41A and 41B) has been conducted by contaminating nine coupons cut from an N95 with 7.7-logs of Phi6 bacteriophage (surrogate for Coronavirus and Ebola) prepared in an organic test soil. Coupons were exposed to $ClO_2$ gas generated from 6 liters of a 180 ppm $ClO_2$ solution in an 82-L container. A small fan was directed across the surface of the $ClO_2$ solution to aid in off-gassing and mixing. Coupons were removed after 1.50, 2.25, and 3.00 hours; the exposure times correspond to three treatment levels: 1500, 2200, and 2800 ppm-hours, respectively. Control coupons were held under ambient conditions for the duration of the experiment (3 hours). After treatment, the coupons were assayed; for all three treatment levels, no virions were recovered from the coupons treated with $ClO_2$ gas. For all three treatment levels, a 6-log reduction of virons was observed. FIGS. 41A and 41B show the recovered virions and log reduction observed for each treatment level. The limit of detection (LOD) for this assay was 1.7-logs. Based on this initial test, $ClO_2$ gas was effective against the Phi6 surrogate and 6-log reduction was achieved in less than 90 minutes.

FIG. 37 is another schematic diagram of a system 3700 including an apparatus 3710 generating antimicrobial gas or vapor external to a sealed environment 3750 for disinfecting items therein. System 3700 may include a gas or vapor generator apparatus 3710 coupled to a heating ventilation and air conditioning ("HVAC") system or a humidifier system to pass humidified disinfecting gas or vapor (e.g., $ClO_2$ gas or vapor) from a concentrated chlorine dioxide solution 3702, and the humidified disinfecting gas or vapor 3730 (e.g., $ClO_2$ gas or vapor) may be further evaporated through a heater 3720 that may be recirculated within the sealed environment for disinfecting items therein.

System 3700 may additionally include a pump 3704 for pumping $ClO_2$ solution 3702 to generator apparatus 3710. A water line 3706 may provide water to generator apparatus 3710. A generator controller 3708 may act to control, permit user input into, or both, generator apparatus 3710. A $ClO_2$ sensor 3734 may be oriented within sealed environment 3750 and may be in communication with (wired or wireless) a process controller 3736. Process controller 3736 may ultimately control all antimicrobial gas or vapor generation of system 3700, including receiving data from sensor 3734 regarding the concentration of disinfecting gas or vapor within sealed environment 3750. Process controller 3736 may cause the generation of more or less disinfecting gas or vapor 3730 to achieve a desired antimicrobial gas or vapor concentration, based upon data received from sensor 3734.

The items for disinfection may include one or more of: healthcare personal protective equipment ("PPE"), medical equipment, apparel, garments, shoes, personal electronic devices, furniture, office supplies, built-in structures, drapes, fabrics, utensils, fixtures, decorative items, plants, and packaged or unpackaged food.

Sealed environment 3750 may be any of: a sealable bag, a tent, a container, a drum, a tumbler drum, a chamber, a room, an office, a store, a warehouse, a home, a floor of a multi-level building, a cabin, an aircraft cabin, a vehicle cabin, a surface vessel cabin, an underwater vessel cabin. Disinfecting the items contained in sealed environment 3750 may achieve destruction of one or more of: microbial organisms, bacteria, viruses, fungi, pests, toxins, germs, mites, bed bugs, and the like.

FIGS. 38A and 38B illustrate a system 3800 for generating antimicrobial gas or vapor within a sealed environment for disinfecting items in the sealed environment. System 3800 may include apparatuses 3810 and 3860 for generating antimicrobial vapor within a sealed environment for disinfecting items in the sealed environment (3820, 3830, 3840, 3850).

In FIG. 38A, system 3800 includes an apparatus 3810 (e.g., shop vacuum) used to evacuate 3812 (via a suction side 3813) a sealed environment 3820 (e.g., large bag) through a single passage 3822. After the evacuation, sealed environment 3820 may be back filled 3814 (via an exhaust side 3815) with antimicrobial gas or vapor through single passage 3822 for disinfecting items 3824 therein.

In FIG. 38B, apparatus 3860 may be used to evacuate (via a suction side 3813) and a plurality of sealed environments 3830, 3840, 3850, and backfill (via an exhaust side 3815) the plurality of sealed environments 3830, 3840, 3850 with antimicrobial gas or vapor through respective passages 3832, 3842, 3852 for disinfecting items therein. Alternatively, as illustrated in FIG. 38B, apparatus 3860 may be used as a gas or vapor generator within a sealed environment 3870. Sealed environment 3870 may be anyone of: a sealable bag, a tent, a container, a drum, a tumbler drum, a chamber, a room, an office, a store, a warehouse, a home, a floor of a multi-level building, a cabin, an aircraft cabin, a vehicle cabin, a surface vessel cabin, an underwater vessel cabin.

FIG. 40 illustrates a method 4000 for generating antimicrobial gas or vapor within a sealed environment or external to the sealed environment to disinfect items within the sealed environment. Method 4000 includes: providing an antimicrobial vapor to an enclosed environment (step 4002); generating the antimicrobial vapor within the enclosed environment through one of: (step 4004) (a) pumping a controlled concentration level of liquid chlorine dioxide solution into a humidifier system to produce a stream of chlorine dioxide antimicrobial vapor, (b) directly pumping a controlled concentration level of chlorine dioxide antimicrobial vapor to an ambient of the enclosed environment, (c) generating ambient chlorine dioxide antimicrobial vapor by dissolving solid chlorine dioxide reagent into a container filled with water; and placing the container that releases the ambient chlorine dioxide antimicrobial vapor into the enclosed environment, (step 4006); generating the antimicrobial vapor external to the enclosed environment through one of: (step 4008) (a) pumping a controlled concentration level of liquid chlorine dioxide solution into a humidifier system to produce a stream of chlorine dioxide antimicrobial vapor, (b) directly pumping a controlled concentration level of liquid chlorine dioxide antimicrobial vapor to ingress the enclosed environment through a single passage of the enclosed environment, and (c) directly pumping a controlled concentration level of chlorine dioxide antimicrobial vapor to ingress the enclosed environment through a first passage of the enclosed environment (step 4010).

As illustrated, method 4000 optionally performs step 4002 followed by steps 4004 and 4006, or performs step 4002 followed by steps 4008 and 4010.

Figure 42:
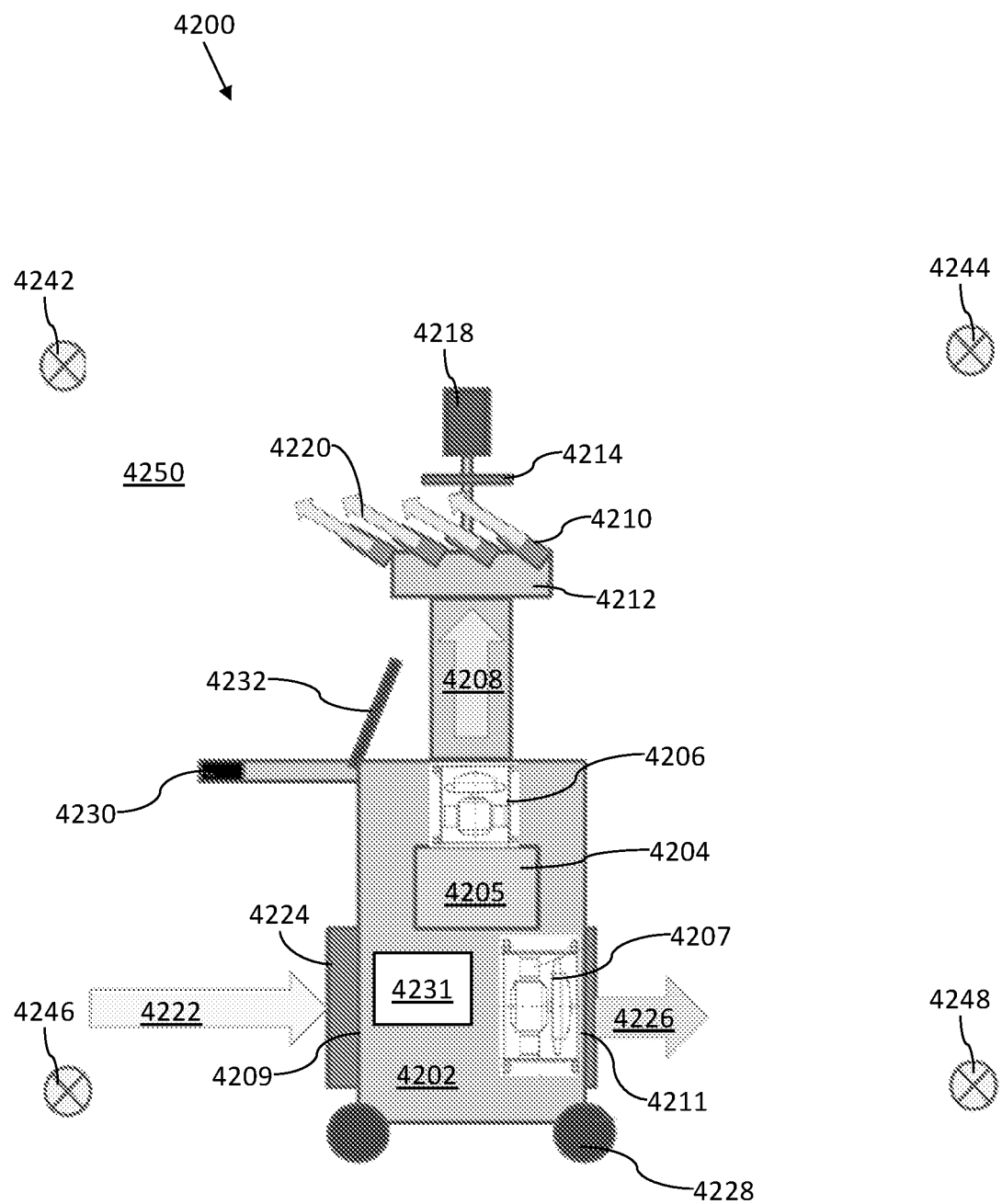
FIG. 42 illustrates an example of an apparatus 4200 that generates antimicrobial gas or vapor for disinfecting items in three-dimensional space.
Figure 43:
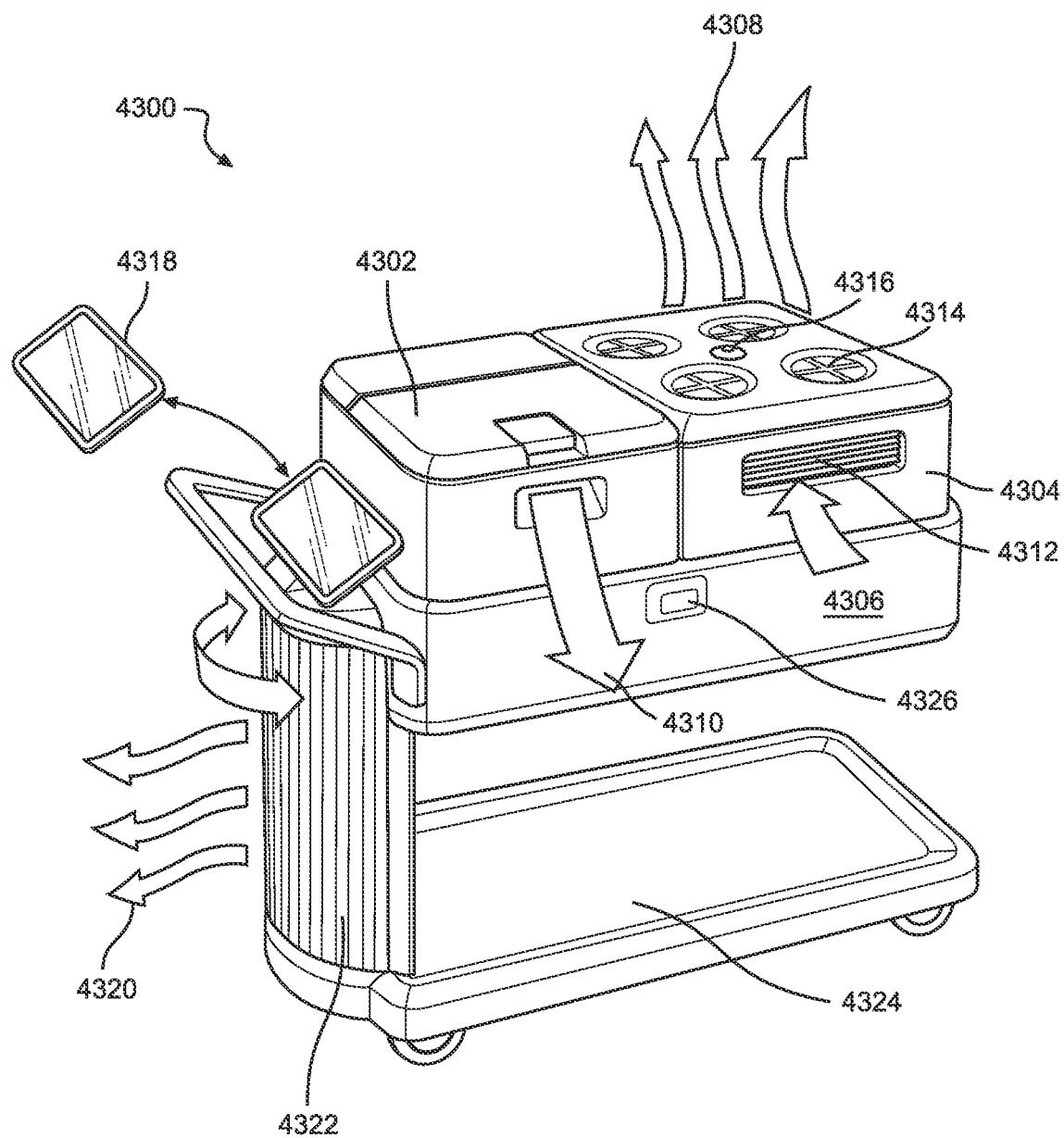
FIG. 43 illustrates an example of an apparatus 4300 that generates antimicrobial gas or vapor for disinfecting items in three-dimensional space.
Figure 44:
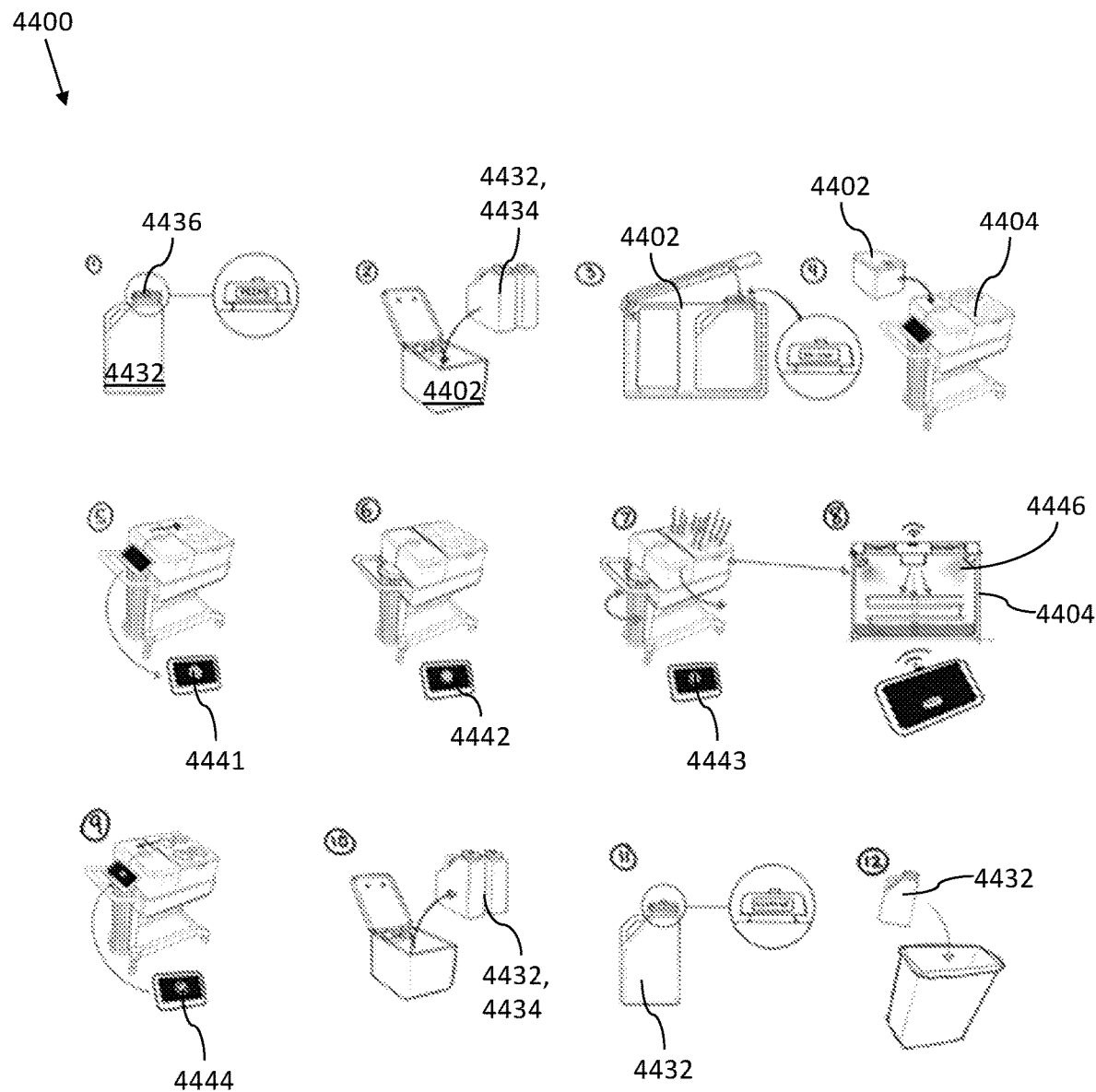
FIG. 44 illustrates an example procedure 4400 for the use of apparatus 4300 in FIG. 43 to generate antimicrobial gas.
Figure 47:
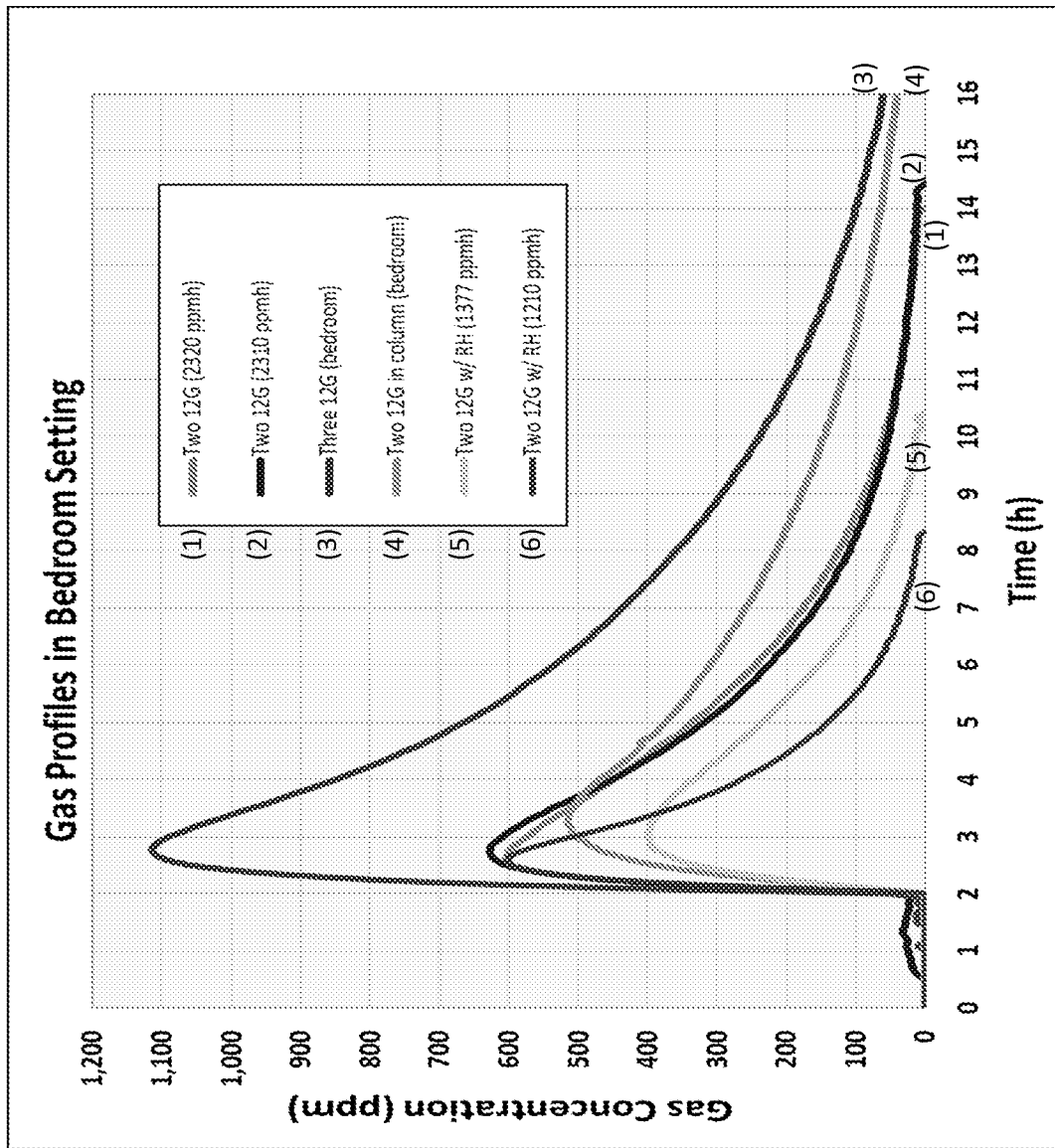
FIG. 47 illustrates gas concentration profiles in room setting with furniture.
Figure 48:
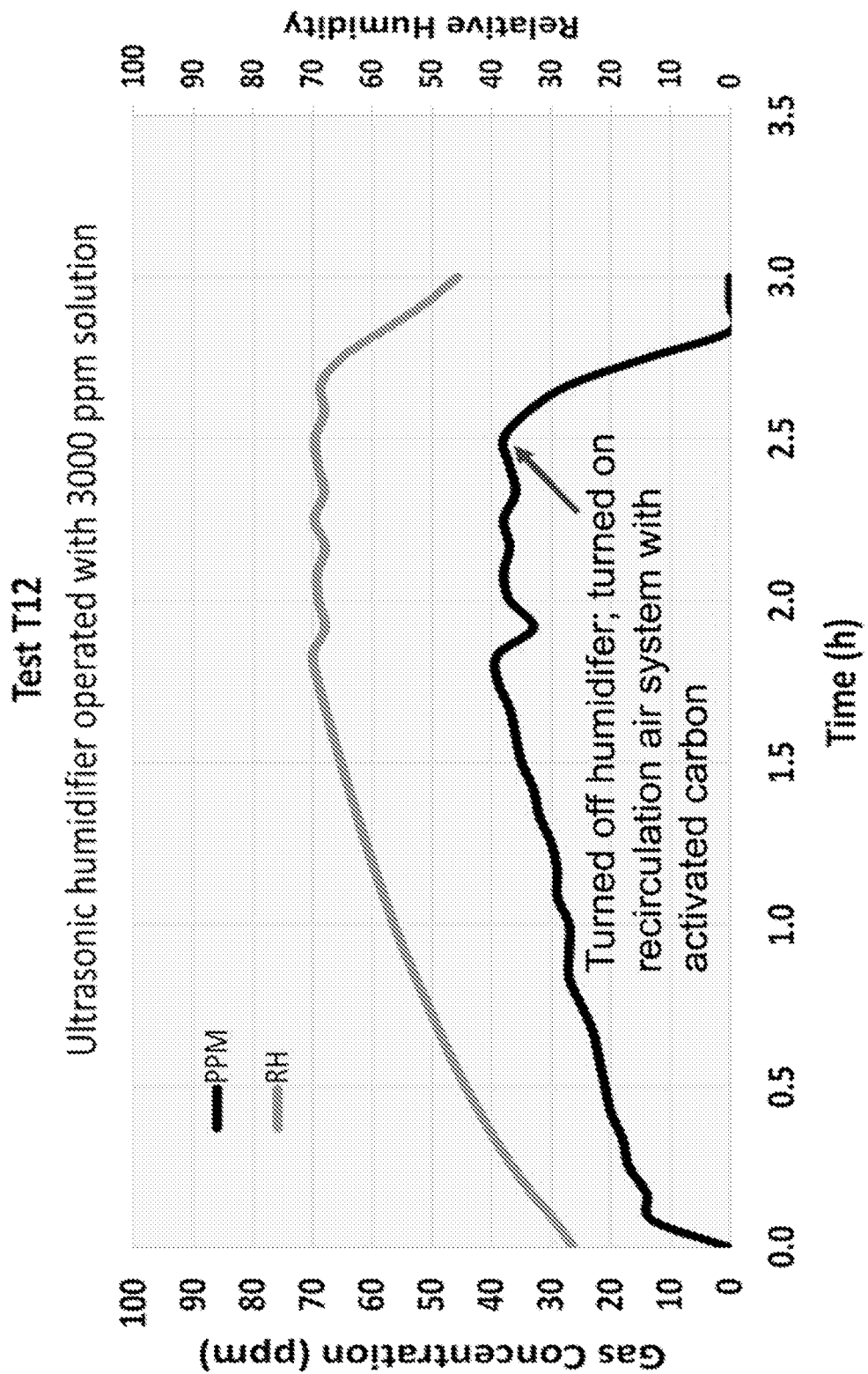
FIG. 48 illustrates relative humidity and generated $ClO_2$ gas concentration from a $ClO_2$ solution.
Figure 49:
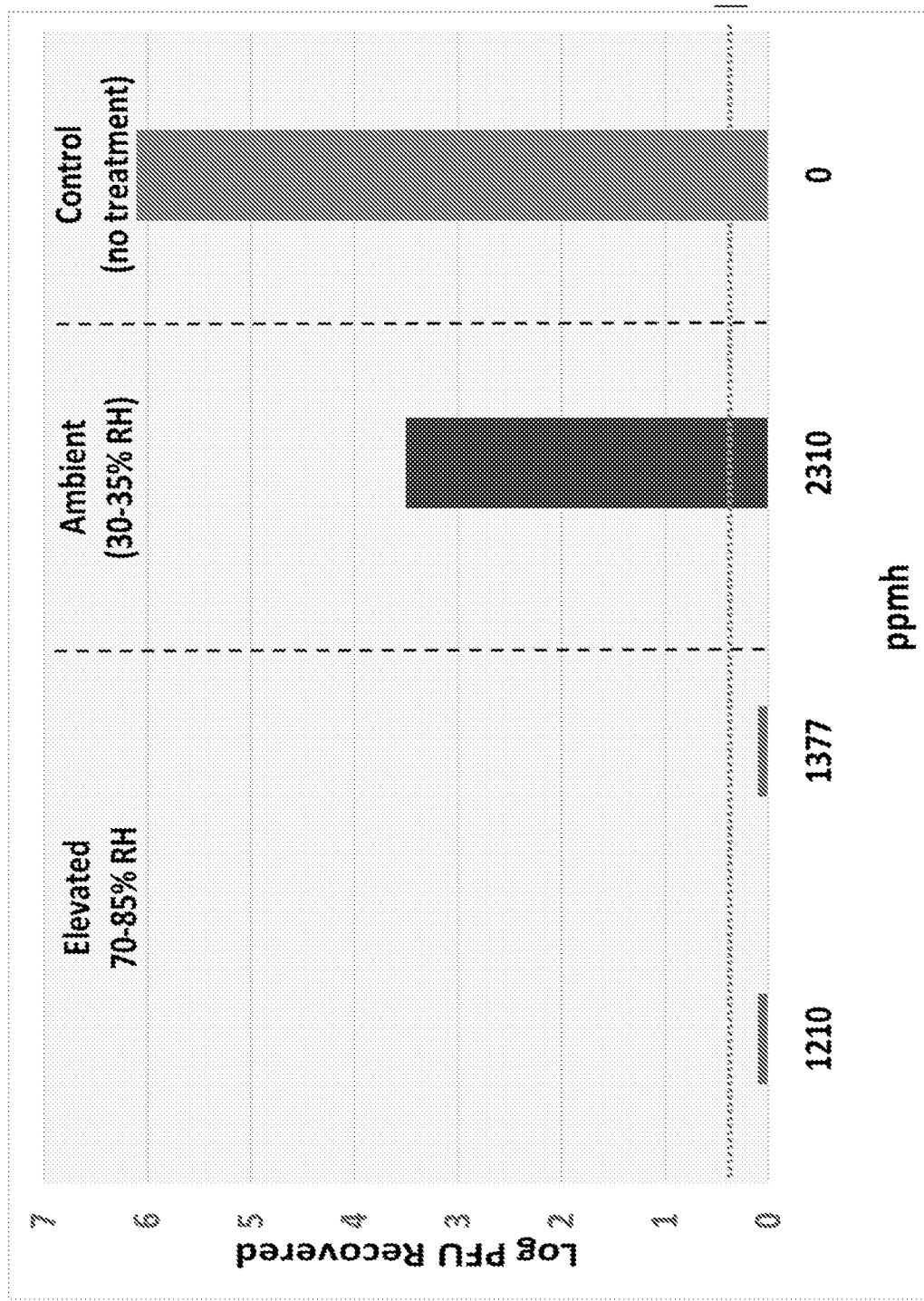
FIG. 49 illustrates a correlation of increase in disinfection efficacy with elevated humidity.
Figure 50:
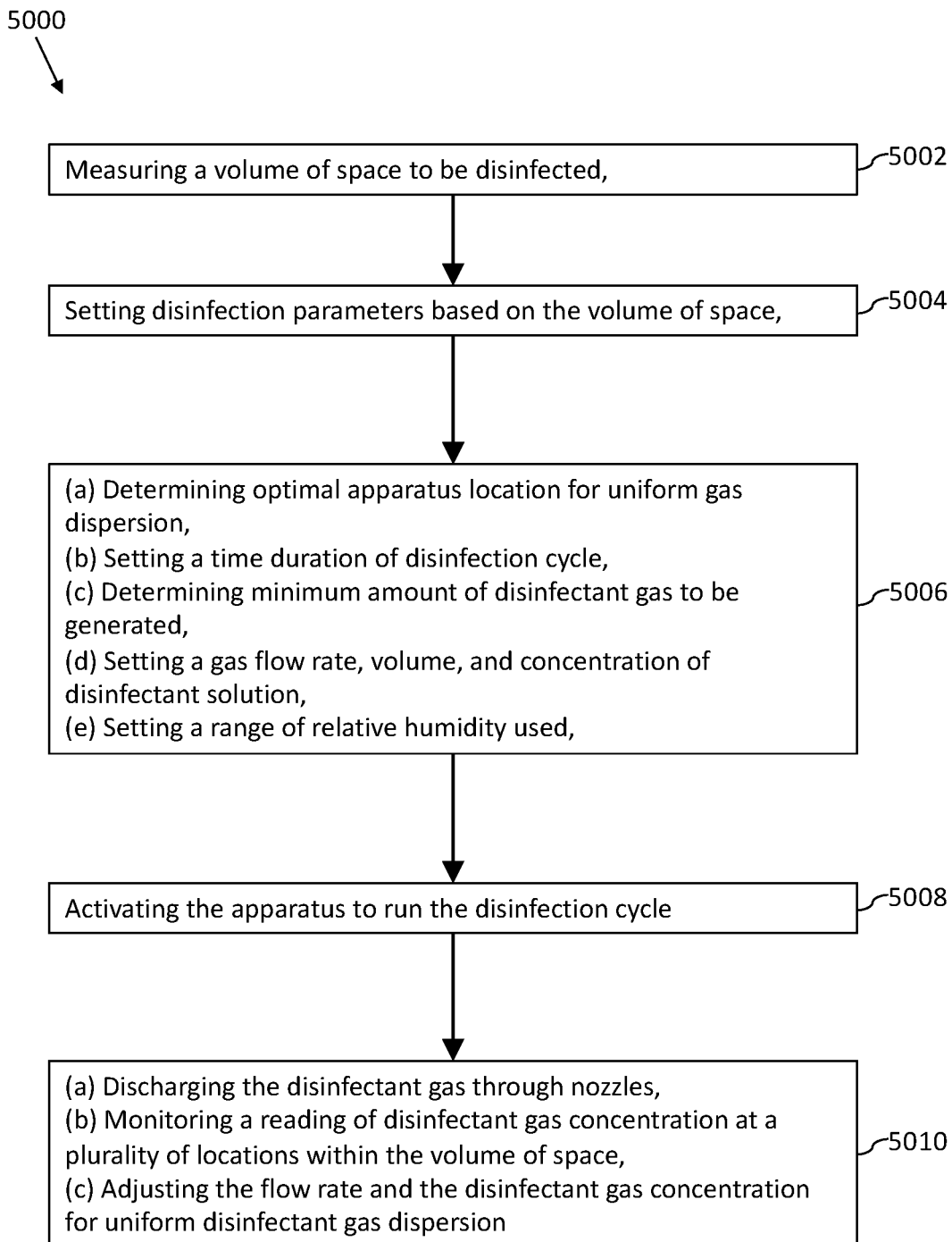
FIG. 50 illustrates a method for generating an antimicrobial gas and dispersing the gas via an apparatus.

FIG. 42 illustrates an apparatus 4200 that generates antimicrobial gas or vapor for disinfecting items in three-dimensional space. FIG. 43 illustrates an apparatus 4300 that generates antimicrobial gas or vapor for disinfecting items in three-dimensional space. FIG. 44 illustrates a procedure 4400 for the use of apparatus 4300 in FIG. 43 to generate antimicrobial gas. FIG. 45 illustrates a table showing temperature effects to solubility of $ClO_2$ gas in water and in air and required amount of $ClO_2$ gas for a defined room size. FIG. 46 illustrates a uniformity of $ClO_2$ gas concentration distributed within a room. FIG. 47 illustrates gas concentration profiles in room setting with furniture. FIG. 48 illustrates relative humidity and generated $ClO_2$ gas concentration from a $ClO_2$ solution. FIG. 49 illustrates a correlation of increase in disinfection efficacy with elevated humidity. FIG. 50 illustrates a method 5000 for generating an antimicrobial gas and dispersing the gas via an apparatus.

FIGS. 42 and 50 illustrate an example of a mobile apparatus 4200 performing a computer implemented method 5000 to generate and disperse an antimicrobial gas 4220 to a defined volume of space. Method 5000 includes performing the following steps: measuring a volume of space to be disinfected (step 5002); setting by a controller 4231, disinfection parameters based on the measured volume of space 4250 to be disinfected (step 5004), wherein the disinfection parameters comprising at least the following: (a) determining an optimal location of the apparatus 4200 in the volume of space for uniform dispersion of the antimicrobial gas 4220, (b) a time duration of disinfection cycle, (c) a minimum amount of antimicrobial gas required to be generated, (d) a flow rate of antimicrobial gas generation, a volume of antimicrobial solution, and a concentration of antimicrobial solution 4205 to meet the required flow rate of antimicrobial gas 4220, (e) a range of antimicrobial gas relative humidity to be used during a disinfection cycle (step 5006). Afterwards, activating the apparatus 4200 to run the disinfection cycle until completion; discharging through a plurality of nozzles 4210 which are mounted on an oscillating head 4212, the antimicrobial gas 4220 to volume of space 4250.

Method 5000 may further include: monitoring periodically, a reading of antimicrobial gas concentration at a plurality of remote locations (by a plurality of remote sensors 4242-4248) within volume of space 4250 during the disinfection cycle and adjusting one or more of: the antimicrobial gas flow rate and the antimicrobial gas concentration for uniform antimicrobial gas dispersion in volume of space 4250 (step 5010).

Measuring of the volume of space may be performed by an integrated on-board laser beam scanner 4214. The method may include oscillating along an axis, the plurality of nozzles 4210 mounted on the oscillating head 4212 in a full circle or less than a half circle. The method may include: in response to the monitored reading of the antimicrobial gas concentration at each of the plurality of locations 4242-4248, configuring one or more respective nozzles 4210 mounted on the oscillating head 4212 to perform one or a combination of the following to offset concentration differences of the antimicrobial gas at the plurality of locations: adjusting a vertical angle of the nozzle, adjusting a discharge flow rate of the antimicrobial gas, and adjusting a discharge pressure of the antimicrobial.

In response to the monitored reading of the antimicrobial gas concentration at each of the plurality of locations 4242-4248, the method may include varying a fan speed of a first blower 4206 which sucks the antimicrobial gas 4208 released from an antimicrobial solution contained in a reactor 4204. The antimicrobial gas may be released from the antimicrobial solution in vapor phase at the range of relative humidity (RH) according the setting of the controller 4231, wherein the range of relative humidity of the vapor phase is correlated to a temperature of the antimicrobial solution 4205.

The antimicrobial gas or vapor 4220 may be one of: chlorine dioxide ($ClO_2$) gas or vapor and hydrogen peroxide ($H_2O_2$) gas or vapor. The $ClO_2$ gas or vapor may be generated by chemically reacting a chlorite containing compound with an activator and the $H_2O_2$ gas or vapor is generated by chemically reacting a urea hydrogen peroxide, borax, perborate, or percarbonate compound with the activator, wherein the activator includes an acid or a proton donating solvent. The chlorite or peroxide containing compound and the activator are separately packaged as anhydrous powder or separately packaged as concentrated solution packages which are to be mixed together in the reactor 4206 to form the antimicrobial solution 4205.

Upon completion of the disinfection cycle, an aeration cycle may be started for a defined duration of time to adsorb ambient antimicrobial gas in the volume of space. Alternately, the aeration may also take place during the antimicrobial dispersing cycle to facilitate homogeneity of the antimicrobial gas 4220 in ambient. More specifically, the aeration cycle may be performed by drawing and recirculating by a second blower 4207, ambient air through a carbon/HEPA filter 4224 disposed at an inlet 4209 of the apparatus, and venting filtered air at an outlet 4211 of the apparatus, wherein the second blower 4207 is physically disposed below and away from the first blower, such that the antimicrobial gas or vapor in the ambient is adsorbed by the carbon/HEPA filter 4224.

The mobile apparatus 4200 may be mounted on wheels 4228 to provide mobility. The method may include sending a warning signal from the mobile apparatus in a situation including one or a combination of: (1) when the antimicrobial gas or vapor 4250 in the ambient air exceeds a defined unsafe level, (2) malfunctioning of either the first blower 4206 or the second blower 4207, or (3) depletion of antimicrobial solution 4205 in the reactor 4206. The warning signal may be visual, audible, transmitted wirelessly to a remote device (e.g., phone), or any combination thereof.

FIGS. 43 and 44 illustrate an example of a mobile apparatus 4300 performing a computer implemented method 4400 to generate and disperse an antimicrobial gas or vapor 4310 for disinfecting items in three-dimensional space. Apparatus 4300 may include a humidifier unit 4302, a main unit 4304, a support element 4306, a filtered air outlet 4308, a carbon filter intake 4312, main unit fans 4314, a gas sensor 4316, a removable remote and data readout tablet 4318, an oscillating tower fan 4322 with fan outlet 4320, under cart storage and portable battery placement area 4324, and a cycle indicator light 4326. Apparatus 4300 may be mobile and placed upon wheels for easy transport into and from a three-dimensional space to be disinfected.

Method 4400 may include turning a cap 4436 of a concentrated solution bottle 4432, 4434 to "prime" and let sit for at 2 hours; place bottles 4432, 4434 into container unit 4402 (of humidifier unit 4302); turn caps 4436 of bottles 4432, 4434 to "in use" and close lid down to lock bottles 4432, 4434 into the system's pump; place container unit 4402 into mobile apparatus 4300 adjacent to main unit 4404; remove remote 4318 from apparatus 4300 and leave the room to be treated, and when yellow light 4441 illuminates, apparatus 4300 will begin pumping fluid into main unit 4404; when green light 4442 illuminates, apparatus 4300 is ready to begin disinfection; when blue light 4443 illuminates, apparatus 4300 has begun its cycle and humidifier 4302 and fans 4314, 4322 are activated; when the disinfection cycle is complete, a deactivation command will appear, and UV lights 4446 and chemical release will cause the system to deactivate; when red light 4444 illuminates, apparatus 4300's cycle is complete, it is safe for the user to return to the disinfected room, and the fluid has been pumped out of main unit 4304, 4404 and into the original bottles 4432, 4434; container unit 4402 will unlock upon replacement of remote 4318 back upon apparatus 4300, bottles 4432, 4434 may be inspected and caps 4436 may be set to "dispose" and discarded.

In another aspect, the process of generating antimicrobial gas may include the following steps:
1. Steps in Process
   a. User inputs room identifying information (or automated via RFID tag) and selects disinfection routine via touch screen, Bluetooth or WIFI communication.

i. Disinfection cycle may vary based on need, e.g., short-cycle sanitization, between patient turnover, known contagion in room, deodorizing, and the like.
ii. Laser scanner to calculate room dimensions/volume, or user-selected options to determine size of a room which may include a combination of user input, laser scanning, and in response to gas concentration levels measured by the system sensors.
iii. Disinfection cycle parameters (e.g., RH, ramp up, concentration, time, aeration) based on data models for targeted level of disinfection and room size.
  1. Actual data will be recorded for each cycle for each room and used to refine models, in general and for specific rooms/spaces.
iv. User provided feedback giving estimated time to run disinfection cycle.
v. Warning light activated indicating cycle about to start (occupants should leave the room).
b. Device executes user selected disinfection routine based on data model.
  i. Warning light changes color indicating cycle has started; user is notified via remote monitoring app.
  ii. Conditions the room to target RH value (based on remote sensor feedback).
  iii. Calculates rate of antimicrobial gas generation needed to reach target concentration (ppm) during pre-determined time window for initial ramp up.
  iv. Generates and dispenses antimicrobial gas at calculated rate.
  v. Uses forced air flow and directional and/or rotating nozzles to dispense gas into room volume.
  vi. CFM is in excess of gas generation uptake rate and enough to uniformly mix gas in room volume.
  vii. Intake air for gas antimicrobial mixing is HEPA filtered.
  viii. Adjusts rate of antimicrobial gas generation to hit targeted rate during ramp up based on feedback from remote chemical sensors to adjust gas generation.
    1. Required rate of antimicrobial gas generation is impacted by amount of equipment, furniture, etc. in the room (taking up calculated volume space), the uptake of antimicrobial gas by porous items in the room, and the natural decay of antimicrobial gas concentration.
  ix. Automatically adjusts rate of antimicrobial gas generation based on feedback from remote chemical sensors to maintain target concentration for duration of disinfection cycle.
  x. Updates user on time to end of cycle once steady-state conditions are met.
  xi Continuously monitors and records sensor data, creating a record that disinfection process parameters were maintain throughout cycle.
  xii. Terminates gas generation at end of program cycle.
  xiii. Aeration cycle is initiated.
    1. Lower blower system turns over room in air until chemical antimicrobial is no longer detectable (plus factor of safety).
    2. Intake air is filtered through carbon filter and HEPA filter to remove antimicrobial and contaminants from air.
  xiv. Warning light changes color indicating cycle has ended; user is notified via remote monitoring app that it is safe to enter the room.
c. Reporting and data analytics.
  i. Report file generated and uploaded to central data collection system for documentation purposes.
  ii. Process data added to model training data set to continuously refine disinfection models, both generally and for that specific room.
2. Chlorine Dioxide Gas
a. Pure chlorine dioxide gas can be generated from any number of source materials; preferably, generation materials produce a high level of chlorine dioxide.
b. Method of generating $ClO_2$ needs to be capable of enough $ClO_2$ for at least one antimicrobial cycle.
c. Method of generating $ClO_2$ needs to be capable of producing $ClO_2$ fast enough to reach target room concentration levels within about 15 minutes.
d. Method of $ClO_2$ generation may be batch process generation or just-in-time production.
e. Generation materials are preferably provided in a form that does not require human contact, here introduction/integration process with equipment support chemical feed, and feed rate can be controlled to control the rate of $ClO_2$ production.
f. Pure $ClO_2$ gas can be separated from liquid using any method, e.g., stirring/mixing; aeration; surface fans/blower; water tower with countercurrent air; airflow over/through water flow or spray; thin film evaporation; vacuum; piezoelectric; heating; and the like.
g. Liquid byproducts from $ClO_2$ generation process may be neutralized by any number of chemical reaction processes to destroy residual $ClO_2$. Alternatively, generation liquids can be recirculated through the system during the aeration cycle to remove residual $ClO_2$.
3. Configuration
a. The $ClO_2$ gas disinfection system can be configured as a fully automated unit, with full process control and documentation features, as described.
b. Manual configurations without process automation and control may be configured for use by properly trained personnel.

Example 1

Figure 51A:
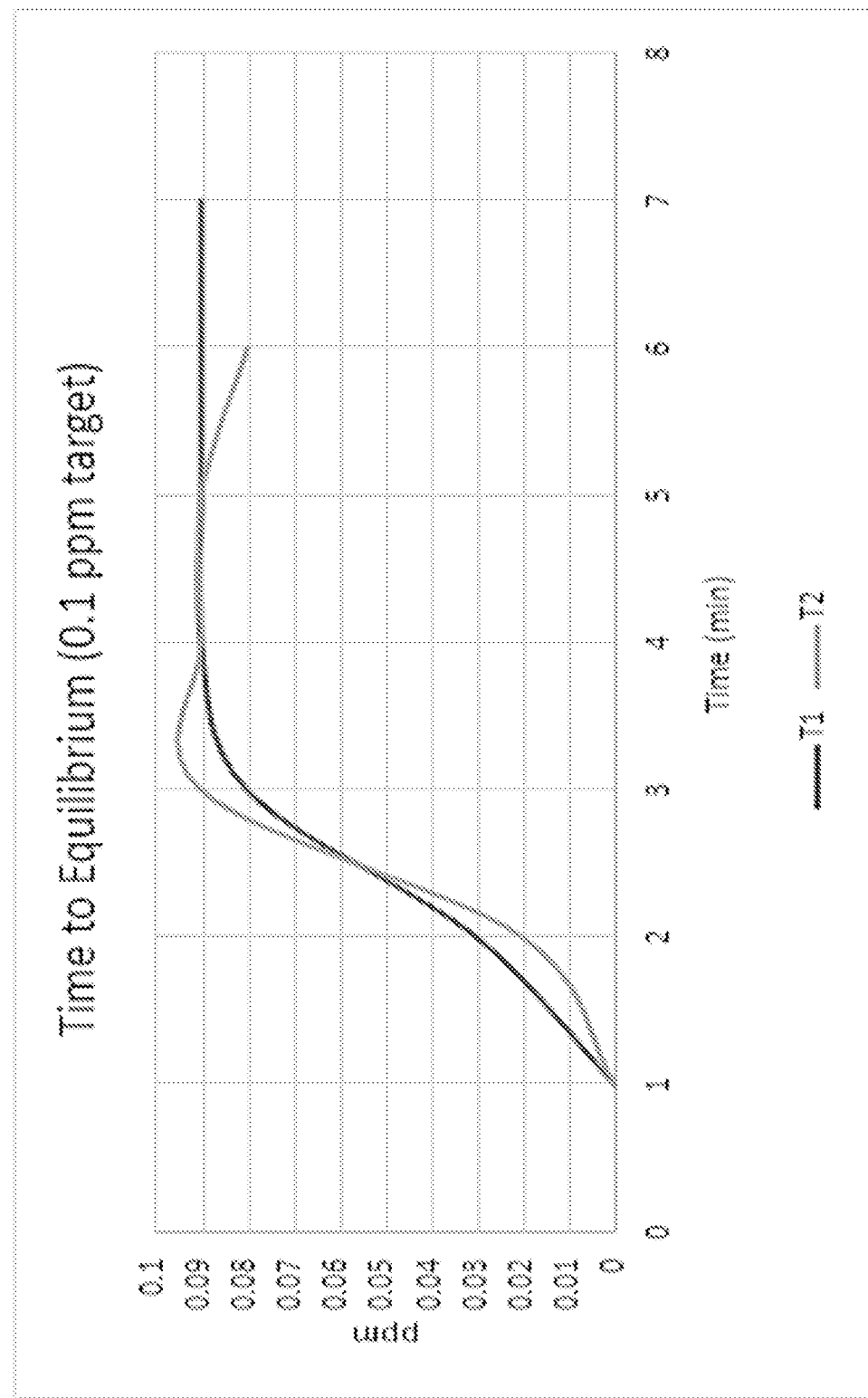
FIG. 51A illustrates the time (minutes) to equilibrium for a target concentration of 0.1 ppm of $ClO_2$ to air.

FIG. 51A illustrates the time (minutes) to equilibrium for a target concentration of 0.1 ppm of $ClO_2$ to air. As illustrated, equilibrium was reached in a matter of minutes using this very small setup.

Figure 51B:
FIG. 51B illustrates the concentration (ppm of $ClO_2$ to air) measured at five ports over time (minutes).

After the ambient air inside the ISO shipping container reached an equilibrium of 0.08 ppm, the syringe pumps were turned on to a rate of 1 µL/min. and the $ClO_2$ concentration was measured at five different ports in the ISO shipping container walls, the ports being spread at different locations around the ISO shipping container. FIG. 51B illustrates the concentration (ppm of $ClO_2$ to air) measured at each of the five ports over time (minutes). The concentration measured at each port was substantially similar over the test time, as illustrated in FIG. 51B.

Example 2

Figure 52A:
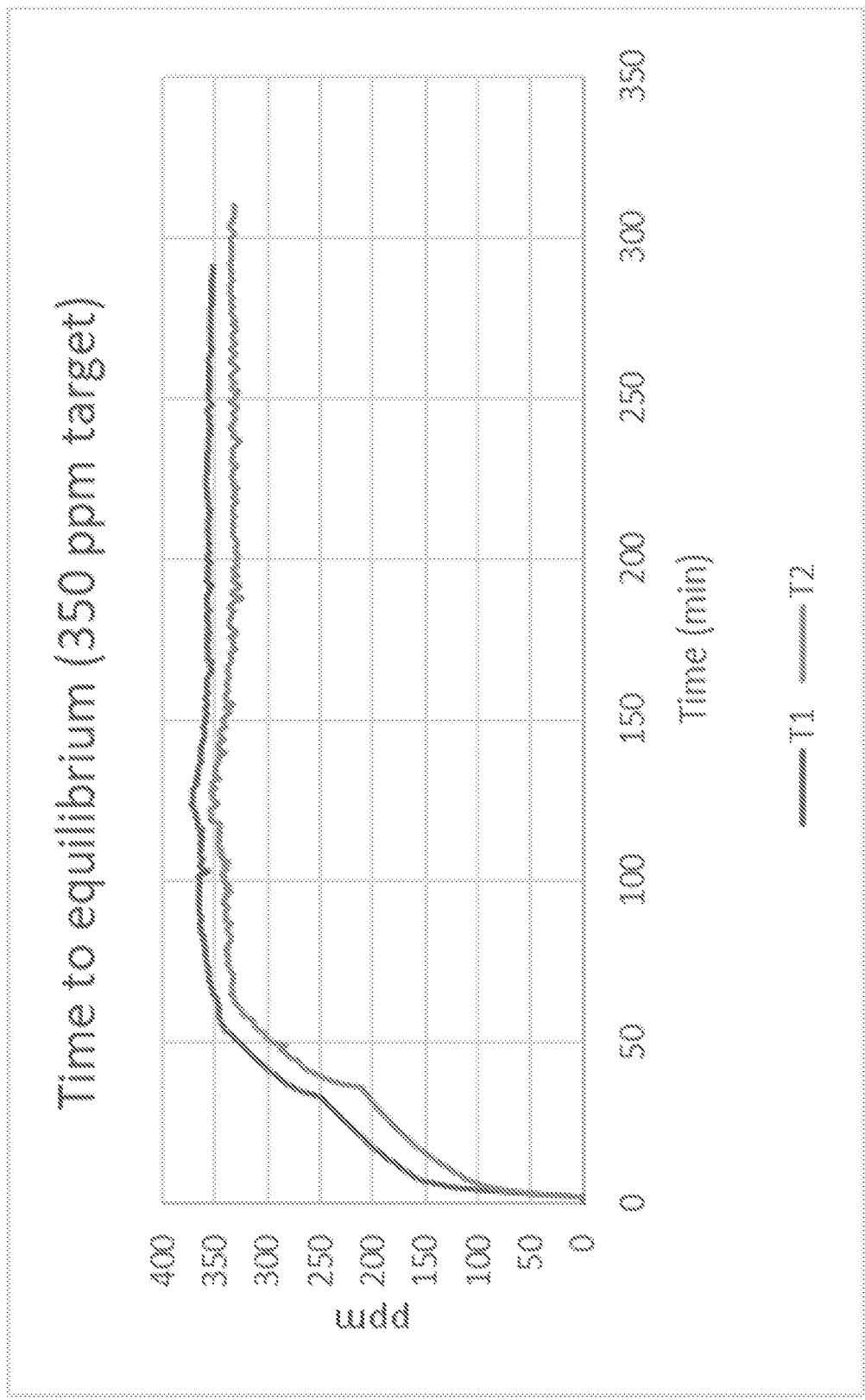
FIG. 52A illustrates the time (minutes) to equilibrium for a target concentration of 350 ppm of $ClO_2$ to air.

In Example 2, a dose of 125 mL of 0.75 g/mL $NaClO_2$ and 632 mL of 0.50 g/mL $Na_2S_2O_8$ were dispensed into a unit with fans blowing down onto the $ClO_2$ solution. The unit was located in the center of an ISO shipping container (e.g., sealed environment). The fans blew the air within the enclosed, and sealed, ISO shipping container, which had an internal volume of 1,300 cubic feet/36.8 cubic meters. FIG. 52A illustrates the time (minutes) to equilibrium for a target concentration of 350 ppm of $ClO_2$ to air. As illustrated, equilibrium was reached in about 60 minutes.

Figure 52B:
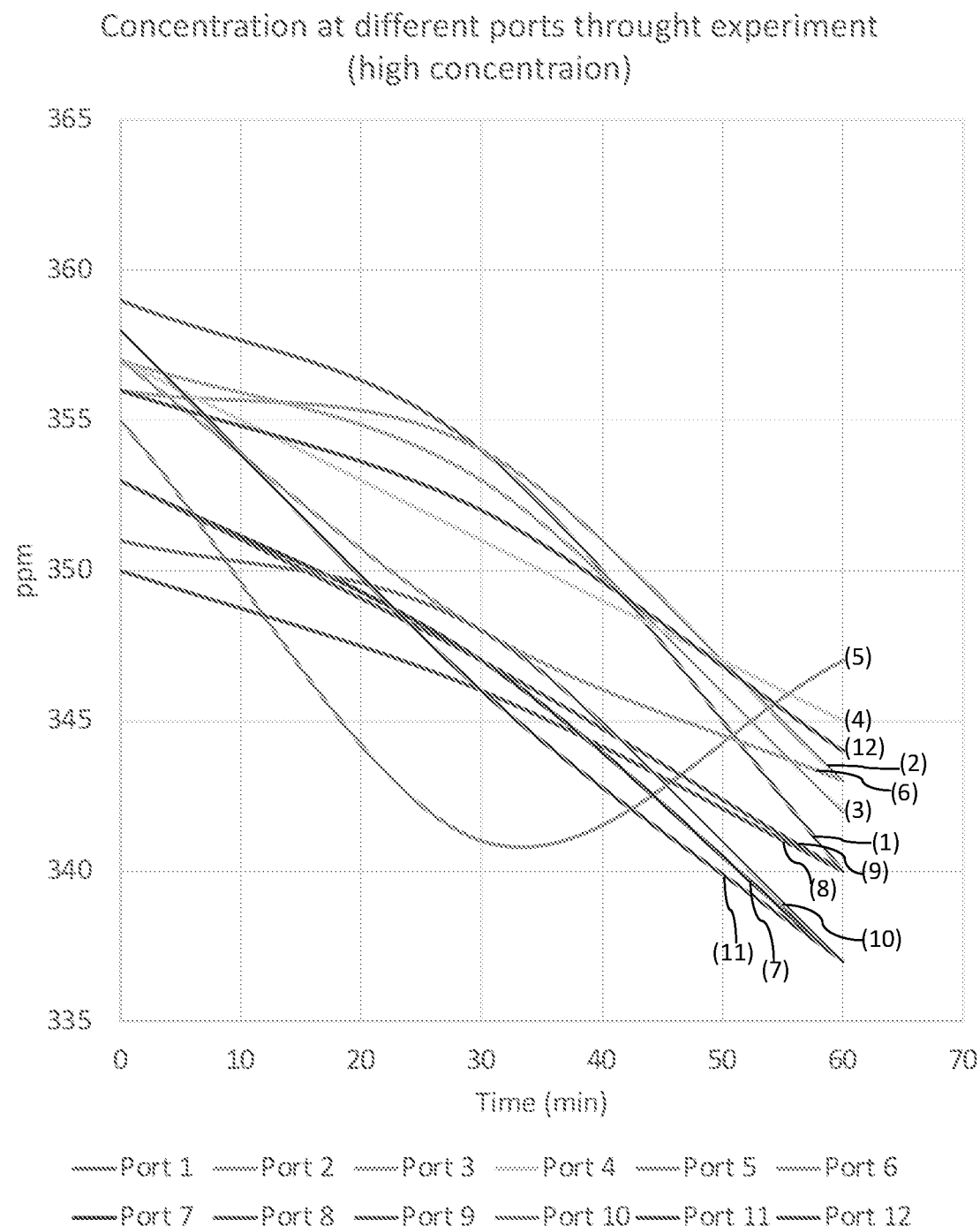
FIG. 52B illustrates the concentration (ppm of $ClO_2$ to air) measured at 12 ports over time times).

After the ambient air inside the ISO shipping container reached a concentration of about 350 ppm, $ClO_2$ production was ceased, and a PortaSens device was used to read the concentration at 12 different ports in the ISO shipping container walls, the ports being spread at different locations around the ISO shipping container. FIG. 52B illustrates the concentration (ppm of $ClO_2$ to air) measured at each of the 12 ports over time (minutes). The concentration measured at each port was substantially similar over the test time, as illustrated in FIG. 52B.

Example 3

Figure 53A:
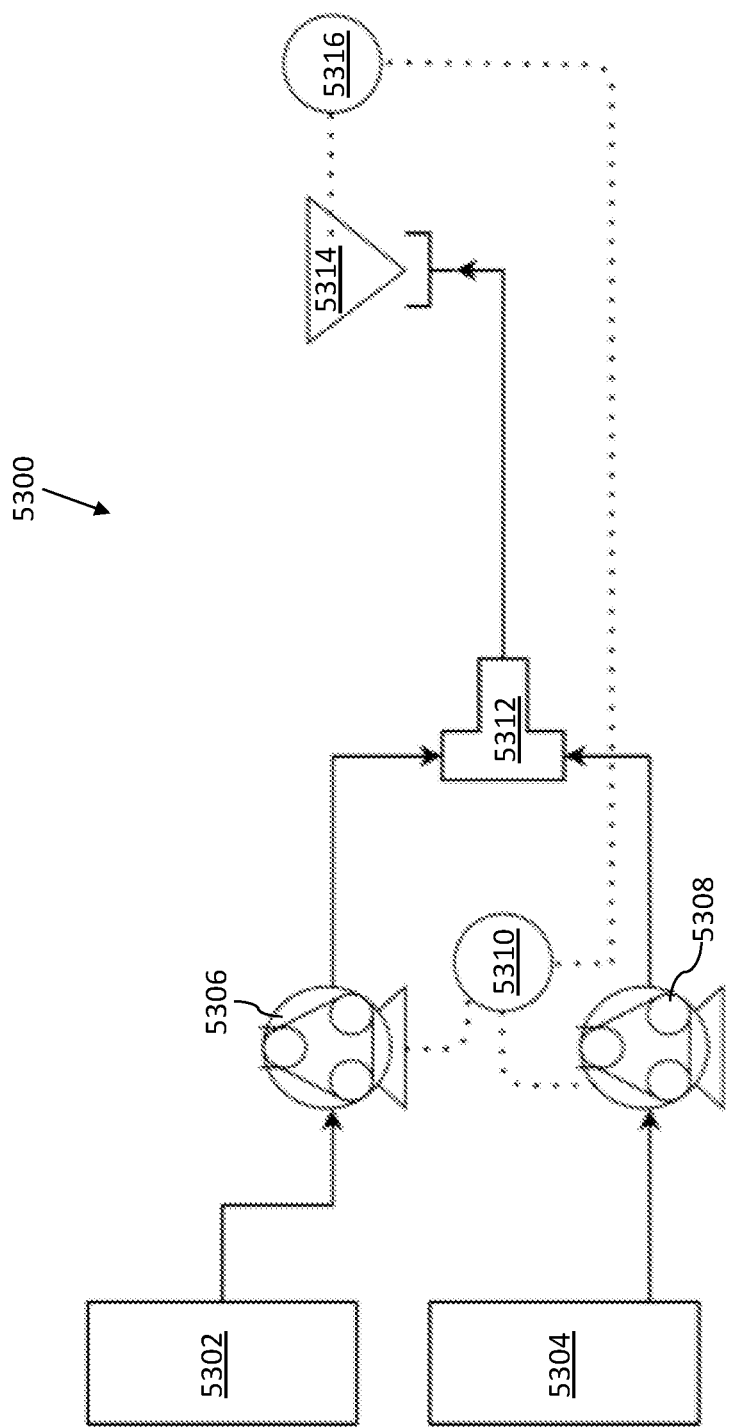
FIG. 53A illustrates a diagram of an example system 5300 for generating $ClO_2$ vapor from small volumes of high concentration liquid precursors.
Figure 53B:
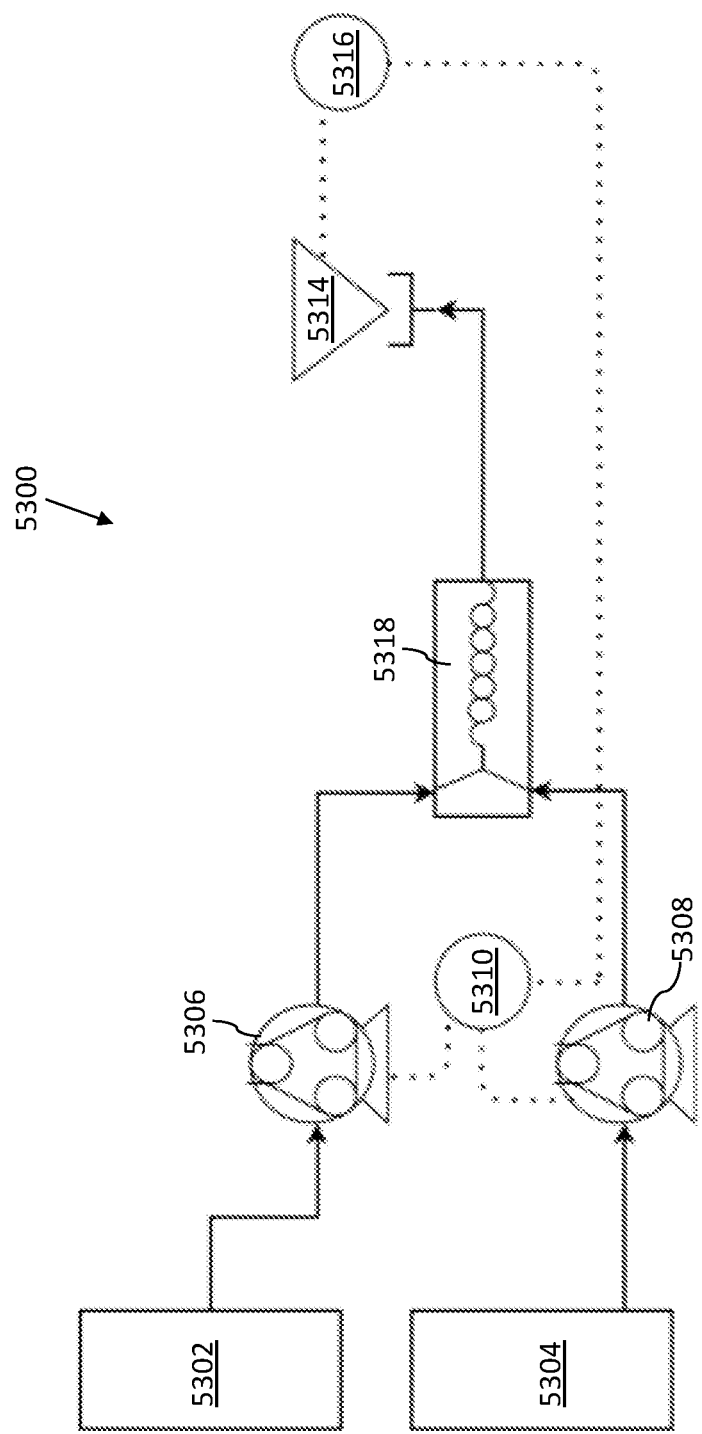
FIG. 53B illustrates a diagram of example system 5300 for generating $ClO_2$ vapor from small volumes of high concentration liquid precursors.

FIGS. 53A and 53B illustrate diagrams of an example system 5300 for generating $ClO_2$ vapor from small volumes of high concentration liquid precursors. System 5300 includes a sodium chlorite concentrate 5302 and an activator concentrate 5304. Sodium chlorite concentrate 5302 is fluidically connected to a pump 5306, while activator concentrate 5304 is fluidically connected to a pump 5308. A controller 5310 is operatively connected to both of pumps 5306 and 5308. Controller 5310 controls the operation of pumps 5306 and 5308, including at least volume of fluid pumped, flow rate, timing of pump activation, and the like.

As illustrated in FIG. 53A, each of pumps 5306 and 5308 are fluidically connected to a t-mixing chamber 5312, where sodium chlorite concentrate 5302 and activator concentrate 5304 are combined to generate $ClO_2$ vapor. As illustrated in FIG. 53B, each of pumps 5306 and 5308 are fluidically connected to a microfluidic mixing chip 5318, where sodium chlorite concentrate 5302 and activator concentrate 5304 are combined to generate $ClO_2$ vapor.

$ClO_2$ vapor is diffused into the ambient air at diffuser 5314. A $ClO_2$ sensor 5316 senses the concentration of $ClO_2$ in the ambient air and is operatively connected to controller 5310. If the concentration of $ClO_2$ in the ambient air is lower than desired, controller 5310 causes pumps 5306 and 5308 to generate more $ClO_2$, or to generate $ClO_2$ at a greater rate, as necessary to achieve the desired concentration of $ClO_2$. If the concentration of $ClO_2$ in the ambient air is greater than desired, controller 5310 causes pumps 5306 and 5308 to generate less $ClO_2$, or to generate $ClO_2$ at a lesser rate, or to cease the generation of $ClO_2$ for a desired time to allow the concentration of $ClO_2$ to fall to a desired level, as necessary to achieve the desired concentration of $ClO_2$.

Pumps, such as pumps 5306, 5308, 308A, 308B, and 308C, may be positive displacement pumps. Positive displacement pumps may provide a benefit in that for each rotation/reciprocation of the pump, the volume of fluid pumped is known. In this arrangement, a mass flow controller or flow sensor (such as flow sensors 318A and 318B) may be eliminated from the system. Positive displacement pumps may allow a closed-loop independent sensor (e.g., an encoder) on the pump's rotation/reciprocation means, which further allows the system to yield an independent measure of the pump's movement and/or the volume of fluid pumped. When not reciprocating or rotating, the pumping action may maintain a normally-closed configuration to eliminate leakage flow, which is critical to the control of microvolumes (e.g., microliters), and may eliminate one or more secondary valves, including for example one or more of a leak control valve and a check valve.

In one aspect, the matter transport system of antimicrobial generators must be designed to minimize post-pump to generator-release "dead volume," which pertains to how much material is left between a pump and downstream active/passive fluidic and/or generator elements. In one aspect, a target may be less than 1×, or less than 0.5× of minimum generator cycle volume of precursors consumed as same dead space.

FIGS. 54A-C illustrate results of $ClO_2$ generation using system 5300 or similar systems. The results illustrated in FIGS. 54A-C correspond to generation of 0.1 ppm of $ClO_2$ vapor from small volumes of high concentration precursors. FIG. 54A illustrates results obtained from a two-component concentrated liquid generation of $ClO_2$. FIG. 54B illustrates results obtained from an electrochemical generation of $ClO_2$ from concentrated liquid $NaClO_2$. FIG. 54C illustrates projections for chemical use necessary for a 1,000 cubic foot (28.3 cubic meter) room including various activators, both for initial treatment and after 30 days of continuous operation.

Example 4

The efficacy of $ClO_2$ at ranges of approximately 0.1 ppmv and 5 ppmv was assessed against clinically-relevant infectious bacteria including *Klebsiella pneumonia* (Kp), *Pseudomonas aeruginosa* (PA), *Staphylococcus aureus* (Sa), and *Salmonella enterica* (Se), as well as bacteriophage Phi6 and MS2 (representing enveloped and non-enveloped virus, respectively). The microorganisms were prepared in phosphate buffered saline (PBS), dispensed onto replicate glass coupons (five 10 µL droplets; equivalent to 5-6 log cells or virions per coupon), placed into a room-scale test chamber conditioned with $ClO_2$ and 50-60% relative humidity (RH) and operated at ambient temperatures ranging from 18 to 21° C.

To assess efficacy, the concentration viable bacteria or infective virions recovered from $ClO_2$ treated coupons versus untreated control coupons versus time were measured. Per test, replicate coupons (duplicates or triplicates) were removed from the test chamber at various time intervals and assayed (extracted and enumerated) to determine the total quantity of organisms recovered. The results were plotted as kill curves (expressed as log organisms recovered versus time). The kill curves were then used to calculate the D-values of gas treatment, representing the time required to achieve a 90% reduction (or 1 log reduction) of viable/infective organisms at a given test condition. The area of the kill curve in which linear decay was observed was used to determine the D-value (calculated as the negative inverse of the linear decay slope).

Figure 55A:
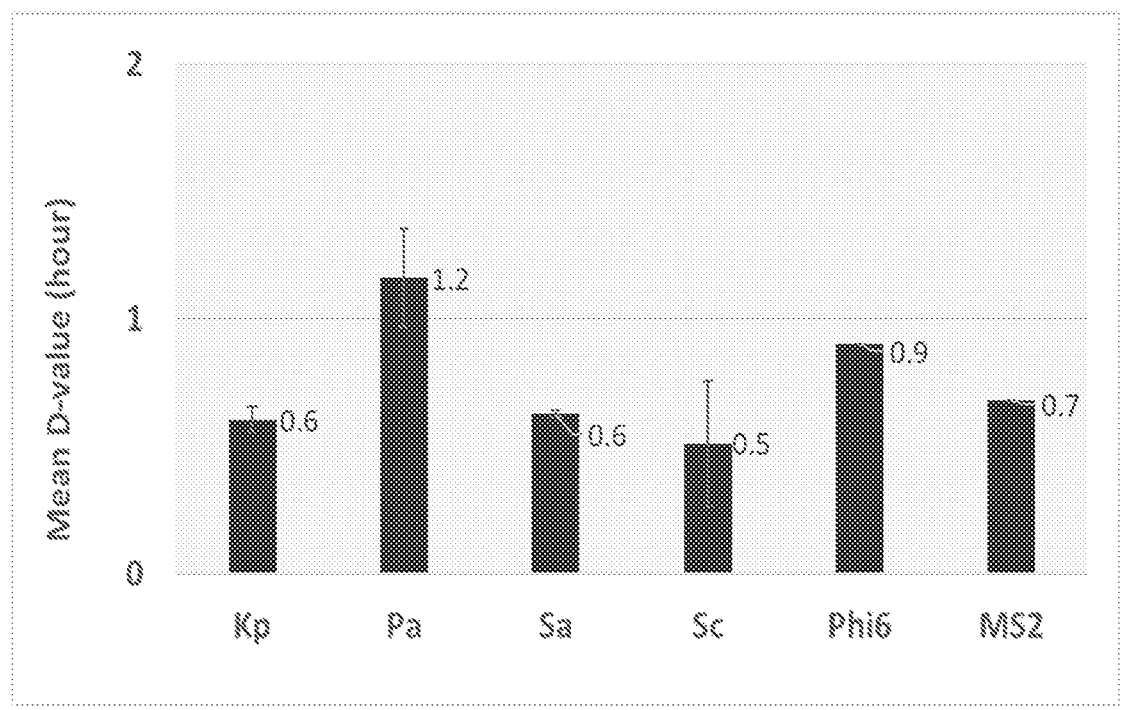
FIG. 55A illustrates the mean D-values (hours) from replicate tests per organism performed at the range of 0.11±0.04 ppmv.
Figure 55B:
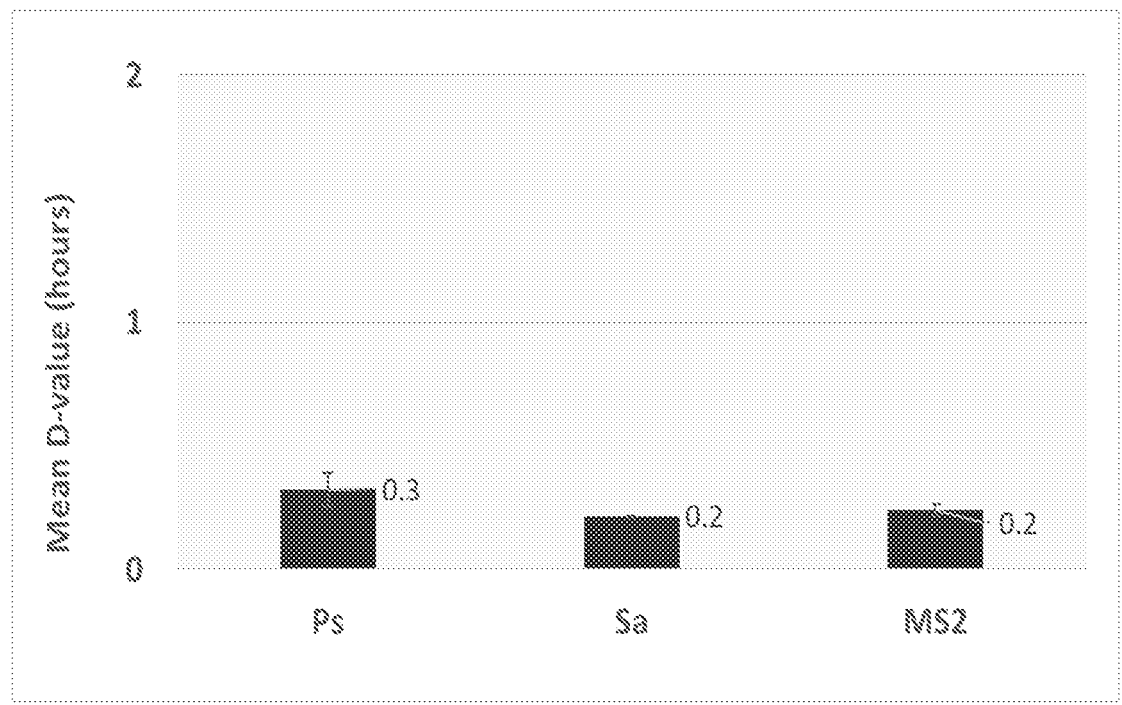
FIG. 55B illustrates the mean D-values (hours) from replicate tests per organism performed at the range of 5.3±2.4 ppmv.

FIGS. 55A and 55B illustrate the mean D-values (hours) from replicate tests per organism performed at the range of 0.11±0.04 ppmv (FIG. 55A) and 5.3±2.4 ppmv (FIG. 55B).

The results demonstrate that at 0.1 ppmv (FIG. 55A) a reduction of 90% of all organisms was rapid and comparable ranging from 0.5 to 1.2 hours (or 31 to 70 minutes).

As would be expected, the efficacy increased with treatment at 5 ppmv (FIG. 55B) with D-values ranging from 0.2 to 0.3 hours (or 13 to 19 minutes).

Based on this data, the time to achieve a 99.9% or 3-log reduction at 0.1 ppmv and 5 ppmv correlates to 1.5 to 3.6 hours and 0.6 to 0.9 hours, respectively.

Antimicrobial Generation and Monitoring Systems and Devices

A system for generating and monitoring an antimicrobial, is provided, the system comprising: a computational system; an antimicrobial sensor; and an antimicrobial generator, wherein the computational system, the antimicrobial generator, and the antimicrobial sensor are operatively connected. The computational system may be at least one of a microprocessor and a microcontroller. The system may further include an external communication device. The system may include a separate sensor sub-system comprising: at least one of a sensor sub-system microprocessor and a sensor sub-system microcontroller; a sensor sub-system external communications device; at least one of a sensor sub-system antimicrobial sensor and a sensor sub-system environmental sensor; and a sensor sub-system computational system. The system may include a separate generation sub-system comprising: at least one of a generation sub-system microprocessor and a generation sub-system microcontroller; a generation sub-system external communications device; and a generation sub-system antimicrobial generator. The external communications device, the computational system, the antimicrobial generator, and the at least one of an antimicrobial sensor and an environmental sensor may be oriented within an enclosed volume under treatment. At least one sensor sub-system and/or generation sub-system may be oriented within an enclosed volume under treatment.

A system for generating and monitoring an antimicrobial is provided, the system comprising: a sensor sub-system comprising: at least one of a sensor sub-system microprocessor and a sensor sub-system microcontroller, a sensor sub-system external communications device, at least one of a sensor sub-system antimicrobial sensor and a sensor sub-system environmental sensor, and a sensor sub-system computational system; a generation sub-system comprising: at least one of a generation sub-system microprocessor and a generation sub-system microcontroller, a generation sub-system external communications device, and a generation sub-system antimicrobial generator; and an enclosed space forming a volume under treatment. The sensor sub-system and the generation sub-system may be oriented within the enclosed volume under treatment. The sensor sub-system may be oriented within the enclosed volume under treatment and the generation sub-system may be oriented outside of the enclosed volume under treatment. The generation sub-system may be oriented within the enclosed volume under treatment and the sensor sub-system may be oriented outside of the enclosed volume under treatment. The system may include an HVAC air supply fluidically connected to the interior of the enclosed volume under treatment, the sensor sub-system may be oriented within the enclosed volume under treatment, the generation sub-system may be oriented outside of the enclosed volume under treatment, and the generation sub-system may be fluidically connected to the HVAC air supply. The system may include an HVAC air return fluidically connected to the interior of the enclosed volume under treatment, the generation sub-system may be oriented within the enclosed volume under treatment, the sensor sub-system may be oriented outside of the enclosed volume under treatment, and the sensor sub-system may be fluidically connected to the HVAC air return.

A system for generating and monitoring $ClO_2$ is provided, the system comprising: a device housing including an inlet; a microcontroller or microprocessor; a reagent container containing a reagent; a device for generating a $ClO_2$ from the reagent; and a sensing system. The system may include two reagent containers, and each reagent container may contain a different reagent. The device for generating the $ClO_2$ may be a microfluidic mixer, and the two reagents may mix in the microfluidic mixer to generate the $ClO_2$. The device for generating the $ClO_2$ may be an electrochemical generator. The sensing system may measure a concentration of $ClO_2$ in ambient air introduced via the inlet. The measurement of concentration of $ClO_2$ in the ambient air may be communicated to the microcontroller or microprocessor, and the microcontroller or microprocessor may cause the system to generate the $ClO_2$ if the $ClO_2$ concentration is below a target value. The system may include one reagent container and one reagent, the device for generating the $ClO_2$ may be an electrochemical generator, and the electrochemical generator may use an electrical potential to cause a reaction with the reagent that generates the $ClO_2$. The electrochemical generator may be a microfluidic device. The system may include a barometric sensor to sense a pressure of ambient air introduced via the inlet, the pressure may be communicated to the microcontroller or microprocessor, and a negative pressure may cause the microcontroller or microprocessor to pause $ClO_2$ generation until a neutral and/or positive pressure is sensed by the barometric sensor. The system may include an off-gas and waste chamber having a membrane, waste from the generation of the $ClO_2$ may be absorbed in an absorber material, and $ClO_2$ may exit the off-gas and waste chamber through the membrane and into an ambient atmosphere. The system may include an air pump electrically connected to the microcontroller or microprocessor and fluidically connected to the inlet via an air duct. The microcontroller or microprocessor is controlled by machine learning algorithms to alter system performance. The microcontroller or microprocessor may be controlled by artificial intelligence algorithms to alter system performance. The microcontroller or microprocessor may alter system performance automatically. The microcontroller or microprocessor may alter system performance by control by a user. The microcontroller or microprocessor may alter the system performance based upon at least one of: a detection of a virus in ambient air containing the system; a detection of bacteria in ambient air containing the system; an altitude of the system; a temperature of the system; changes in ambient air measured by changes in a concentration of $ClO_2$ in ambient air; changes in occupancy by living beings of an area containing the system; alterations for a user's preferences; prediction of cycles of occupancy and vacancy by living beings of the area containing the system; and a diagnosis of normal or abnormal performance of the system.

A network of systems for generating and monitoring $ClO_2$ is provided, the network of systems comprising: a plurality of systems for generating and monitoring $ClO_2$, including: a device housing including an inlet; a microcontroller; a reagent container containing a reagent; a microfluidic device for generating a $ClO_2$ from the reagent; and a sensing system; wherein the microcontroller includes a communication device capable of communication between the plurality of systems, wherein the communication device establishes distributed control of each system's microcontroller, and wherein the microcontroller is controlled by machine learning algorithms to alter system performance. The distributed control may include at least one of: adjusting individual systems to achieve a uniform or deliberately non-uniform distribution of $ClO_2$ in each individual sensor's location within a specified space; consumption of $ClO_2$; control of day and/or night generation cycles; using the sensing system to sense patterns across time, three-dimensional volumes, seasonal variations; sending patterns that are inferred or traced to a signal measured; and sensing patterns that are directly traceable to variations observed in $ClO_2$ concentrations across the network of systems installed across distinct spaces.

A network of systems for generating and monitoring $ClO_2$ concentration is provided, the network of systems comprising: a plurality of systems for generating and monitoring $ClO_2$, including: a device housing including an inlet; a microcontroller; a reagent container containing a reagent; a microfluidic device for generating a $ClO_2$ from the reagent;

and a sensing system; wherein the microcontroller includes a communication device capable of communication between the plurality of systems, wherein the communication device establishes distributed control of each system's microcontroller, and wherein the microcontroller is controlled by artificial intelligence algorithms to alter system performance. The distributed control may include at least one of: adjusting individual systems to achieve a uniform or deliberately non-uniform distribution of $ClO_2$ in each individual sensor's location within a specified space; consumption of $ClO_2$; control of day and/or night generation cycles; using the sensing system to sense patterns across time, three-dimensional volumes, seasonal variations; sending patterns that are inferred or traced to a signal measured; and sensing patterns that are directly traceable to variations observed in $ClO_2$ concentrations across the network of systems installed across distinct spaces.

Figure 61A:
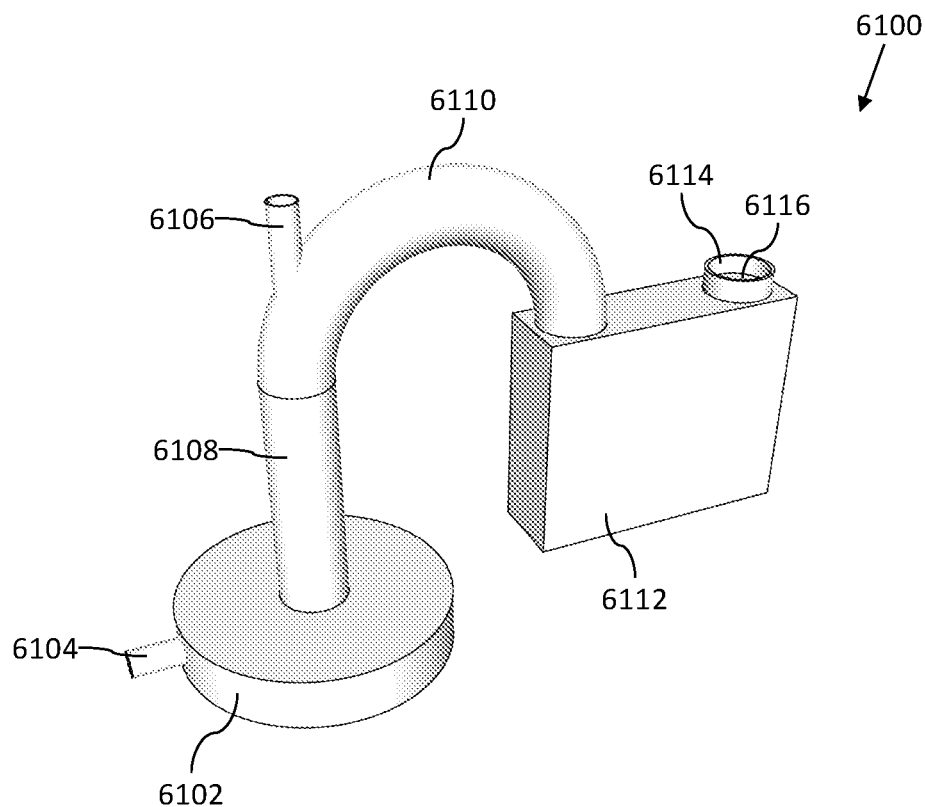
Figure 61B:
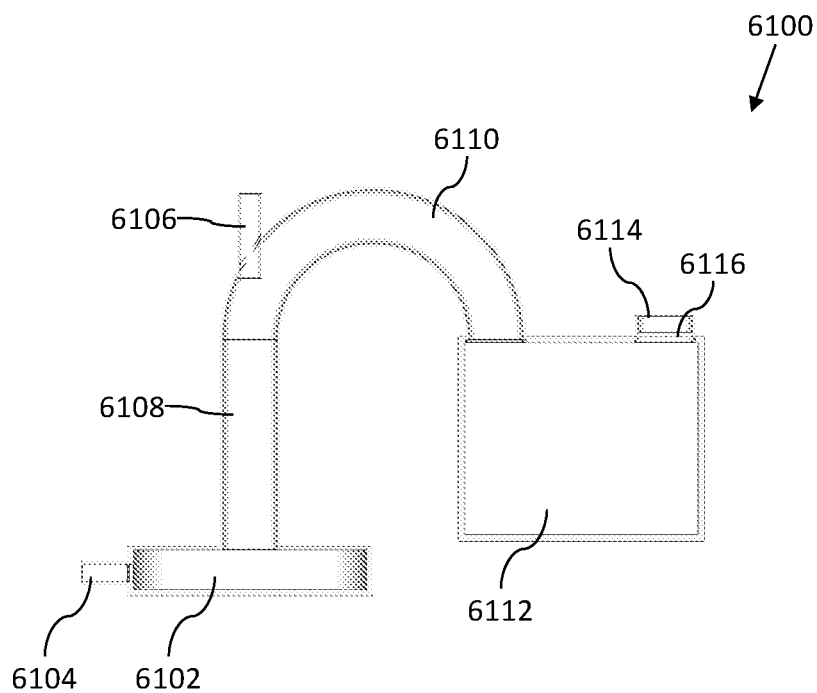

FIGS. 61A and 61B illustrates an example antimicrobial gas generator 6100. Generator 6100 includes a reaction chamber 6102 having an air/precursor inlet 6104, and optionally a UV light inlet 6106. UV light inlet 6106 may be operatively connected to a hollow tube 6108, thus permitting the UV light to travel into reaction chamber 6102. Hollow tube 6108 includes a curved portion 6110 in the shape of an inverted "U," which extends into the top of an evaporative waste trap 6112. Evaporative waste trap 6112 includes an antimicrobial outlet 6114 including a hydrophilic membrane 6116 (PTFE or the like).

In one aspect, generator 6100 may be a photonic activation antimicrobial generator. Generator 6100 may use UV light to activate one, two, or more precursors (e.g., liquid precursors) within reaction chamber 6102. The light may be UV-C wavelengths centered around 255 nm are known to cleave the sodium atom of chlorite ($NaClO_2$) to release $ClO_2$ through hollow tube 6108, into evaporative waste trap 6112, through membrane 6116, and into the volume under treatment through antimicrobial outlet 6114.

The described wavelength of the UV-C light is also known to reduce $ClO_2$ gas to intermediate species on the way to reduction to chlorine gas. Thus, the time of exposure of the $NaClO_2$ to the UV-C light is limited.

$NaClO_2$ is introduced to reaction chamber 6102 in liquid form. UV-C penetration depth is very small in water. Thus, generator 6100 causes the evaporation of the water containing sodium chlorite in reaction chamber 6102 in a manner such that "fresh surfaces" are exposed throughout the evaporation process achieving the goal of exposing all the sodium chlorite in that volume of water assuming that a dried salt does not block the UV light. Considering that a user expects generator 6100 to generate only small doses of $ClO_2$, it is noted that attempting to control a bulk solution of precursor removes the ability to control dose and/or deal with residues that interfere with reactions of sodium chlorite while it is solution without complicated membranes or machines. As such, generator 6100 causes fresh sodium chlorite to be exposed at an ever shrinking boundary layer between the atmosphere and a droplet containing an aqueous solution of sodium chlorite, by using vibrational atomization or nebulization to generate a highly uniform and size-limited pattern of droplets from incredibly small volumes of liquid when expelled into a gas flow stream past a UV source of the desired frequency. Providing the sodium chlorite in a volume of liquid defined as an evaporating droplet can ensure that all the sodium chlorite in solution is exposed to UV/UV-C, while still in an aqueous solution, and thus converted from $NaCLO_2$ to $CLO_2$.

Generator 6100 may also enable the control of total dose kinetics of UV or any other wavelength of light to a precursor liquid that can be nebulized or atomized into droplets. Flowing gas (entering inlet 6104 and exiting outlet 6114) in the hollow tube 6108 directs the flow of atomized antimicrobial out of outlet 6114. This flowing "sheath gas" is the atmosphere of the room, pumped into a port (which may be the same as or different from inlet 6104) in reaction chamber 6102, at a known quantity from which it is easy to calculate the flow velocity in the much larger diameter UV exposure portion of hollow tube 6108 (e.g., that portion between UV light inlet 6106 and reaction chamber 6102). Hollow tube 6108 may be much larger in diameter where the atomized droplets meet the sheath gas, which may result in the velocity of the combined streams of flowing gas and droplets of aqueous sodium chlorite able to be controlled simply by increasing or decreasing the gas sheath air pump velocity. Controlling this velocity of the combined streams controls the length of exposure to the highly focused UV-C light provided from UV light inlet 6106 (e.g., via an LED bulb) to the simultaneously moving and evaporating droplets for between 0.1 and 5.0 seconds. Changes to the quantity of gas pumped in as the sheath gas, diameter of the geometry of the unit, and/or a combination of these types of variables can provide a much larger range of time-of-flight exposure of an evolving UV-C and aqueous solution interface boundary being constantly refreshed with precursor material by the physics of evaporation of small droplets.

In another aspect, gas generator 6100 is an electrochemical generator. In this embodiment, UV light inlet 6106 is eliminated, and an electrochemical generator cell is oriented inside reaction chamber 6102. The electrochemical generator cell includes an electrode array adjacent to the inlet side of reaction chamber 6102, wherein reaction chamber 6102 further includes a mesh atomizer.

In each aspect, generator 6100 produces atomized antimicrobial droplets and separates the antimicrobial from the waste. That is, the atomized antimicrobial exits evaporative waste trap 6112 via membrane 6116 and outlet 6114, while waste is unable to pass through membrane 6116 and falls instead to the bottom of evaporative waste trap 6112.

Generator 6100 additionally uses the evaporation of the droplets to minimize waste volume. Evaporation of the liquid droplets in the time of flight, combined with a separation mechanism such as a hydrophobic small pore membrane (membrane 6116) that is highly permeable to small gaseous molecules, enables the separation of the solid waste (and/or liquid waste should some percentage of droplets not fully evaporate due to size, coalescence of droplets, or other causes).

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants use the term "and" in a list, such as "one or more of A, B, and C," Applicant intends the term "and" to be interpreted as "and/or." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to take into consideration the degree of precision available in manufacturing. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of aspects thereof, and while the aspects have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A closed-loop system for generating and monitoring an antimicrobial, comprising:
   a control sub-system comprising:
      a controller unit;
   a communications sub-system comprising:
      one or more of a wired communication mechanism and a wireless communication mechanism for connecting to an external network;
   a sensing sub-system comprising:
      one or more sensor,
         wherein the one or more sensor is operatively connected to the control sub-system;
   a generation sub-system;
   wherein the antimicrobial is applied to a volume under treatment;
   wherein the sensing sub-system samples air from the volume under treatment continuously or on a predetermined schedule and measures the concentration of the antimicrobial present in the air from the volume under treatment; and
   wherein the generation sub-system generates the antimicrobial in response to a difference between an antimicrobial concentration target value and the antimicrobial concentration sensing sub-system measurement.

2. The closed-loop system of claim 1, further comprising an air pump located upstream or downstream of the one or more sensor, wherein the air pump draws the air from the volume under treatment into contact with the one or more sensor.

3. The closed-loop system of claim 1, wherein the generation sub-system comprises a reactor, wherein the one or more sensor is oriented in one or more plenum, wherein the one or more sensor and the one or more plenum comprise one or more pre-sensor located in a plenum upstream of a reactor, and one or more post-sensor located in a plenum downstream from the reactor.

4. The closed-loop system of claim 3, further comprising an air pump located downstream of the one or more pre-sensor and upstream of the one or more post-sensor.

5. The closed-loop system of claim 1, wherein the antimicrobial is an antimicrobial gas or vapor.

6. The closed-loop system of claim 1, wherein the generation sub-system comprises a reactor including a mixing chamber, wherein two or more reagents are combined in the mixing chamber to create an antimicrobial, and wherein the generation sub-system further comprises a plurality of liquid reagent tanks, wherein the reagent tanks are fluidically connected to the reactor mixing chamber.

7. The closed-loop system of claim 1, wherein the generation sub-system discontinues generation of the antimicrobial in response to a difference between the antimicrobial concentration target value and the antimicrobial concentration sensing sub-system measurement.

8. A closed-loop system for generating and monitoring an antimicrobial, comprising:
   a control sub-system comprising:
      a controller unit;
   a communications sub-system comprising:
      one or more of a wired communication mechanism and a wireless communication mechanism for connecting to an external network;
   a sensing sub-system comprising:
      one or more sensor,
         wherein the one or more sensor is operatively connected to the control sub-system;
   a generation sub-system;
   wherein the antimicrobial is applied to a volume under treatment;
   wherein the sensing sub-system samples air from the volume under treatment continuously or on a predetermined schedule and measures the concentration of the antimicrobial present in the air from the volume under treatment;
   wherein the generation sub-system generates the antimicrobial in response to a difference between an antimicrobial concentration target value and the antimicrobial concentration sensing sub-system measurement; and
   wherein the generation sub-system discontinues generation of the antimicrobial in response to a difference between the antimicrobial concentration target value and the antimicrobial concentration sensing sub-system measurement.

9. The closed-loop system of claim 8, further comprising an air pump located upstream or downstream of the one or more sensor, wherein the air pump draws the air from the volume under treatment into contact with the one or more sensor.

10. The closed-loop system of claim 8, wherein the generation sub-system comprises a reactor, wherein the one or more sensor is oriented in one or more plenum, wherein the one or more sensor and the one or more plenum comprise one or more pre-sensor located in a plenum upstream of the reactor, and one or more post-sensor located in a plenum downstream from the reactor.

11. The closed-loop system of claim 10, further comprising an air pump located downstream of the one or more pre-sensor and upstream of the one or more post-sensor.

12. The closed-loop system of claim 8, wherein the antimicrobial is an antimicrobial gas or vapor.

13. The closed-loop system of claim 8, wherein the generation sub-system comprises a reactor including a mixing chamber, wherein two or more reagents are combined in the mixing chamber to create an antimicrobial, and wherein the generation sub-system further comprises a plurality of liquid reagent tanks, wherein the reagent tanks are fluidically connected to the reactor mixing chamber.

14. A closed-loop system for generating and monitoring an antimicrobial, comprising:
   a control sub-system comprising:
      a controller unit;
   a communications sub-system comprising:
      one or more of a wired communication mechanism and a wireless communication mechanism for connecting to an external network;
   a sensing sub-system comprising:
      one or more sensor,
         wherein the one or more sensor is operatively connected to the control sub-system;
   a generation sub-system;
   wherein the antimicrobial is applied to a volume under treatment;
   wherein the sensing sub-system samples air from the volume under treatment continuously or on a predetermined schedule and measures the concentration of the antimicrobial present in the air from the volume under treatment;
   wherein the generation sub-system generates the antimicrobial in response to a difference between an antimicrobial concentration target value and the antimicrobial concentration sensing sub-system measurement; and
   wherein the generation sub-system comprises a reactor including a mixing chamber, wherein two or more reagents are combined in the mixing chamber to create an antimicrobial, and wherein the generation sub-system further comprises a plurality of liquid reagent tanks, wherein the reagent tanks are fluidically connected to the reactor mixing chamber.

15. The closed-loop system of claim 14, wherein the one or more sensor is oriented in one or more plenum, wherein the one or more sensor and the one or more plenum comprise one or more pre-sensor located in a plenum upstream of the reactor, and one or more post-sensor located in a plenum downstream from the reactor.

16. The closed-loop system of claim 14, wherein the generation sub-system discontinues generation of the antimicrobial in response to a difference between the antimicrobial concentration target value and the antimicrobial concentration sensing sub-system measurement.

17. The closed-loop system of claim 1, wherein the system includes two operating modes, the first operating mode being a prevention mode for application in the volume under treatment during occupation by a human, and the second operating mode being a decontamination mode for application in the volume under treatment while unoccupied by a human.

18. The closed-loop system of claim 8, wherein the system includes two operating modes, the first operating mode being a prevention mode for application in the volume under treatment during occupation by a human, and the second operating mode being a decontamination mode for application in the volume under treatment while unoccupied by a human.

19. The closed-loop system of claim 14, wherein the system includes two operating modes, the first operating mode being a prevention mode for application in the volume under treatment during occupation by a human, and the second operating mode being a decontamination mode for application in the volume under treatment while unoccupied by a human.

* * * * *